US010120974B2

(12) United States Patent
Spierings

(10) Patent No.: US 10,120,974 B2
(45) Date of Patent: Nov. 6, 2018

(54) METHOD FOR PREDICTION OF AN IMMUNE RESPONSE AGAINST MISMATCHED HUMAN LEUKOCYTE ANTIGENS

(71) Applicant: UMC UTRECHT HOLDING B.V., Utrecht (NL)

(72) Inventor: Hendrikus Theodorus Spierings, Zeist (NL)

(73) Assignee: UMC UTRECHT HOLDING B.V., Utrecht (NL)

( * ) Notice: Subject to any disclaimer, the term of this patent is extended or adjusted under 35 U.S.C. 154(b) by 260 days.

(21) Appl. No.: 14/441,187

(22) PCT Filed: Nov. 8, 2013

(86) PCT No.: PCT/EP2013/073386
§ 371 (c)(1),
(2) Date: May 7, 2015

(87) PCT Pub. No.: WO2014/072467
PCT Pub. Date: May 15, 2014

(65) Prior Publication Data
US 2015/0278434 A1    Oct. 1, 2015

Related U.S. Application Data

(60) Provisional application No. 61/724,103, filed on Nov. 8, 2012, provisional application No. 61/729,440, filed on Nov. 23, 2012.

(30) Foreign Application Priority Data

Nov. 8, 2012  (EP) ..................... 12075124
Nov. 8, 2012  (EP) ..................... 12075125
Nov. 23, 2012 (EP) ..................... 12194008
Jan. 24, 2013 (EP) ..................... 13075011

(51) Int. Cl.
*G06F 19/00* (2018.01)
*G06F 19/18* (2011.01)
*G01N 33/68* (2006.01)
*G06F 19/10* (2011.01)
*C12Q 1/6881* (2018.01)
*G16H 50/30* (2018.01)
*G16H 50/20* (2018.01)

(52) U.S. Cl.
CPC .......... *G06F 19/18* (2013.01); *C12Q 1/6881* (2013.01); *G01N 33/6878* (2013.01); *G06F 19/10* (2013.01); *G16H 50/20* (2018.01); *G16H 50/30* (2018.01); *C12Q 2600/106* (2013.01); *G01N 2333/70539* (2013.01); *G01N 2800/245* (2013.01)

(58) Field of Classification Search
None
See application file for complete search history.

(56) References Cited

U.S. PATENT DOCUMENTS

2011/0135617 A1    6/2011 Kruse

OTHER PUBLICATIONS

Claas F H J: "Predictive parameters for in vivo alloreactivity", in: Transplant Immunology, vol. 10, No. 2-3, Aug. 1, 2002, pp. 137-142.
René J Duquesnoy: "HLAMatchmaker: a molecularly based algorithm for histocompatibility determination. I. Description of the algorithm", in: Human Immunology, vol. 63, No. 5, May 1, 2002, pp. 339-352.
Marlies K.A Dankers et al: "The HLA-DR phenotype of the responder is predictive of humoral response against HLA class i antigens", in: Human Immunology, vol. 65, No. 1, Jan . 1, 2004, pp. 13-19.
Papassavas AC: "HLA peptide-mediated strategies for modulation of cellular and humoral immune response in transplantation", in: Current Pharmacogenomics, Bentham Science Publishers, US, vol. 1, No. 1, Mar. 1, 2003, pp. 17-36.
Reinsmoen N L: "Cellular methods used to evaluate the immune response in transplantation", in: Tissue Antigens, Munksgaard, Copenhagen, DK, vol. 59, No. 4, Aug. 1, 2002, pp. 241-250.
Urban Sester et al: "Rapid Identification of Preformed Alloreactive T Cells for Use in a Clinical Setting", in: Transplantation, vol. 78, No. 4, Aug. 1, 2004, pp. 607-614.
Wang Peng et al: "A systematic assessment of MHC class II peptide binding predictions and evaluation of a consensus approach", in: PLOS Computational Biology, Public Library of Science, US, vol. 4, No. 4, Apr. 1, 2008, pp. E1000048-1.
Lin Hong Huang et al: "Evaluation of MHC-II peptide binding prediction servers: applications for vaccine research", in: BMC Bioinformatics, Biomed Central, London, GB, vol. 9, No. Suppl 12, Dec. 12, 2008, p. S22.
Binkowski et al., Predicting HLA Class I Non-Permissive Amino Acid Residues Substitutions, PLoS ONE, 2012, vol. 7, No. 8, pp. 1-12.
Deluca et al., High-throughput Minor Histocompatibility Antigen Prediction, Bioinformatics, 2009, vol. 25, No. 18, pp. 2411-2417.
Otten et al., Predicted indirectly recognizable HLA epitopes presented by HLA-DR correlate with the de novo development of donor-specific HLA IgG antibodies after kidney transplantation, Human Immunology, 74, Dec. 8, 2012, pp. 290-296.

(Continued)

*Primary Examiner* — Michael L Borin
(74) *Attorney, Agent, or Firm* — Agris & Von Natzmer, LLP; Joyce Von Natzmer

(57) ABSTRACT

Disclosed is a method for prediction of an immune response against human leukocyte antigens (HLA) after transplantation, said method comprising HLA-typing of the donor and/or donor material and recipient to determine HLA-mismatches and determination of the number of predicted indirectly recognized HLA epitopes (PIRCHES). In particular, methods for selecting and/or screening donor material for allogeneic transplantation, for example for selecting donor material with permissible mismatches from mismatched unrelated donors and pre-transplantation prediction of an unwanted alloreactivity that could occur after transplantation of hematopoietic stem cells, cord blood, kidneys and/or other cells, tissues or organs are disclosed.

23 Claims, 22 Drawing Sheets

(56) References Cited

OTHER PUBLICATIONS

Figure 1:
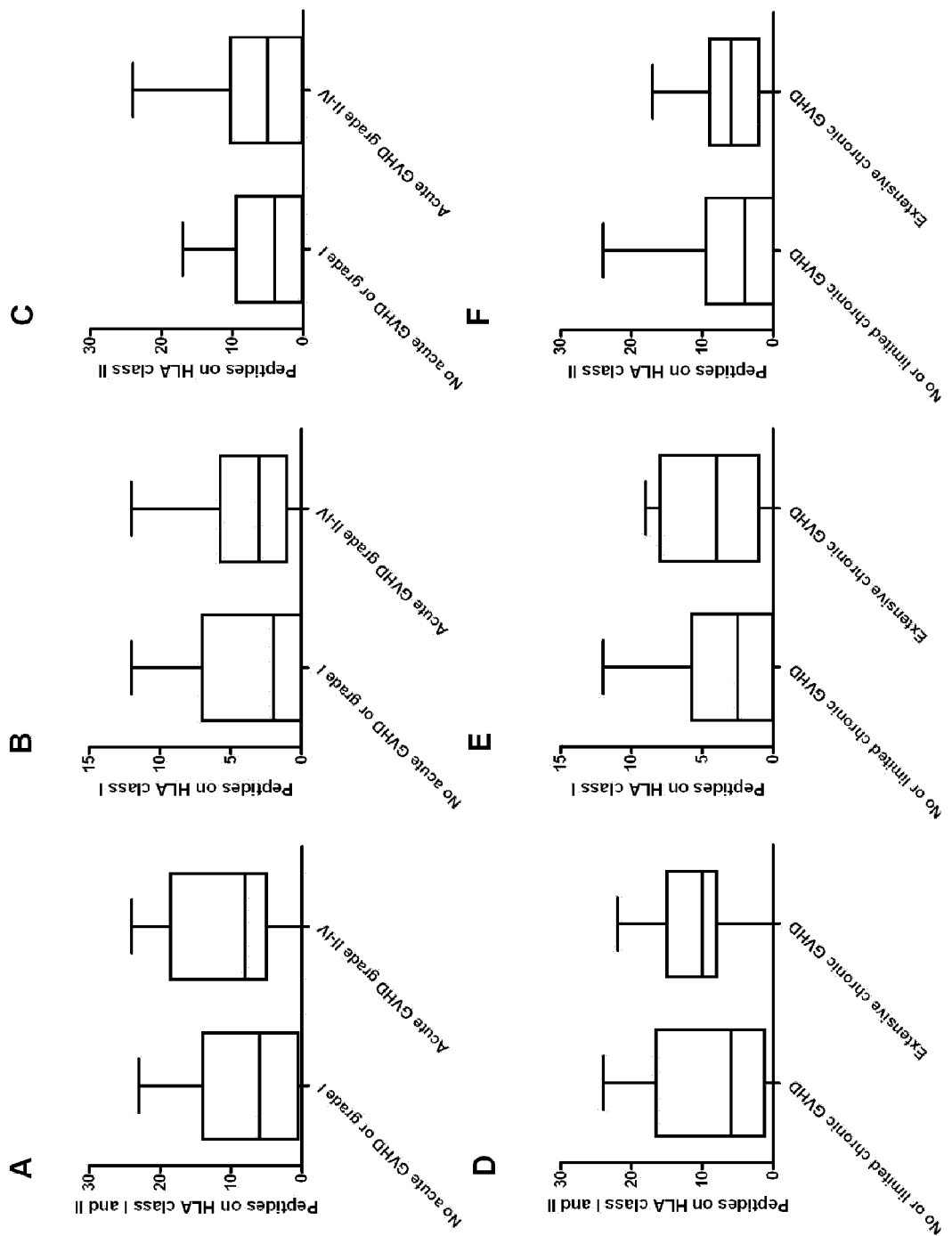
Figure 1:
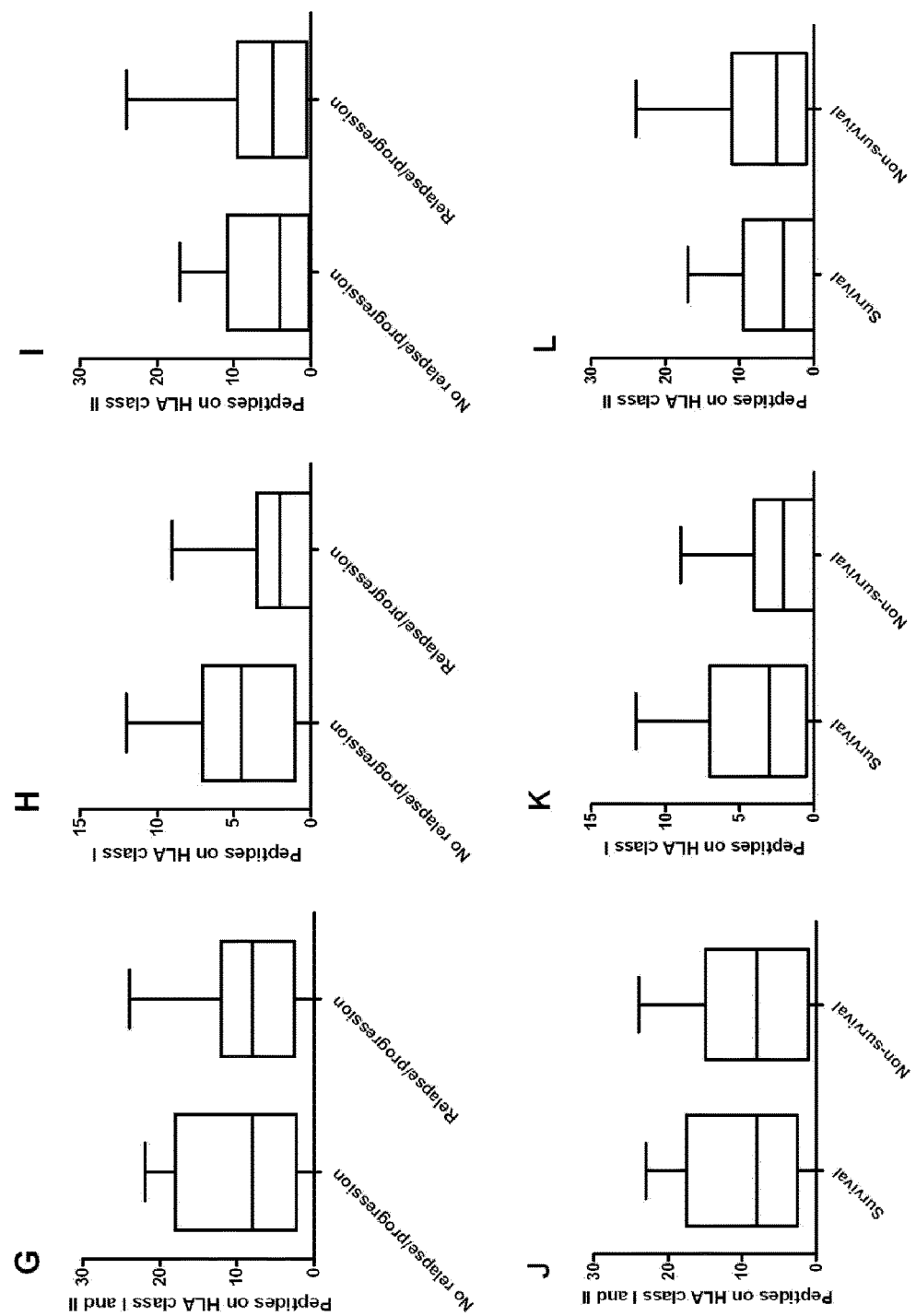

Papassavas et al., Definition of the Immunogenic HLA Epitopes Based on an Epitope Prediction Algorithm, Transplantation Proceedings, 34, 2002, pp. 2049-2052.

Yanover et al., HLA mismatches and hematopoietic cell transplantation: structural simulations assess the impact of changes in peptide binding specificity on transplant outcome, National Institutes of Health Author Manuscript, Jan. 28, 2014, pp. 1-22.

Amir, A.L., et al., Allo-HLA-reactive T cells inducing graft-versus-host disease are single peptide specific, Blood 2011, vol. 118, pp. 6733-6742.

Askar, M., et al., Predictions in the face of clinical reality: HistoCheck versus high-risk HLA allele mismatch combinations responsible for severe acute graft-versus-host disease, Biol. Blood Marrow Transplant, 2011, vol. 17, pp. 1409-1415.

Ballen, KK., et al., Selection of optimal alternative graft source: mismatched unrelated donor, umbilical cord blood, or haploidentical transplant, Blood 2012, vol. 119(9), pp. 1972-1980.

Buus, S., et al., Sensitive quantitative predictions of peptide-MHC binding by a 'Query by Committee' artificial neural network approach, Tissue Antigens 2003, vol. 62, pp. 378-384.

Chakraverty, R., et al., The role of antigen-presenting cells in triggering graft-versus-host disease and graft-versus-leukemia, Blood 2007, vol. 110, pp. 9-17.

Ciubotariu, R., et al., Persistent allopeptide reactivity and epitope spreading in chronic rejection of organ allografts, J. Clin Invest 1998, vol. 101(2), pp. 398-405.

Duquesnoy, R., et al.,HLAMatchmaker-defined triplet matching is not associated with better survival rates of patients with class I HLA allele mismatched hematopoietic cell transplants from unrelated donors, Biol.Blood Marrow Transplant, 2008, vol. 14, pp. 1064-1071.

Duquesnoy, R.J., et al., HLAMatchmaker: a molecularly based algorithm for histocompatibility determination. II. Verification of the algorithm and determination of the relative immunogenicity of amino acid triplet-defined epitopes, Hum.Immunol. 2002, vol. 63, pp. 353-363.

Duquesnoy, R.J., et al., HLAmatchmaker: a molecularly based algorithm for histocompatibility determination. III. Effect of matching at the HLA-A,B amino acid triplet level on kidney transplant survival, Transplantation 2003, vol. 75, pp. 884-889.

Duquesnoy, R.J., HLAMatchmaker: a molecularly based algorithm for histocompatibility determination. I. Description of the algorithm, Hum Immunol 2002, vol. 63, pp. 339-352.

Duquesnoy, RJ., A structurally based approach to determine HLA compatibility at the humoral immune level, Hum Immunol 2006, vol. 67, pp. 847-862.

Duquesenoy, RJ., Antibody-reactive epitope determination with HLAMatchmaker and its clinical applications, Tissue Antigens 2011, vol. 77, pp. 525-534.

Elsner, H.A., et al.,HistoCheck: rating of HLA class I and II mismatches by an internet-based software tool, Bone Marrow Transplant, 2003, vol. 33, pp. 165-169.

Falk, K., et al., Allele-specific motifs revealed by sequencing of self-peptides eluted from MHC molecules, Nature 1991, vol. 351, pp. 290-296.

Ferrara, J.L., et al., Graft-versus-host disease, Lancet 2009, vol. 373, pp. 1550-1561.

Fleischhauer, K., et al., Effect of T-cell-epitope matching at HLA-DPB1 in recipients of unrelated-donor haemopoietic-cell transplantation: a retrospective study, Lancet Oncol 2012, vol. 13(4), pp. 366-374.

Flomenberg, N., et al., Impact of HLA class I and class II high-resolution matching on outcomes of unrelated donor bone marrow transplantation: HLA-C mismatching is associated with a strong adverse effect on transplantation outcome, Blood 2004, vol. 104, pp. 1923-1930.

Fuller, TC., et al., The humoral immune response against an HLA class I allodeterminant correlates with the HLA-DR phenotype of the responder, Transplantation 1999, vol. 68, pp. 173-182.

Furst, D., et al., High resolution HLA-matching in hematopoietic stem cell transplantation: a retrospective collaborative analysis, Blood 2013.

Gupta, V., et al., Comparable survival after HLA-well-matched unrelated or matched sibling donor transplantation for acute myeloid leukemia in first remission with unfavorable cytogenetics at diagnosis. Blood 2010, vol. 116, pp. 1839-1848.

Heemskerk, MB., et al., The HistoCheck algorithm does not predict T-cell alloreactivity in vitro, Bone Marrow Transplant 2005, vol. 36, No. 10, pp. 927-928.

Hoof, I., et al., NetMHCpan, a method for MHC class I binding prediction beyond humans, Immunogenetics 2009, vol. 61, pp. 1-13.

Hornick, Pl., et al., Significant frequencies of T cells with indirect antidonor specificity in heart graft recipients with chronic rejection, Circulation 2000, vol. 101(20), pp. 2405-2410.

Hurley, CK., et al., The impact of HLA unidirectional mismatches on the outcome of myeloablative hematopoietic stem cell transplantation with unrelated donors, Blood 2013, vol. 121(23), pp. 4800-4806.

Kawase, T., et al., High-risk HLA allele mismatch combinations responsible for severe acute graft-versus-host disease and implication for its molecular mechanism, Blood 2007, vol. 110, pp. 2235-2241.

Kawase, T., et al., HLA mismatch combinations associated with decreased risk of relapse: implications for the molecular mechanism, Blood 2009, vol. 113, pp. 2851-2858.

Kersmir, C., et al., Prediction of proteasome cleavage motifs by neural networks, Protein Eng 2002, vol. 15, pp. 287-296.

Lee, SJ., et al., High-resolution donor-recipient HLA matching contributes to the success of unrelated donor marrow transplantation, Blood 2007, vol. 110(13), pp. 4576-4583.

Liu, HL., et al., Unrelated cord blood transplantation for newly diagnosed patients with severe acquired aplastic anemia using a reduced-intensity conditioning: high graft rejection, but good survival, Bone Marrow Transplant 2012, vol. 47(9), pp. 1186-1190.

Liu, Z., et al., Indirect recognition of donor HLA-DR peptides in organ allograft rejection, J Clin Invest 1996, vol. 98(5), pp. 1150-1157.

Maiers, M.,et al., High-resolution HLA alleles and haplotypes in the United States population, Hum.Immunol. 2007, vol. 68, pp. 779-788.

Nielsen, M., et al., MHC class II epitope predictive algorithms, Immunology 2010, vol. 130, pp. 319-328.

Nielsen, M., et al., NetMHCIIpan-2.0—Improved panspecific HLA-DR predictions using a novel concurrent alignment and weight optimization training procedure, Immunome Res 2010, 6:9.

Nielsen, M., et al., NetMHCpan, a method for quantitative predictions of peptide binding to any HLA-A and-B locus protein of known sequence, PLoS.One. 2007, vol. 2, pp. e796.

Nielsen, M., et al., NN-align, An artificial neural network-based alignment algorithm for MHC class II peptide binding prediction, BMC.Bioinformatics, 2009, vol. 10, pp. 296.

Nielsen, M., et al., Prediction of MHC class II binding affinity using SMM-align, a novel stabilization matrix alignment method, BMC. Bioinformatics, 2007, vol. 8, pp. 238.

Nielsen, M., et al., The role of the proteasome in generating cytotoxic T-cell epitopes: insights obtained from improved predictions of proteasomal cleavag., Immunogenetics 2005, vol. 57, pp. 33-41.

Otten, HG., et al., Predicted indirectly recognizable HLA epitopes presented by HLA-DR correlate with the de novo development of donorspecific HLA IgG antibodies after kidney transplantation, Hum Immunol 2012, vol. 74(3), pp. 290-296.

Papassavas, AC., et al., Is there WHC Class II restriction of the response to MHC Class I in transplant patients? Transplantation 2002, vol. 73, pp. 642-651.

Peters, B., et al., A community resource benchmarking predictions of peptide binding to MHC-I molecules, PLoS Comput Biol 2006, vol. 2, pp. e65.

Shaw, BE., et al., Scoring for HLA matching? A clinical test of HistoCheck, Bone Marrow Transplant 2004, vol. 34(4), pp. 367-368.

(56) References Cited

OTHER PUBLICATIONS

Southwood, S., et al., Several common HLA-DR types share largely overlapping peptide binding repertoires, J. Immunol. 1998, vol. 160, pp. 3363-3373.

Spellman, S., et al., Scoring HLA Class I Mismatches by HistoCheck Does Not Predict Clinical Outcome in Unrelated Hematopoietic Stem Cell Transplantation, Biol.Blood Marrow Transplant. 2012.

Suciu-Foca, N., et al., Indirect allorecognition of donor HLA-DR peptides in chronic rejection of heart allografts, Transplant Proc 1998, vol. 30(8), pp. 3999-4000.

Terasaki, P.I., et al., Human leukocyte antigen antibodies and chronic rejection: from association to causation, Transplantation 2008, vol. 86, pp. 377-383.

Numbers of PIRCHE-II

Numbers of PIRCHE-II

Numbers of PIRCHE-I+II

Numbers of PIRCHE-II

Fig. 3

| nr. | Age of recipient [years] | Gender recipient/donor | time till ectomy [months] | HLA class I mismatch | HLA-DRB1 typing of recipient | Immunogenic alleles | Non-immunogenic alleles |
|---|---|---|---|---|---|---|---|
| 1 | 26 | M/F | 143 | A*32:01, B*15:17 | DRB1*03:01, - | A*32:01, B*15:17 | - |
| 2 | 51 | M/M | 46 | A*03:01, B*18:01 | DRB1*03:01, - | A*03:01 | B*18:01 |
| 3 | 48 | M/F | 0 | A*02:01, B*41:01 | DRB1*04:01, DRB1*07:01 | A*02:01, B*41:01 | - |
| 4 | 54 | M/M | 0 | A*01:01, A*24:02, B*39:06 | DRB1*03:01, DRB1*15:01 | A*01:01, A*24:02 | B*39:06 |
| 5 | 47 | M/M | 10 | A*03:01, B*07:02 | DRB1*07:01, DRB1*13:01 | B*07:02 | A*03:01 |
| 6 | 29 | M/M | 2 | A*02:01, B*57:01, B*49:01# | DRB1*07:01, DRB1*15:01 | A*02:01, B*49:01 | B*57:01 |
| 7 | 32 | M/M | 0 | A*01:01, B*08:01 | DRB1*04:01, DRB1*15:01 | A*01:01, B*08:01 | - |
| 8 | 54 | M/F | 0 | B*44:02 | DRB1*04:01, DRB1*11:01 | B*44:02 | - |
| 9 | 43 | M/F | 0 | B*40:01 | DRB1*01:01, DRB1*04:01 | B*40:01 | - |
| 10 | 69 | M/M | 0 | A*24:02, B*18:01, B*35:03 | DRB1*04:01, DRB1*07:01 | A*24:02, B*18:01 | B*35:03 |
| 11 | 53 | M/F | 0 | A*03:01, B*07:02, B*15:01# | DRB1*15:01, DRB1*03:01 | A*03:01, B*07:02, B*15:01 | - |
| 12 | 66 | M/M | 0 | A*24:02, B*44:02, B*39:06 | DRB1*04:01, DRB1*11:01 | - | A*24:02, B*44:02, B*39:06 |
| 13 | 35 | M/M | 0 | A*24:02, B*39:06, B*51:01 | DRB1*04:01, - | A*24:02, B*39:06, B*51:01 | - |
| 14 | 47 | M/M | 101 | A*02:01, B*27:05 | DRB1*09:01, DRB1*15:01 | A*02:01, B*27:05 | - |
| 15 | 59 | F/M | 4 | A*02:01, B*51:01 | DRB1*12:01, - | A*02:01 | B*51:01 |
| 16 | 54 | F/F | 3 | A*01:01, B*07:02 | DRB1*03:01, DRB1*15:01 | A*01:01, B*07:02 | - |
| 17 | 27 | F/M | 0 | B*51:01 | DRB1*03:01, - | B*51:01 | - |
| 18 | 53 | F/M | 0 | A*01:01, A*02:01, B*08:01, B44& | DRB1*08:01, DRB1*11:01 | A*01:01, A*02:01, B*08:01, B44 | - |
| 19 | 45 | F/M | 0 | A*02:01, B*07:02 | DRB1*07:01, DRB1*13:01# | A*02:01, B*07:02 | - |
| 20 | 30 | F/F | 0 | A*32:01 | DRB1*03:01, - | A*32:01 | - |
| 21 | 17 | F/F | 38 | B*57:01 | DRB1*03:01, DRB1*13:01# | B*57:01 | - |

(#) No DNA available for high resolution typing. Typing has been extrapolated from the serological broad typing.
(&)No DNA available for high resolution typing. Number of eplets/peptides calculated as average of B*44:02 and B*44:03

Figure 6:
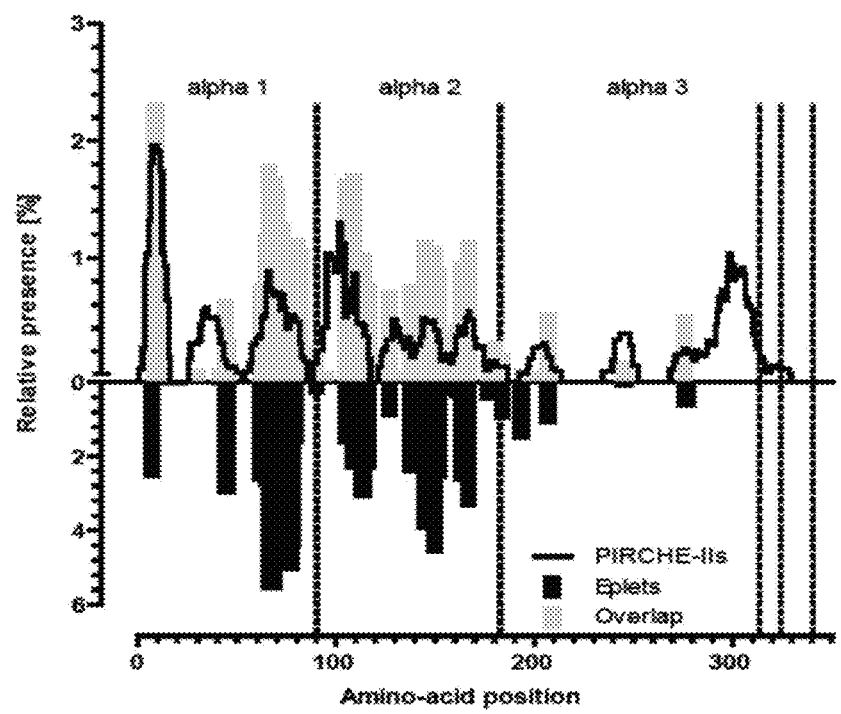

Fig. 6
A
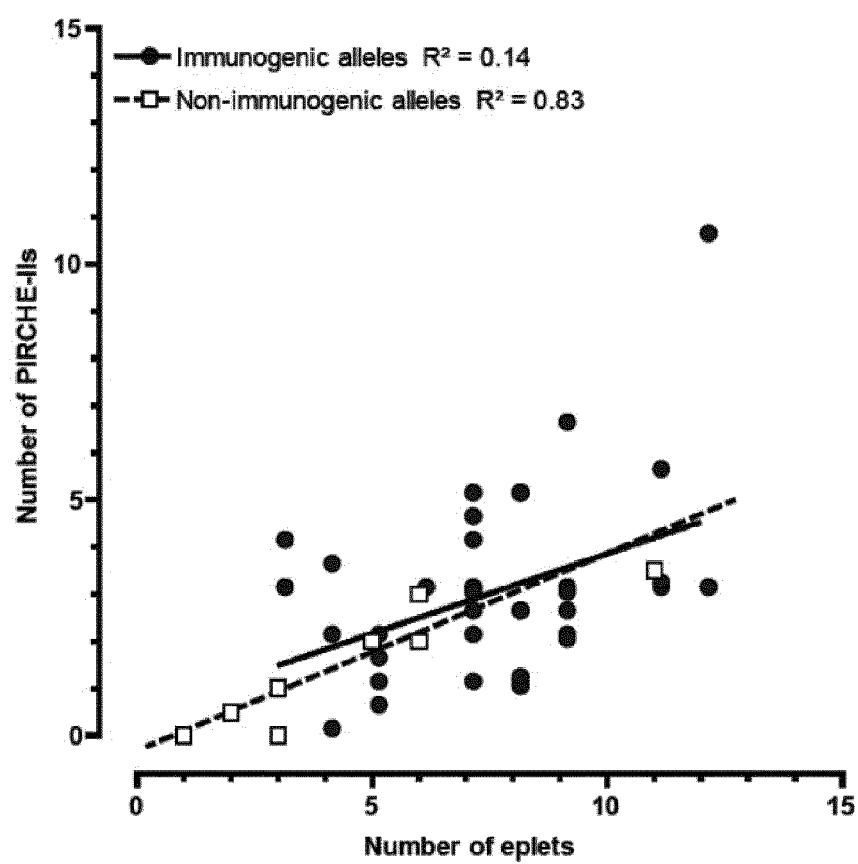
B
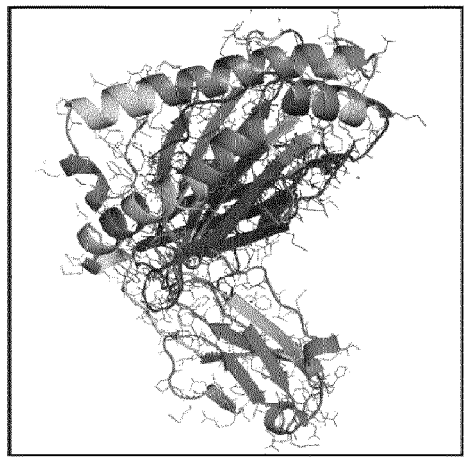

C

A

B

Fig. 8
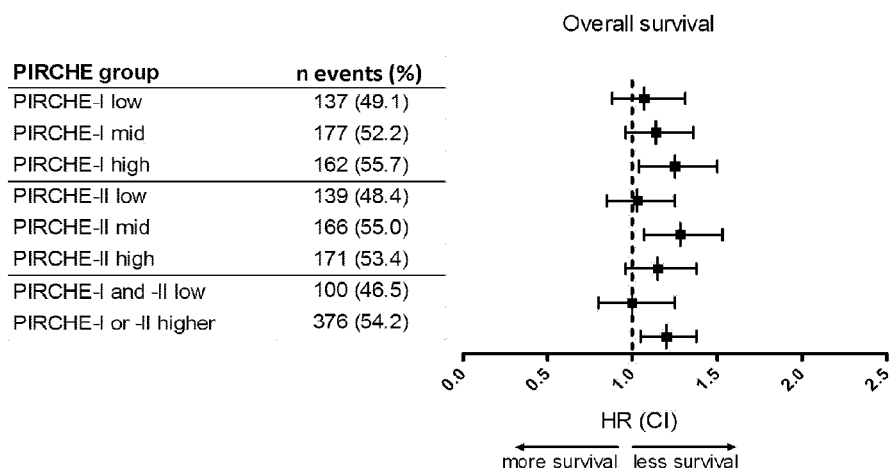
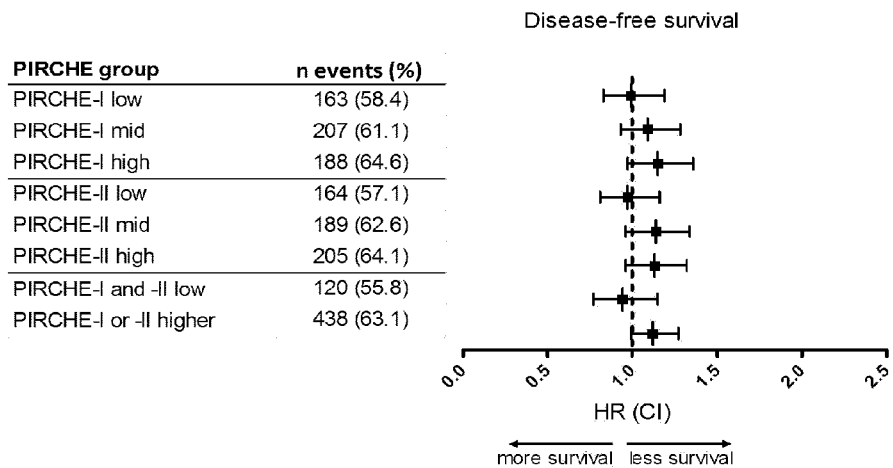
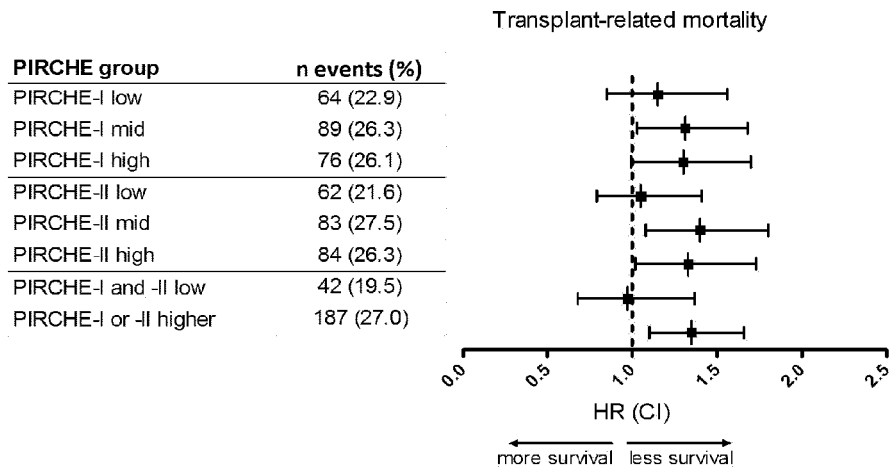

Fig. 8 (cont.)
D
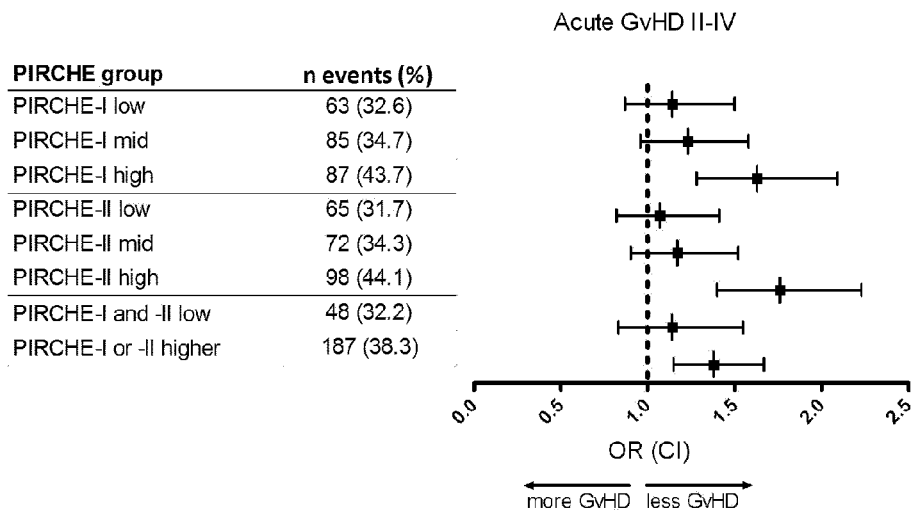
E
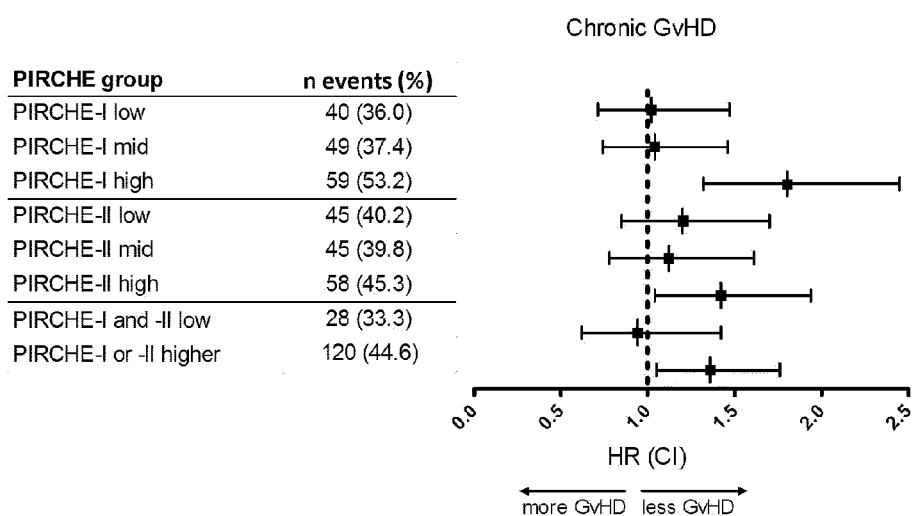

Fig. 9
A
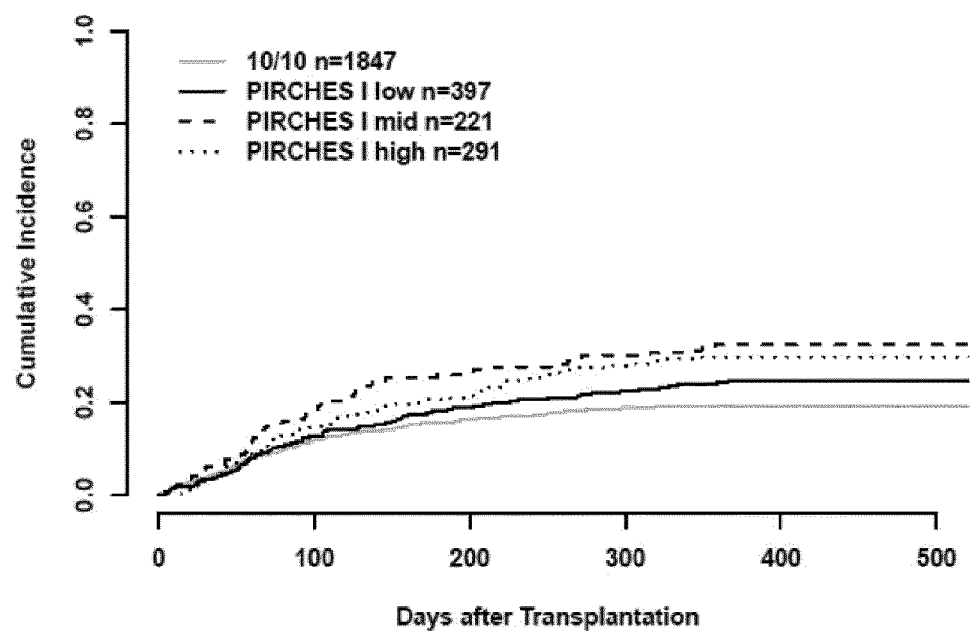
B
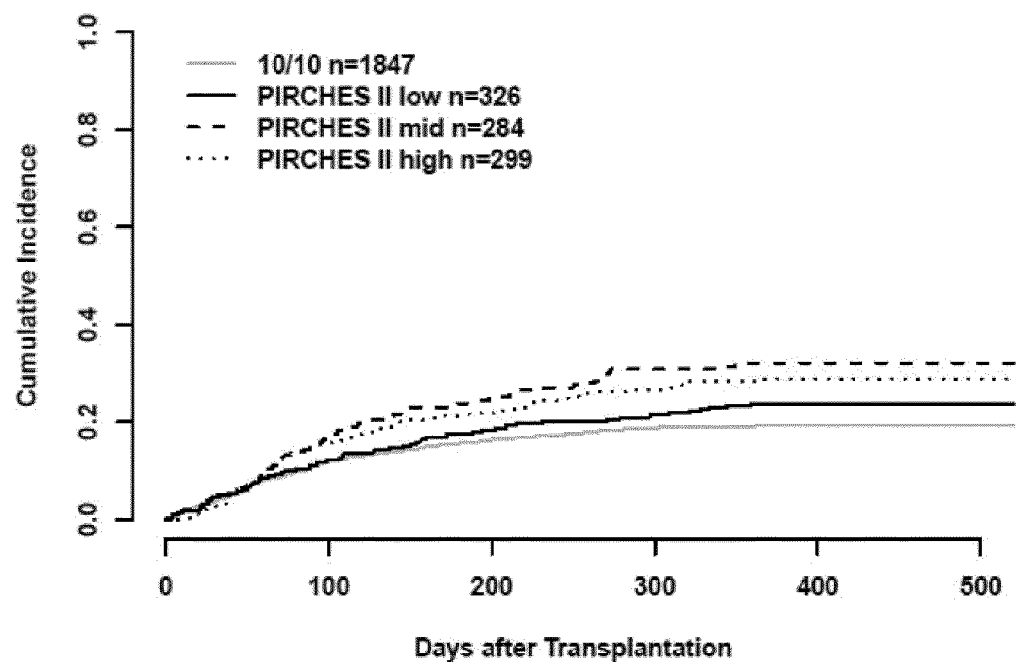

Fig. 11
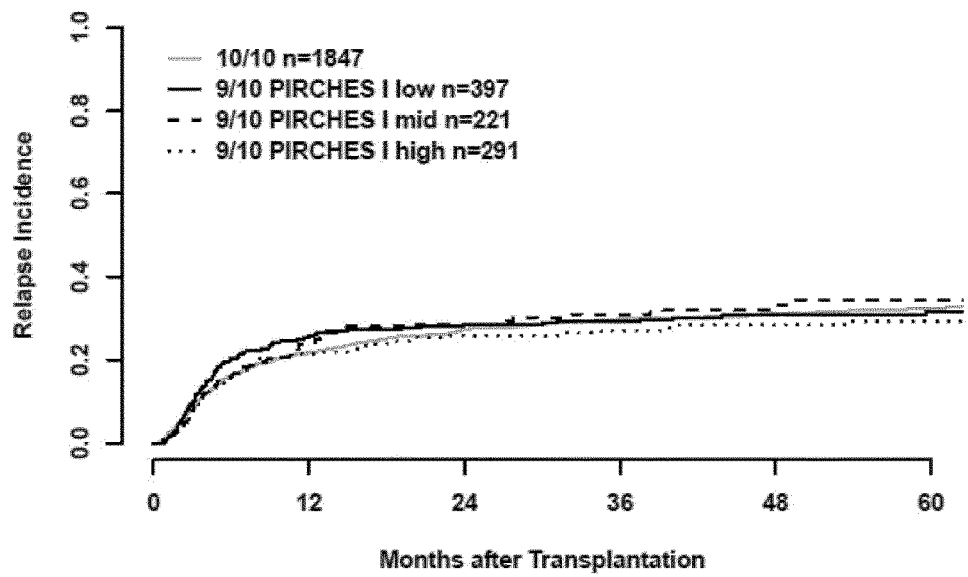
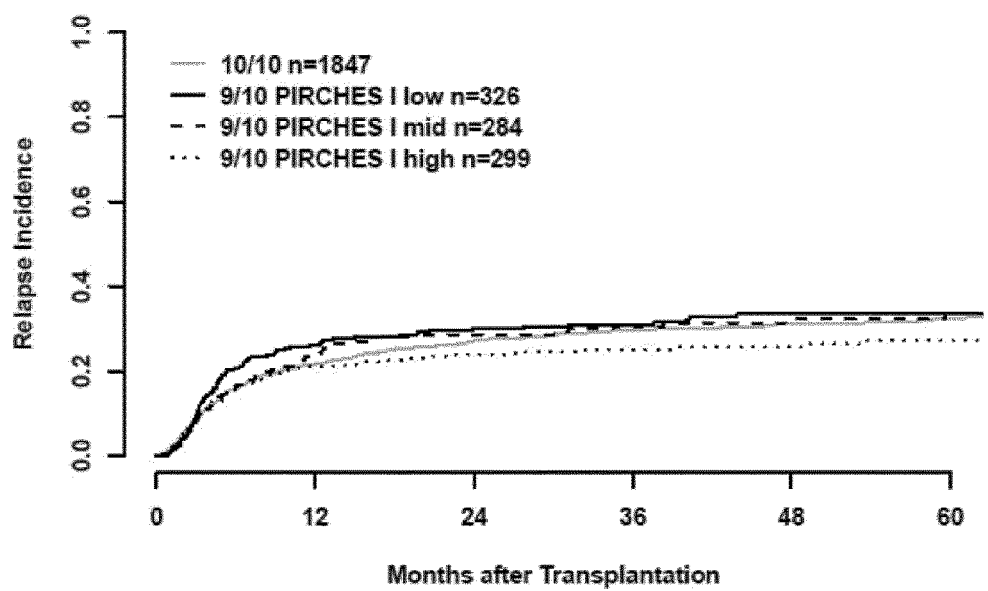

METHOD FOR PREDICTION OF AN IMMUNE RESPONSE AGAINST MISMATCHED HUMAN LEUKOCYTE ANTIGENS

CROSS-REFERENCE TO RELATED APPLICATIONS

This is the U.S. national stage of International application PCT/EP2013/073386, filed Nov. 8, 2013 designating the United States and claiming priority to European applications EP 12075124.3, filed Nov. 8, 2012, EP 12075125.0, filed Nov. 8, 2012, EP 12194008.4, filed Nov. 23, 2012, EP 13075011.0, filed Jan. 24, 2013 as well as the benefit of U.S. applications US 61/724,103, filed Nov. 8, 2012 and US 61/729,440, filed Nov. 23, 2012.

The invention relates to a method for prediction of an immune response against human leukocyte antigens (HLA) after transplantation, said method comprising HLA-typing of the donor and/or donor material and recipient to determine HLA-mismatches and determination of the number of predicted indirectly recognized HLA epitopes (PIRCHES). The invention therefore provides methods for selecting and/or screening donor material for allogeneic transplantation, for example for selecting donor material with permissible mismatches from mismatched, preferably unrelated donors. In preferred embodiments the method relates to pre-transplantation prediction of an unwanted alloreactivity that could occur after transplantation of allogeneic stem cells, independent of origin, hematopoietic stem cells, cord blood, kidneys and/or other cells, tissues or organs.

BACKGROUND OF THE INVENTION

Transplantation of allogeneic cells, tissues and organs is an evolving therapy that has become an increasingly attractive therapeutic option. The number of patients receiving transplants from unrelated donors is expected to double in the near future. Alloreactivity after transplantation has a major impact on clinical outcome, with pathological as well as beneficial effects. HLA mismatches are known to induce an immune reaction after transplantation, however the factors involved in predicting risk of unwanted immune reaction are not well understood.

Hematopoietic Stem Cell Transplantation

Hematopoietic Stem Cell Transplantation (HSCT) is one example of a quickly growing therapeutic option. The major limiting factor of HSCT remains graft-versus-host disease (GVHD), and since the number of patients receiving HSCT is expected to increase, the provision of novel approaches to prevent GVHD must be accelerated. To overcome the risk of GVHD, patients are preferably transplanted with a donor that is completely matched for all HLA-alleles. However, due to diversity of HLA molecules in the population, these completely matched donors are not available for approximately 40% of patients. When a completely matched donor is not available, a clinician often has to face the difficult decision to choose the best donor out of the mismatched donors (i.e. the one that carries the lowest GVHD risk). Until now, determining which donor is most suitable relies on a laborious assay that requires up to 14 days of labwork.

Historically, alloreactivity after HSCT is considered to be evoked mostly due to direct recognition of HLA disparities by donor T cells. This means that the graft T cells recognize mismatched HLA that is expressed as an intact molecule on the cell surface of host cells. The present invention is based in particular upon indirect recognition. Alloreactivity can be evoked when peptides derived from the mismatched host HLA allele are processed and presented on shared HLA and thereby recognized by the donor T cells.

Alloreactivity after hematopoietic stem-cell transplantation (HSCT) has a major impact on clinical outcome, with pathological as well as beneficial effects. The pathological effect of alloreactivity is reflected by graft-versus-host disease (GVHD). The risk of acute GVHD (aGVHD) is dependent on the level of matching for the HLA-A, -B, -C, -DRB1, and -DQB1 alleles, with an optimal match being a full match for five loci (a 10/10 match).

Recipients of matched-unrelated HSCT have a 24% reduced cumulative incidence of severe aGVHD compared to recipients of single mismatched donors (Ref 1a). Although recipients of 10/10-matched HSCT have a 47% increased hazard ratio (HR) for leukaemia relapse when compared to HSCT with donors mismatched for one HLA-C allele (Ref 2a), transplant protocols preferentially select 10/10-matched donors as overall survival is significantly inferior in partially matched-unrelated donors (Ref 1a). However, fully matched-unrelated donors are not available for all patients; in 40% of the situations, a single HLA-mismatched donor (a 9/10 match) is the best available alternative (Ref 3a).

In these situations, definition of the best-permissible mismatch may help prevent GVHD and, subsequently, inferior outcome. Recently, certain specific non-permissible mismatches have been identified on an epidemiological basis, in relation to an increased risk of developing severe aGVHD (Ref 4a). The mechanism underlying the increased risk of GVHD after HSCT with these non-permissible mismatches remains poorly characterised.

Functionally, better-permissible mismatches are determined with cytotoxic T-lymphocyte precursor frequency (CTLpf) assays. CTLpf above $1/10^5$ are predictive for developing severe aGVHD (Ref 5a). Moreover, CTLpf less than or equal to 1 per $10^6$ PBL is associated with a better overall survival. (Ref: Heemskerk et al (2007) Bone Marrow Transplantation, 40, 193-200) Thus, these criteria can be used to distinguish between the potentially mismatched donors. However, the CTLpf assay is laborious, delays time to transplantation, and is therefore not used in most transplant centres. Additionally, materials from potential donors need to be shipped and tested before use in transplantation. There are presently no effective means available for direct donor selection pre-delivery, based on eliminating samples which have a likelihood producing a negative result.

To find an alternative for the CTLpf assay, multiple, so far unsuccessful, attempts have been undertaken to predict non-permissible mismatches using two generally available prediction programs, HLAMatchmaker and HistoCheck. HLAMatchmaker determines potential epitopes for antibodies and has proven its validity for solid-organ transplantation (Ref 6a, 7a). HLAMatchmaker considers differences in amino-acid triplets as epitopes on HLA. Although antibodies potentially play a role in the development of GVHD, predictions based on HLAMatchmaker are not correlated to alloreactivity (Ref 1a). HistoCheck is based on the concept of direct recognition of HLA disparities, that is, donor T cells recognize an intact mismatched-HLA molecule loaded with a non-polymorphic peptide (Ref 9a). HistoCheck determines the structural differences in HLA molecules in the peptide-binding grooves or regions contacting the T-cell receptor (Ref 10a). By determining these structural differences, it aims to predict the likelihood of direct recognition of HLA disparities. Dissimilarity scores obtained with HistoCheck are also not correlated to alloreactivity (Ref 11a, 12a).

In light of the previously existing techniques there exists a need for more reliable methods for predicting whether donor material for a transplantation, which is HLA mismatched, is at increased risk of leading to a failed transplantation, for example development of GVHD, and/or an increase in mortality.

Kidney Transplantation

Matching for human leukocyte antigens (HLA) significantly improves the outcome of kidney transplantation (reviewed in Ref 1b). However, as a result of the high level of polymorphism of the various HLA loci and the limited number of donors, HLA mismatches between donor and recipient exist in approximately 85% of cadaveric kidney transplantations (Eurotransplant database; http://www.eurotransplant.org, accessed Apr. 24, 2012). Evidently, these HLA mismatches frequently lead to production of HLA-specific antibodies, which shorten graft survival (Ref 2b) and reduce the re-transplantation options. In order to prevent antibody formation against HLA, the optimal kidney grafts are either HLA identical to the recipient, or express acceptable HLA mismatches which do not induce antibody formation. To a limited extent, these acceptable mismatches can be identified with the HLAMatchmaker algorithm.

HLAMatchmaker defines polymorphic epitopes on HLA molecules, called eplets, accessible by HLA antibodies and subtracts those eplets present on the patients' own HLA (Ref 3b, 4b). In case this leaves no eplets to be recognized on a kidney graft, no antibody responses are to be expected (Ref 5b). Although HLAMatchmaker predicts which HLA-antigens can potentially induce HLA antibody formation, it does not predict T-cell reactivity towards allogeneic HLA (Ref 6b).

In previous studies it has been shown that the HLA-DR phenotype of the responder influences the production of Bw4-specific antibodies and class-I antibody sensitization grade (Ref 7b, 8b). This suggests a role for indirect recognition of donor-derived HLA peptides on HLA class-II molecules of the antigen-presenting cells of the patient. This phenomenon would explain Thelper-2-cell responses leading to the production of donor-specific antibodies (DSA) of the IgG isotype (Ref 9b).

Binding of Peptides to HLA Molecules

Binding of peptides to HLA molecules is predictable. The differences between predicted binding affinities and experimental measurements have been shown to be as small as the differences in measurements between different laboratories (Ref 10b). Predictability is particularly high for HLA class-I molecules, as these molecules have a more strict preference for nine amino acid long peptides (9-mers) and require specific amino acids as anchor residues at clearly defined anchor positions (Ref 11b). For HLA class II molecules predictability is lower, as peptides of different length can bind using different positions as anchor residues (Ref 12b). Therefore, it is difficult to determine how a peptide aligns to the HLA class II-binding groove and which amino-acid residues in the peptide are preferred as anchors. To solve this problem, Nielsen et al. used a so-called core predictor to estimate how a peptide positions in the class II binding groove (Ref 23a). The core predictor enabled the development of an accurate HLA class-II predictor, called NetMHCII (Ref 24a).

Despite the advances in predicting peptide binding to class I and class II HLA molecules, there is still significant uncertainty in assessing the factors involved in alloreactivity and the production of donor-specific antibodies (DSA). Considering the tools presently available to predict unwanted immune responses after kidney transplantation, there exists a need to provide more reliable methods for assessing potentially adverse reactions in advance of transplantation.

Indirect Recognition of Mismatched-HLA Antigens

Conceptually, mismatched HLA-directed T-cell alloreactivity may result from direct and indirect recognition of HLA disparities. So far, studies that aimed at explaining and predicting the clinical alloreactivity towards mismatched HLA, mainly focused on direct recognition of HLA disparities. Direct recognition involves donor T cells that recognize an intact mismatched-HLA molecule loaded with a non-polymorphic peptide (Ref 9a). When polymorphisms in HLA alleles lead to differences in the peptide-binding groove, the presented peptide repertoire of HLA molecules may differ substantially. These different peptide repertoires may lead to T-cell responses. The HistoCheck algorithm determines structural differences in HLA molecules in the peptide-binding grooves or regions contacting the T-cell receptor, thereby predicting a dissimilarity score (Ref 10a). However, the scores obtained with HistoCheck do not correlate with alloreactivity, neither in vitro (Ref 6c), nor in vivo (Ref 7c, 11a, 12a).

T-cell related alloreactivity can potentially also be evoked by indirect recognition of the mismatched-HLA allele. Indirect recognition has been studied in great detail for minor histocompatibility (H) antigens. Mismatches for these HLA-presented polymorphic proteins are associated with an increased risk of aGVHD (Ref 13a), and a decreased risk of relapse (Ref 14a, 15a). Analogous to peptides derived from minor H mismatches, peptides derived from mismatched-HLA molecules can also be presented by HLA.

Indirect recognition of the mismatched-HLA antigen may lead to T cell-related alloreactivity. During indirect HLA recognition, T cells recognize peptides derived from polymorphic HLA antigens presented by a shared (matched) HLA molecule. Peptides derived from mismatched-HLA molecules are frequently presented by HLA (Ref 10c). These indirectly recognizable HLA epitopes have been associated with both acute and chronic graft failure in solid organ transplantation (Ref 11c, 12c, 13c, 14c). T cells that indirectly recognize HLA-mismatches in the context of self-HLA may therefore play an important role in clinical alloreactivity.

With approximately 8800 HLA alleles identified today (Ref 15c), experimentally determining all potential HLA-derived epitopes presented in all HLA antigens is an extensive and hardly possible task. To facilitate the identification of these indirectly recognizable HLA epitopes, a novel approach has been developed. This approach is based on validated prediction tools (Ref 18a, 19a, 21a, 20a, 20c).

The present invention designates the HLA-derived epitopes that are predicted to be presented as Predicted Indirectly ReCognizable HLA Epitopes (PIRCHES). The present invention identifies PIRCHES presented by shared—HLA class-I (PIRCHE-I) and class-II (PIRCHE-II) separately. PIRCHE-II are shown to induce alloreactivity after kidney transplantation; PIRCHES presented by HLA-DR correlated with the de novo development of donor-specific HLA IgG antibodies (Ref 21c).

The present invention is therefore based on the finding that recognition of HLA-derived peptides has an effect on clinical alloreactivity after HLA-mismatched HSCT. To this end, numbers of predicted PIRCHE-I and -II can be assessed and their role evaluated in the adverse clinical effects of HSCT. On the basis of such investigation, the present invention describes universally applicable methods that can predict non-permissible HLA mismatches prior to HSCT and other cell or organ transplants.

SUMMARY OF THE INVENTION

In light of the prior art the technical problem underlying the present invention is the provision of means for prediction of an unwanted immune response in patients undergoing transplantation procedures, the prediction of therapeutic outcome of a transplantation (such as survival, GVHD, relapse, engraftment, graft rejection) or further means for selecting donor cells or tissue preparations suitable for allogeneic transplantation with a low risk of adverse reaction.

This problem is solved by the features of the independent claims. Preferred embodiments of the present invention are provided by the dependent claims.

The invention therefore relates to a method for prediction of an immune response against human leukocyte antigens (HLA) after transplantation, wherein said immune response is associated with HLA-mismatches between donor and recipient, said method comprising:
  HLA-typing of the donor and/or donor material and recipient to determine HLA-mismatches, and
  determination of the number of predicted indirectly recognized HLA epitopes (PIRCHES), wherein said PIRCHES are recipient- or donor-specific HLA-derived peptides from the mismatched recipient-HLA allele and are predicted to be presented by a shared (matched) HLA molecule,
  wherein the number of PIRCHES correlates with the likelihood of said immune response.

The method therefore provides preferably means for pre-transplantation prediction of the risk or likelihood of occurrence of an unwanted immune response against human leukocyte antigens (HLA), which could occur after transplantation. The HLA-typing of the method may have been carried out in advance and the data regarding HLA-type subsequently analysed via the method of the present invention.

According to the present invention, the PIRCHES are typically recipient-specific peptides in cases of HSCT and GVHD, GVL and reduced survival, whereas the PIRCHES may be donor-specific in cases of graft rejection, after organ or tissue transplantation.

The approaches of the prior art, such as HLAMatchmaker, which assesses the degree of structural compatibility between mismatches (Ref 8a), have not provided effective means for predictive determination of the risk of an unwanted immune reaction. HLAMatchmaker considers the structural basis of epitopes on HLA-antigens that could induce HLA-antibodies. It does so by looking at HLA class I antigens as a combination of short sequences (triplets), and determining the differences in these triplets. The degree of triplet mismatching did not significantly correlate to aGVHD. An additional method of the prior art, HistoCheck, the method evaluated by Spellman and Askar and colleagues (Ref 11a, 12a), rates the amino acid differences between HLA-allelic products based on the position within the HLA molecule and the functional similarity of amino acids within proteins. The Dissimilarity Scores that were obtained with this ranking system did not predict aGVHD.

Since the previous attempts with computational methods were unable to predict GVHD, the method of the present invention is the first computer implemented method that provides improved donor selection for HSCT with a reliable and effective pre-transplantation prediction of an unwanted and potentially dangerous immune response. Furthermore, while the previous attempts were undertaken with approaches that mostly asses the structural/functional dissimilarity between HLA molecules (i.e. are based on direct recognition of HLA disparities or the possibility of recognition via antibodies) the present invention preferably is based on predicted indirect recognition of HLA mismatched molecules. The method of the present invention is surprisingly suitable to predict alloreactivity, which was not possible before. The invention therefore is based on a surprising and unexpected principle, that the number of predicted indirectly recognizable HLA epitopes (PIRCHES) correlates with the likelihood of an unwanted immune response post-transplantation. No indication has been provided in the prior art that such a relationship exists.

The present invention therefore represents the technical utilisation of the relationship between risk of alloreactivity and increased numbers of mismatched HLA-derived peptides presented by shared-HLA molecules. These numbers can be determined preferably in silico and can be used as a predictive marker with respect to the development of alloreactivity, for example GVHD.

The present invention provides a preferably computer implemented method that determines which donor is suited for transplantation when a completely matched donor is not available, without the need for laborious compatibility assays. The present invention for example is applicable to multiple transplant settings, such as stem cells, cord blood cells or solid organ transplantation, amongst others. Essentially any transplantation, in which HLA-matching plays a role in determining alloreactivity or tissue rejection after transplantation, is encompassed by the present invention.

Considering the enormous health cost to patients having suffered from unwanted immune responses after transplantation, methods for the prediction of safely transplantable material are of paramount importance to the medical community. The method as described herein enables reduction of risk upstream of surgery (or treatment), thereby avoiding substantial health and financial cost to patients, medical practitioners and institutions, respectively.

In one embodiment the invention therefore relates to a method for prediction of an immune response against human leukocyte antigens (HLA) associated with, preferably induced by, HLA-mismatches between donor and recipient after transplantation, wherein HLA-typing for the donor and recipient is conducted, at preferably high resolution level with sequence based typing, to determine the mismatches, the number of predicted indirectly recognized HLA epitopes (PIRCHES) is identified using computer-implemented methods by determining the presentation and/or binding of peptides derived from mismatched recipient and/or donor HLA alleles, whereby the number of PIRCHES correlates with the likelihood of said immune response.

In one embodiment the present invention relates to a method as described herein, wherein said transplantation comprises haematopoietic stem-cell transplantation (HSCT).

In one embodiment the present invention relates to a method as described herein, wherein said transplantation comprises cord blood or cord blood cell transplantation.

In one embodiment the present invention relates to a method as described herein, wherein said transplantation comprises kidney transplantation.

The method of the present invention may also be applied for prediction of an unwanted immune response in the context of other medical disorders, such as secondary recurrent miscarriage, antibody formation during pregnancy, or for assessing risk before cornea transplantation.

In one embodiment the present invention relates to a method as described herein, wherein said immune response comprises an unwanted alloreactivity.

In one embodiment the present invention relates to a method as described herein, wherein said immune response comprises a wanted alloreactivity, whereby a wanted alloreactivity can be an anti-leukemic alloreactivity.

In one embodiment the present invention relates to a method as described herein, wherein said immune response comprises a T-cell-mediated response. In one embodiment the present invention relates to a method as described herein, wherein said immune response leads to acute graft versus host disease (aGVHD) or chronic graft versus host disease (cGVHD).

In one embodiment the present invention relates to a method as described herein, wherein said immune response comprises an antibody-mediated response. As is shown in the experimental examples below, HLA molecules against which antibodies are formed, have a statistically higher number of PIRCHES.

In one embodiment the present invention relates to a method as described herein, wherein the likelihood of said immune response is increased with an increase in the number of PIRCHES. As is described extensively in the examples of the application, patients with high numbers (>2) of peptides presentable by HLA class I compared to patients with low numbers (≤2), developed aGVHD significantly earlier (example 1). Patients suffering from extensive cGVHD displayed a trend for higher numbers of peptides presentable by HLA class I and II combined and by HLA class I and II separately, as compared to those with no or limited cGVHD. Extensive cGVHD developed earlier in the patients that were predicted to present high numbers of peptides on HLA class I and II combined compared to low numbers. Patients with both low PIRCHE-I and PIRCHE-II values showed the lowest risk estimates, similar to 10/10 matched transplantations. Especially donor-recipient combinations in the low PIRCHE-I group are favourable: these combinations have a significantly increased probability of survival and disease-free survival, and show a decreased risk of acute and chronic GvHD compared to patients in the higher PIRCHE-I groups. These results represent an entirely unprecedented and unexpected technical effect. Through the present method, mismatched donors may be selected that provide essentially the same low risk of unwanted immune responses as HLA-matched donors.

The computer implementation of the invention enables an efficient, fast and reliable method for identification of potentially permissible donor material for allogeneic transplantation. The data processed by the software can be handled in a completely or partially automatic manner, thereby enabling in a preferred embodiment an automated computer-implemented method. Data regarding the HLA typing of donor and recipient, in addition to the number of PIRCHES determined for any donor-recipient pair, can be stored electronically and maintained in appropriate databases. The invention therefore also relates to computer software capable of carrying out the method as described herein. The invention further relates to a preferably automated computer-implemented method for prediction of an immune response against human leukocyte antigens (HLA) after transplantation.

The system preferably comprises a database with information on all published HLA alleles. The database may be updated as new HLA allele sequences are published. Computer software, preferably based on PERL, but which could also be based on other computing languages, can be used for generating and/or updating the databases, in addition to calling the respective programmes required for assessing the number of PIRCHES (for example NetChop, NetMHC, etc. . . . ).

The invention further comprises a system for preferably pre-transplantation prediction of an immune response against human leukocyte antigens (HLA), which may occur after transplantation, wherein said immune response is associated with HLA-mismatches between donor and recipient, said method comprising HLA-typing of the donor and/or donor material and recipient to determine HLA-mismatches, and determination of the number of predicted indirectly recognized HLA epitopes (PIRCHES), wherein said PIRCHES are recipient- or donor-specific HLA-derived peptides from the mismatched recipient-HLA allele and are predicted to be presented by a shared (matched) HLA molecule, wherein the number of PIRCHES correlates with the likelihood of said immune response. The system may comprise computing devices, data storage devices and/or appropriate software, for example individual software modules, which interact with each other to carry out the method as described herein.

In one embodiment the system may comprise databanks or databases of a cord blood bank, whereby each sample is tested for HLA-type, and the information stored electronically. The system may also comprise a connection between an additional computing device, for example a device of a clinician, transplant centre, or hospital, in which the HLA-type data for the recipient is stored. Through a connection between the two databases, for example over the internet, the method of the invention can be carried out using appropriate software. HLA-types of multiple potential donor samples and the patient may be compared and the number of PIRCHE for any given donor-recipient pair determined. In light of the analysis based on the method described herein a clinically relevant prediction can be made whether any given donor material, for example those samples stored in a cord blood bank or other cell or tissue bank, is suitable for transplantation. The invention also relates to a software suitable for carrying out the method described herein.

In one embodiment the method of the invention therefore comprises comparison of data regarding HLA-typing from the recipient with multiple potential donor samples, in order to identify suitable transplantation material.

The invention therefore relates to a method for selecting and/or screening donor material for allogeneic transplantation with acceptable mismatches based on a prediction of an immune response against human leukocyte antigens (HLA) after transplantation, wherein said immune response is associated with HLA-mismatches between donor and recipient, said method comprising: comparison of the HLA-types of multiple donor samples to the HLA-type of the recipient, in order to determine HLA-mismatches, and determination of the number of predicted indirectly recognized HLA epitopes (PIRCHES) for each donor-recipient pair, wherein said PIRCHES are recipient- or donor-specific HLA-derived peptides from the mismatched recipient-HLA allele and are predicted to be presented by a shared (matched) HLA molecule, wherein the number of PIRCHES correlates with the likelihood of said immune response.

In one embodiment the HLA-typing of the donor and/or recipient may have been carried out in advance of the planned transplantation and the corresponding data relating to HLA-typing of any given donor material may preferably be stored in an appropriate computer storage and/or computing medium, such as a database and/or databank, which can be accessed by appropriate software. Such a database may be a stem cell database, cord blood database or tissue or organ database, for example a centralised or local storage of data relating to potential donor material. Upon medical diagnosis of a condition treatable by any given transplantation, HLA-typing of the patient (recipient) may be carried out (if not already carried out) and the results of the HLA-typing compared to the data stored for the potential donor material. Such comparison may be carried out by standard software.

Upon identification of HLA-matched material the transplantation could be conducted. In cases where material is identified in which HLA-mismatches between the donor and recipient are evident, the permissibility of the mismatches can be ascertained by application of the method or system of the present invention to any given or all possible donor-recipient pairs. Appropriate software, capable of carrying out the determination of the number of PIRCHES, may be applied for any given donor-recipient pair and, on the basis of the number of PIRCHES, the permissibility of the HLA-mismatch assessed, preferably automatically.

Particularly for HSCT, there are two options regarding searching:
1) Identify a number of potentially matched donors, type said potentially matched donors and determine whether they have a certain mismatch, followed by selecting the best (most permissible) one based upon the analysis of PIRCHES, and/or
2) Identify a certain patient as being difficult or impossible to fully match, run the PIRCHE algorithm on the likely alternatives/mismatches, and subsequently call for samples from potential donors that have low PIRCHES.

In one embodiment the present invention relates to a method as described herein, wherein said recipient- or donor-specific HLA-derived peptides from the mismatched recipient-HLA allele are identified by a computer-implemented method for identifying the cleavage sites (endopeptidase and/or protease sites) of the human proteasome. A preferred embodiment of this feature of the invention relates to the use of the software NetChop, or alternative software as described herein, which is capable of determining proteasome cleavage of peptide sequences.

In one embodiment the present invention relates to a method as described herein, wherein said presentation of peptides by a shared (matched) HLA molecule is determined by a computer-implemented method for predicting the binding of said peptide to any given HLA molecule. A preferred embodiment of this feature of the invention relates to the use of the software NetMHCpan and/or NetMHCII, or other alternatives as described herein, which are capable of determining (or predicting) the binding of any given, preferably nonameric, peptide in HLA or MHC molecules.

The proteasome cleavage prediction and HLA-binding prediction may be carried out in software designed to incorporate both modules in sequence, in order to provide an automatic determination of the number of PIRCHES.

The method of the invention may be carried out in such a manner, that peptides of any length including or between 5-20, preferably 8-15, more preferably 9-10 amino acids, may be identified and considered as PIRCHES. In a preferred embodiment the present invention relates to a method as described herein, wherein said PIRCHES nonameric (9 amino acid) peptides.

In one embodiment the present invention relates to a method as described herein, wherein said PIRCHES are presented by shared HLA class I (PIRCHE I) or by shared HLA class II (PIRCHE II).

In one embodiment the present invention relates to a method as described herein, wherein PIRCHE-I peptides have a predicted IC50 binding value of ≤10 µM, preferably ≤1000 nM, more preferably ≤500 nM.

In one embodiment the present invention relates to a method as described herein, wherein PIRCHE-II peptides have a predicted IC50 binding value of ≤20 µM, preferably ≤5 µM, more preferably ≤1000 nM.

Other binding criteria may be applied for predicting whether a peptide will be presented by the HLA molecule. The provided values are based upon binding properties previously described in the literature, but different values may be derived or applied, if the PIRCHE can be reasonably be considered to bind and even customize it per presenting HLA. The current values are what we used in the present studies and seem to work well, though.

For each donor-recipient pair, presentable recipient- or donor-specific HLA-derived peptides (PIRCHES) are identified. PIRCHE-I may preferably be identified in two steps:
1) In silico assessment of predicted processing of the amino acid sequences by the proteasome and transportation via the TAP channel is carried out, preferably using NetChop. NetChop is a commonly known software-based method for identifying the cleavage sites of the human proteasome based on sequence analysis. Nonameric peptides are preferably included in the analyses.

In a preferred embodiment, the C-terminal cleavage potential is determined. The entire HLA protein is cleaved (preferably in silico) and all positions that are cleavable are marked. From the marked positions backwards, preferably nonameric peptides are identified that are analyzed for binding to class I.

As alternatives to NetChop a variety of software-based approaches are known in the art that could be applied, such as MAPP, PaProc or those methods described in Lu et al (J Zhejiang Univ Sci B, 2013 September; 14(9):816-28) or Ginodi et al (Bioinformatics, 2008 Feb. 15; 24(4):477-83).
2) Subsequently, peptides with a high probability of being processed (according to step 1) are tested for their capacity to be presented by HLA that are shared (matched) between the donor and recipient (preferably HLA-A, -B and -C) using NetMHCpan. NetMHCpan is a commonly known method for identifying and/or predicting the binding of peptides to any known MHC molecule using artificial neural networks. The method is trained on more than 150,000 quantitative binding data covering more than 150 different MHC molecules. Predictions can be made for HLA-A, B, C, E and G alleles. The prediction values can be given in nM IC50 values, or as %-Rank to a set of 200000 random natural peptides. Preferably peptides with IC50 binding values ≤500 nM are chosen as relevant binders.

PIRCHE-II may be identified as follows:
Preferably nonameric binding cores of potential 15-meric HLA-DR, -DQ, and -DP binders may preferably be analysed with NetMHCIIPan 2.0, NetMHCII 1.0, or NetMHCII 2.2. NetMHCII is a commonly known method for predicting binding of peptides to HLA-DR, HLA-DQ, HLA-DP and mouse MHC class II alleles using artificial neuron networks. Predictions can be obtained for 14 HLA-DR alleles covering the 9 HLA-DR supertypes, six HLA-DQ, six HLA-DP, and two mouse H2 class II alleles. The prediction values are given in nM IC50 values, and as a %-Rank to a set of 1000000 random natural peptides. Peptides with IC50-binding values ≤1000 nM are considered as relevant.

There are a number of alternative methods known in the art, which could be used for determination of HLA binding. SYFPEITHI (based on methods described in Rammensee et al. Immunogenetics 41, 178-228, 1995 and Rammensee et al, Landes Bioscience 1997) and BIMAS are well-known alternatives and are appropriate for class I binding but show some drawbacks in class II binding. Other alternatives relate to Tepitope (based on Sturniolo et al, 1999, Nat. Biotechnol. 17:555-561), TepitopePAN, EpicCapo, PAAQD, POPI, Propred and Multipred.

In one embodiment, per presenting shared-HLA allele, predicted binders derived from donor-HLA alleles are regarded as donor-self peptides, and recipient-HLA alleles regarded as recipient-self peptides, depending on the therapeutic setting, and thus excluded from the analyses. In general, for each donor-recipient pair, the number of presentable recipient- or donor-specific peptides (derived from the mismatched recipient-HLA allele and predicted to be presented by shared HLA) is counted in order to generate the number of PIRCHES.

In one embodiment the present invention relates to a method as described herein, wherein HLA typing is carried out on HLA subtypes HLA-A, HLA-B, HLA-C, HLA-DRB1, HLA-DQB1, HLA-DPB1, -DQA1, -DPA1, -G, -E, -F, MICA, MICB and/or KIR.

In one embodiment the present invention relates to a method as described herein, wherein HLA typing is carried out on HLA-A, -B, -C, -DRB1 and -DQB1. These 5 alleles provide the basis for the commonly used terminology "9/10-matched", which refers to a 9/10-matched unrelated donor. In such a case 9 of the 10 alleles of these 5 genes show a match but one remaining allele does not match. The present invention therefore allows, in a preferred embodiment, determination of whether the use of material from such a 9/10-matched unrelated donor is safe, i. e. whether the mismatch is permissible for transplantation.

The invention relates also to the method as described herein for finding permissible HLA-mismatches in donor samples where more mismatches are present than the common 9/10 scenario. One example of potential donors who are encompassed by the present invention are Haploidentical donors, who may be screened using the method described herein for permissible mismatched donor material. A haploidentical related donor, may be described as a donor who has a "50% match" to the patient. This type of donor can be a parent, sibling, or child. By definition, a parent or child of a patient will always be a haploidentical donor since half of the genetic material comes from each parent. There is a 50% chance that a sibling will be a haploidentical donor. Haploidentical HSCT offers many more people the option of HCT as 90% of patients have a haploidentical family member. Other advantages include: immediate donor availability; equivalent access for all patients regardless of ethnic background; ability to select between multiple donors; and ability to obtain additional cells if needed. Alternatively, cord blood units (CBUs) may not show a high level of HLA-matching, but still be suitable for transplantation if the mismatches are permissible as determined by the method as described herein. CBU's are typically minimally 4/6 matched, but this match can however lead to a 4/10 or 5/10 situation at the allelic level.

Considering that the method as described herein relies to some extent on shared HLA, the minimum HLA-match is one allelic match. Although this is unlikely to occur for HSCT, such a scenario will frequently arise for organ transplantation, due to the limited number of donor material available. The invention may therefore be carried out on mismatched samples with a minimum of one allelic match. The mismatched donor may therefore relate to a 1/10, 2/10, 3/10, 4/10, 5/10, 6/10, 7/10, 8/10, 9/10 or 10/10 (DP mismatch) match. If additional alleles are tested, the donor may also show any other kind of mismatch, whereby at least one allelic match is present. Preferred for the transplantation are donors with significant HLA-matches. If additional alleles are subjected to typing the donor could therefore be for example 11/12- or 13/14-matched.

In one embodiment the present invention relates to a method as described herein, wherein HLA typing comprises serological and/or molecular typing. In a preferred embodiment the present invention relates to a method as described herein, wherein HLA typing is carried out at high resolution level with sequence-based typing.

In one embodiment the present invention relates to a method as described herein, wherein HLA typing comprises sequencing of exon 1-7 for HLA class I alleles and exon 1-6 for HLA class II alleles. In one embodiment the present invention relates to a method as described herein, wherein HLA typing comprises high resolution HLA-A, -B, -C, -DRB1 and -DQB1 typing of exons 2 and 3 for HLA class-I alleles and exon 2 for HLA class-II alleles. These particular HLA-typing approaches are described in the examples provided herein and demonstrate advantages over earlier typing methods, providing full coverage of the alleles that need to be typed to identify the mismatches.

The method of the present invention may in principle be carried out on any given polymorphic protein (or corresponding gene coding for said polymorphic protein) in the human proteome/genome. In a further aspect of the invention a method is provided for prediction of an immune response against any given polymorphic protein after transplantation, wherein said immune response is associated with a difference in polymorphic proteins between donor and recipient, said method comprising:
  identification of polymorphic proteins between the donor and recipient, for example via nucleic acid sequencing of genomic regions known to carry potentially immunologically relevant polymorphs and/or whole genome sequencing via preferably "next-generation" sequencing technology (e. g. 454 pyrosequencing, Illumina (Solexa) sequencing, SOLID sequencing), and
  determination of the number of predicted indirectly recognized epitopes, wherein said epitopes are recipient- or donor-specific polymorph-derived peptides from and are predicted to be presented by an HLA molecule,
  wherein the number of epitopes correlates with the likelihood of said immune response.

According to this aspect of the invention, whole genome sequencing could be carried out on a cohort of HLA-identical sibling transplantations and identify all polymorphisms between donor and recipient, genome wide. All these polymorphisms would then be used to generate a database similar to the databases described for HLA mismatches, using the herein described approach. Then the immunological matching scores would be calculated via analogous computing approaches and analysed for clinical outcome.

The invention further relates to a method for prediction of therapeutic outcome of a transplantation comprising the method as described herein. In a preferred embodiment the therapeutic outcome is selected from the group consisting of patient survival, disease free survival and transplant-related mortality. As is demonstrated in the examples herein, the PIRCHE number correlates well with therapeutic outcome after transplantation. According to these embodiments not only the success of transplantation as such, but also the associated therapeutic benefit of the specific treatment can be ensured by performing the method of the invention, for example pre-screening of potential donor material, as described herein.

The invention therefore further relates to a method for selecting a cell or tissue preparation for allogeneic transplantation comprising the method as described herein. The method preferably relates to a method for selecting and/or screening donor material for allogeneic transplantation for acceptable mismatches. The method of the invention represents a computer-implemented procedure that has a direct relevance for the health and safety of transplantation recipients.

In a preferred embodiment the present invention relates to a method as described herein, wherein donor material for allogeneic transplantation originates from a donor with at least one allelic match.

In a preferred embodiment the present invention relates to a method as described herein, wherein donor material for allogeneic transplantation originates from a donor with 10/10 matches and an HLA-DP mismatch. HLA-DP is a locus known as relevant for transplantation-related immune responses, and has been previously associated with GVHD. It is possible that in patients with 10/10 matches; an HLA-DP mismatch is present. The present invention can also be used to assess the PIRCHE derived from the HLA-DP mismatch.

In a preferred embodiment the present invention relates to a method as described herein, wherein donor material for allogeneic transplantation originates from a 9/10-matched unrelated donor.

In one embodiment the present invention relates to a method as described herein, wherein donor material for allogeneic transplantation is associated with a low risk of an unwanted immune response when the number of PIRCHE-I $\leq 3$, preferably $\leq 2$, more preferably $\leq 1$. As is demonstrated in the examples herein, these values of PIRCHE number correlate significantly with reduced frequency of unwanted immune response post-transplantation.

There has been no suggestion in the art that a threshold exists for an "acceptable number" of such peptides. This aspect of the invention, in addition to the further embodiments that are defined by specific values indicative of safe or unsafe donor material, enable complex biological phenomena to be assessed in the form of a simple "yes-no" read-out, thereby providing feedback to the end-user of the method whether any given donor material is suitable. This subsequently enables a completely automated approach towards interrogating databanks comprising HLA typing data, and a method in which a clear indication is provided whether material from a preferably 9/10-mismatch donor may be relatively safe for application.

In one embodiment the present invention relates to a method as described herein, wherein donor material for allogeneic transplantation is associated with a low risk of an unwanted immune response when the number of PIRCHE-II $\leq 4$, preferably $\leq 3$, more preferably $\leq 2$. As is demonstrated in the examples herein, these values of PIRCHE number correlate significantly with reduced frequency of unwanted immune response post-transplantation.

In one embodiment the present invention relates to a method as described herein, wherein donor material for allogeneic transplantation is associated with a low risk of an unwanted immune response when the number of combined PIRCHE-I and PIRCHE-II $\leq 6$, preferably $\leq 4$, more preferably $\leq 2$. As is demonstrated in the examples herein, these values of PIRCHE number correlate significantly with reduced frequency of unwanted immune response post-transplantation.

The specific values for PIRCHE numbers associated with a risk of an unwanted transplantation are based on the analysis provided in the examples herein. According to the examples, the population was divided in tertiles, based on the assumption that there may not necessarily be linearity in the dose-response (ie the risk to PIRCHE ratio). Such a dose-response curve may be sigmoidal in nature or show some kind of plateau, thereby suggesting a tertile-based analysis. The specific values of PIRCHES provided herein may be considered as objective values, although these values represent preferred values which are not essential to the definition of the invention. In light of different stringencies applied to consideration of peptides with different lengths, or with different binding affinities for the HLA molecules, or in light of the number of loci or number of mismatches considered, these values may vary. In a preferred embodiment, the correlation between relatively high levels of PIRCHES with immune reactions, and low PIRCHE levels with permissible mismatches relates, to an objective representation of the invention. The method therefore also encompasses a relative assessment of the risk of an immune response, whereby when multiple potential donors are assessed; those donors with relatively lower numbers of PIRCHES compared to other donors are considered to be preferred for transplantation.

In one embodiment the present invention relates to a method as described herein, wherein HLA-DQB1 antigenic mismatches are interrogated. As shown in example 5, HLA-DQB1 antigenic mismatches, lead to the highest numbers of both PIRCHE-I and -II, thereby indicating that this allele in particular should be assessed when pre-screening potential mismatch donors for suitable transplantation material.

In one embodiment the present invention relates to a method as described herein for predicting the best donor out of multiple HLA-mismatched donors. In one embodiment the present invention relates to a method as described herein comprising additionally the analysis and comparison of multiple HLA-mismatched donors for the purpose of predicting alloreactivity between multiple donors, for example between two cord blood units and/or between a matched and an HLA-mismatched donor. As transplantation, especially of stem cells or cord blood, becomes a more reliable and preferred therapeutic option, at times multiple donor samples must be used in order to provide sufficient material for the transplantation. In light of this, the present method enables a "multi-donor" analysis, thereby comparing not only donor-recipient matches, but additionally or alternatively assessing donor-donor matches, in order to determine in advance of additional donor sample may be compatible with the recipient in addition to each other. The present method therefore enables fast and reliable "three-way" compatibility assessment without the complications of the laboratory-based methods of the past.

The method of the invention enables a number of beneficial technical and secondary effects. Through the method as presently described transplantations with allogeneic material may be carried out with essentially the same or similar low risk of an unwanted immune reaction. In light of this effect, the invention saves time due to the automated and/or computer-implementation, reduces health risk, reduces medical costs for potentially failed transplantations, increases the pool of possible donor material for any given recipient and enables previously untreatable patients (those for example have very rare HLA-alleles) to be treated with allogeneic material due to the risk reduction by selecting permissible mismatches.

DETAILED DESCRIPTION OF THE INVENTION

"Prediction" means a statement about possible events in the future. The term "forecast" may also be used. The "prediction" in the sense of the present invention represents an assessment of the likelihood or risk of an immune response occurring after transplantation. On the basis of the prediction, or risk assessment, valuable information is obtained in advance of a potentially harmful event, which can be used to determine further therapeutic options.

The term "Immune response" in the context of the present invention relates to an immune response as commonly understood by one skilled in the art. An immune response may be understood as a response from a part of the immune system to an antigen that occurs when the antigen is identified as foreign, which preferably subsequently induces the production of antibodies and/or lymphocytes capable of destroying or immobilising the "foreign" antigen or making it harmless. The immune response of the present invention may relate either to a response of the immune system of the recipient against the transplanted material, or an immune response effected by cells of the transplanted cells, tissues, or organs, whereby for example in GVHD T cells of the transplanted material react against and/or attack recipient antigens or tissue. The immune response may be a defence function of the recipient that protects the body against foreign matter, such as foreign tissue, or a reaction of immune cells of the transplanted material against recipient cells or tissue.

The human leukocyte antigen (HLA) system is the major histocompatibility complex (MHC) in humans. The super locus contains a large number of genes related to immune system function in humans. This group of genes resides on chromosome 6, and encodes cell-surface antigen-presenting proteins and has many other functions. The proteins encoded by certain genes are also known as antigens, as a result of their historic discovery as factors in organ transplants. The major HLA antigens are essential elements for immune function. HLAs corresponding to MHC class I (A, B, and C) present peptides from inside the cell (including viral peptides if present). These peptides are produced from digested proteins that are broken down in the proteasomes. In general, these particular peptides are small polymers, about 9 amino acids in length. Foreign antigens attract killer T-cells (also called CD8 positive- or cytotoxic T-cells) that destroy cells. HLAs corresponding to MHC class II (DP, DM, DOA, DOB, DQ, and DR) present antigens from outside of the cell to T-lymphocytes. These particular antigens stimulate the multiplication of T-helper cells, which in turn stimulate antibody-producing B-cells to produce antibodies to that specific antigen.

MHC loci are some of the most genetically variable coding loci in mammals, and the human HLA loci are no exception. Most HLA loci show a dozen or more allele-groups for each locus. Six loci have over 100 alleles that have been detected in the human population. Of these, the most variable are HLA-B and HLA-DRB1.

An allele is a variant of the nucleotide (DNA) sequence at a locus, such that each allele differs from all other alleles by at least one (single nucleotide polymorphism, SNP) position. Most of these changes result in a change in the amino acid sequences that result in slight to major functional differences in the protein.

"HLA" refers to the human leukocyte antigen locus on chromosome 6p21, consisting of HLA genes (HLA-A, HLA-B, HLA-C, HLA-DRB1, HLA-DQB1, etc. . . . ) that are used to determine the degree of matching, for example, between a recipient and a donor of a tissue graft. "HLA allele" means a nucleotide sequence within a locus on one of the two parental chromosomes. "HLA typing" means the identification of an HLA allele of a given locus (HLA-A, HLA-B, HLA-C, HLA-DRB1, HLA-DQB1, etc. . . . ). Gene sequencing may be applied. Samples may be obtained from blood or other body samples from donor and/or donor material and recipient, which may subsequently be analysed. In general, the sequence of the antigens determines the antibody reactivities, and so having a good sequencing capability (or sequence-based typing) obviates the need for serological reactions. Sequencing approaches to HLA-typing are preferred. Sequencing may relate to basic methods, such as Maxam-Gilbert sequencing, Chain-termination methods, advanced methods and de novo sequencing such as shotgun sequencing or bridge PCR, or the so-called "next-generation" methods, such as massively parallel signature sequencing (MPSS), 454 pyrosequencing, Illumina (Solexa) sequencing, SOLID sequencing, or other similar methods.

If serotyping is applied, different serotype reactions may indicate the need to sequence a person's HLA to determine the gene sequence. Allelic diversity makes it preferred to use broad antigen typing followed by gene sequencing because there is some increased risk of misidentifying by serotyping techniques. Phenotyping relates to a serological approach for typing which may be applied. Gene typing may alternatively or in combination be carried out. With this strategy, PCR primers specific to a variant region of DNA are used (called SSP-PCR). If a product of the right size is found, the assumption is that the HLA allele has been identified. PCR-SSO may also be used incorporating probe hybridisation. Reviews of technical approaches towards HLA typing are provided in Erlich H, Tissue Antigens, 2012 July; 80(1):1-11 and Dunn P, Int J Immunogenet, 2011 December; 38(6):463-73.

With respect to HLA typing, samples obtained from the donor themselves and/or from donor material before, during or after isolation/preparation for transplantation, may be used for HLA-typing and subsequent comparison to the HLA-typing data from the recipient. For example, HLA-typing of the donor themselves, for example by analysing a saliva, blood or other bodily fluid sample for HLA information, may occur, and optionally additionally or alternatively, the material obtained from the donor intended for transplantation (donor material) may be analysed for the same and/or complementary HLA type characteristics during HLA-typing.

An "HLA-mismatch" is defined as the identification of different alleles in donor and recipient, which are present at any given loci.

The donor is commonly understood to be an individual or multiple individuals (for example in the case of where multiple samples or preparations, such as cord blood units (CBUs) are required for an effective therapeutically relevant amount of donor material for the transplantation) who provide donor material, or in other words biological material, such as but not limited to cells, tissues, organs, or other bodily parts, fluids and/or preparations, for transplantation in the recipient. References to the donor, or HLA-typing of the donor, may also refer to donor material, or HLA-typing of the donor material, respectively.

The subject recipient of the method is typically a mammal, preferably a human. The recipient is typically a patient suffering from a disorder characterised by the need for transplantation, such as organ failure necessitating a transplant. By the term "organ", it is meant to include any bodily structure or group of cells containing different tissues that are organized to carry out a specific function of the body, for example, the heart, lungs, brain, kidney skin, liver, bone marrow, etc. In one embodiment the graft is an allograft, i.e. the individual and the donor are of the same species. The subject may also suffer from a condition that could be treated by the transplantation of cells, even when the disorder itself is not defined by a lack or loss of function of a particular subset of endogenous cells. Some disorders may be treatable by the transplantation of certain kinds of stem cells, whereby the native or endogenous pool of such cells are not necessarily non-functional in the recipient.

The method of the invention is particularly applicable to patients who are about to receive or are predicted to require a cell, tissue or organ transplant, to predict the likelihood of unwanted immune response, such as origin graft damage or rejection, and/or immune origin damage to non-graft tissue. For example, the patient may be expected to receive a transplant in the next one, two, three, four, five, six, or twelve months. Alternatively, the assay is particularly applicable to individuals who have received a transplant to predict the likelihood of immune origin graft damage or rejection, and/or immune origin damage to non-graft tissue. Post-transplant, the method is particularly applicable to patients who show evidence of chronic organ dysfunction (of the graft organ) or possible graft versus host disease (GVHD), particularly chronic GVHD and particularly in cases wherein the graft is a bone marrow transplant.

Transplantation is the moving of cells, tissue or an organ from one body (donor) to another (recipient or patient), or from a donor site to another location on the patient's own body, or from stored donor material to a recipients body, for the purpose of replacing the recipient's damaged or absent organ, or for the purpose of providing stem cells, other cells, tissues or organs capable of providing a therapeutic effect.

Allogeneic transplantation or Allotransplantation is the transplantation of cells, tissues, or organs, to a recipient from a genetically non-identical donor of the same species. The transplant is called an allograft, allogeneic transplant, or homograft. Most human tissue and organ transplants are allografts. Allografts can either be from a living or cadaveric source. Generally, organs that can be transplanted are the heart, kidneys, liver, lungs, pancreas, intestine, and thymus. Tissues include bones, tendons (both referred to as musculoskeletal grafts), cornea, skin, heart valves, nerves and veins. Worldwide, the kidneys are the most commonly transplanted organs, followed by the liver and then the heart. Cornea and musculoskeletal grafts are the most commonly transplanted tissues.

The invention also encompasses use of the method in the context of screening organs, cells, or tissues produced via regenerative medicine, for example reconstructed donor material that has been constructed ex vivo and is intended for transplantation. Stem cell technologies enable the production of a number of medically relevant cell types or tissues ex vivo. The present invention could therefore also be applied in screening allogeneic material that has been produced by biotechnological and/or tissue engineering methods for its suitability in transplantation.

The invention encompasses the assessment of risk of an immune reaction, preferably a pre-transplantation risk assessment, whereby any given stem cell may be considered as donor material intended for transplantation. For example, hematopoietic stem cell transplantation (HSCT) is the transplantation of multipotent hematopoietic stem cells, usually derived from bone marrow, peripheral blood, or umbilical cord blood. It is a medical procedure common in the fields of hematology and oncology, most often performed for patients with certain cancers of the blood or bone marrow, such as multiple myeloma or leukemia. In these cases, the recipient's immune system is usually destroyed with radiation or chemotherapy before the transplantation. Infection and graft-versus-host disease are major complications of allogenic (also referred to as allogeneic) HSCT.

Stem cells are to be understood as undifferentiated biological cells, that can differentiate into specialized cells and can divide (through mitosis) to produce more stem cells. Highly plastic adult stem cells are routinely used in medical therapies, for example in bone marrow transplantation. Stem cells can now be artificially grown and transformed (differentiated) into specialized cell types with characteristics consistent with cells of various tissues such as muscles or nerves through cell culture. Embryonic cell lines and autologous embryonic stem cells generated through therapeutic cloning have also been proposed as promising candidates for future therapies. The potential stem cell transplantation may relate to any given stem cell therapy, whereby a number of stem cell therapies exist. Medical researchers anticipate that adult and embryonic stem cells will soon be able to treat cancer, Type 1 diabetes mellitus, Parkinson's disease, Huntington's disease, Celiac disease, cardiac failure, muscle damage and neurological disorders, and many others.

Also known as somatic stem cells and germline stem cells, stem cells can be found in children, as well as adults. Pluripotent adult stem cells are rare and generally small in number but can be found in a number of tissues including umbilical cord blood. Bone marrow has been found to be one of the rich sources of adult stem cells which have been used in treating several conditions including Spinal cord injury, Liver Cirrhosis, Chronic Limb Ischemia and End-stage heart failure. Adult stem cells may be lineage-restricted (multipotent) and are generally referred to by their tissue origin (mesenchymal stem cell, adipose-derived stem cell, endothelial stem cell, dental pulp stem cell, etc.).

Multipotent stem cells are also found in amniotic fluid. These stem cells are very active, expand extensively without feeders and are not tumorigenic. Amniotic stem cells are multipotent and can differentiate in cells of adipogenic, osteogenic, myogenic, endothelial, hepatic and also neuronal lines. It is possible to collect amniotic stem cells for donors or for autologuous use.

Cord blood-derived multipotent stem cells display embryonic and hematopoietic characteristics. Phenotypic characterization demonstrates that (CB-SCs) display embryonic cell markers (e.g., transcription factors OCT-4 and Nanog, stage-specific embryonic antigen (SSEA)-3, and SSEA-4) and leukocyte common antigen CD45, but that they can be negative for blood cell lineage markers. Additionally, CB-SCs display very low immunogenicity as indicated by expression of a very low level of major histocompatibility complex (MHC) antigens and failure to stimulate the proliferation of allogeneic lymphocytes.

HSC are typically available from bone marrow, Peripheral blood stem cells, Amniotic fluid, or Umbilical cord blood. In the case of a bone marrow transplant, the HSC are removed from a large bone of the donor, typically the pelvis, through a large needle that reaches the center of the bone. The technique is referred to as a bone marrow harvest and is performed under general anesthesia. Peripheral blood stem cells are a common source of stem cells for allogeneic HSCT. They can be collected from the blood through a process known as apheresis. The donors blood is withdrawn through a sterile needle in one arm and passed through a machine that removes white blood cells. The red blood cells may be returned to the donor. The peripheral stem cell yield may be boosted with daily subcutaneous injections of Granulocyte-colony stimulating factor, serving to mobilize stem cells from the donors bone marrow into the peripheral circulation.

It is also possible to extract hematopoietic stem cells from amniotic fluid. Umbilical cord blood is obtained from an infant's Umbilical Cord and Placenta after birth. Cord blood has a higher concentration of HSC than is normally found in adult blood. However, the small quantity of blood obtained from an Umbilical Cord (typically about 50 mL) makes it more suitable for transplantation into small children than into adults. Multiple units could however be used. Newer techniques using ex-vivo expansion of cord blood units or the use of two cord blood units from different donors allow cord blood transplants to be used in adults. Cord blood can be harvested from the umbilical cord of a child being born.

Unlike other organs, bone marrow cells can be frozen (cryopreserved) for prolonged periods without damaging too many cells. This is a necessity with autologous HSC because the cells are generally harvested from the recipient months in advance of the transplant treatment. In the case of allogeneic transplants, fresh HSC are preferred in order to avoid cell loss that might occur during the freezing and thawing process. Allogeneic cord blood is typically stored frozen at a cord blood bank because it is only obtainable at the time of childbirth. To cryopreserve HSC, a preservative, DMSO, must be added, and the cells must be cooled very slowly in a controlled-rate freezer to prevent osmotic cellular injury during ice crystal formation. HSC may be stored for years in a cryofreezer, which typically uses liquid nitrogen. In light of this, the invention may relate to typing and risk assessment of donor material already stored as described herein, before being considered for transplantation.

The invention encompasses the assessment of risk of an immune reaction, preferably a pre-transplantation risk assessment, whereby any given organ or tissue may be considered as donor material intended for transplantation. For example, kidney transplantation or renal transplantation is the organ transplant of a kidney into a patient, for example with end-stage renal disease. Kidney transplantation is typically classified as deceased-donor (formerly known as cadaveric) or living-donor transplantation depending on the source of the donor organ. Living-donor renal transplants are further characterized as genetically related (living-related) or non-related (living-unrelated) transplants, depending on whether a biological relationship exists between the donor and recipient.

Alloreactivity is defined as the reaction of a lymphocyte or antibody with an alloantigen, which may be understood as an antigen from foreign material. Alloantigen recognition may occur via direct or indirect alloantigen recognition, by which T cells may recognize alloantigens and potentially lead to transplant rejection after an organ transplant.

Graft-versus-host disease (GVHD) is a relatively common complication following an allogeneic cell, tissue or organ transplant. It is commonly associated with stem cell or bone marrow transplant but the term also applies to other forms of tissue graft or organ transplant. Immune cells (typically white blood cells) in the tissue (the graft) recognize the recipient (the host) as "foreign". The transplanted immune cells then attack the host's body cells. GVHD can also occur after a blood transfusion if the blood products used have not been irradiated.

Proteasomes are protein complexes inside all eukaryotes and archaea, and in some bacteria. In eukaryotes, they are located in the nucleus and the cytoplasm. The main function of the proteasome is to degrade unneeded or damaged proteins by proteolysis, a chemical reaction that breaks peptide bonds. Most antigenic peptides presented by MHC class I molecules result from the degradation of intracellular proteins by the proteasome. Proteasome degradation of mismatched HLA antigens can be predicted by computational tools as described herein.

In the context of example 5, overall survival (OS) was defined as the probability of survival, independent of disease state at any point in time. Patients alive at last follow-up were censored. Disease free survival (DFS) is defined as the probability of being alive and free of disease at any time-point of follow-up. Patients alive at their last follow-up were censored. Transplant-related mortality (TRM) is defined as mortality incidence without previous relapse of disease. Relapse is treated as a competing event. Grading of acute GvHD was defined according to international consensus and chronic GvHD was defined according to the Seattle criteria (Ref 31c, 32c). Relapse incidence (RI) is defined as the probability of relapse at any given time-point with death from any other cause treated as competing event.

FIGURES

The invention is described by the following figures. The figures provided herein represent support for particular embodiments of the invention and are not intended to limit the scope of the invention.

FIG. 1 shows boxplots of numbers of presentable peptides per clinical outcome. A-C: Numbers of presentable peptides by grades of acute GVHD. D-F: Numbers of peptides by grades of chronic GVHD. G-I: Numbers of peptides by relapse/progression of malignant diseases. J-L: Numbers of peptides by survival. The left graphs represent numbers of peptides presentable by HLA class I and II combined, the middle graphs represent numbers of peptides presentable by HLA class I, and the right graphs represent the numbers of peptides presentable by HLA class II. The horizontal lines represent the medians, the white boxes $25^{th}$-$75^{th}$ percentile and the whiskers the range. Differences in numbers of peptides were tested with Mann-Whitney U tests. A non-significant increase of numbers of presentable peptides was observed for patients that developed aGVHD grade II-IV, extensive cGVHD and those that did not relapse/progress their disease. Medians for patients with respectively no or grade I and grade II-IV aGVHD were: for peptides presentable by HLA class I and II combined 6, and 8; for peptides presentable by HLA class I 2, and 3; for peptides presentable by HLA class II 4, and 5. Medians for patients with respectively no or limited and extensive cGVHD were: for HLA class I and II combined 6, and 10; for HLA class 12.5 and 4; and for HLA class II 4, and 6. Medians for respectively non-relapsing and relapsing patients were: for peptides presentable by HLA class I and II combined 8 and 8; for peptides presentable by HLA class 14.5 and 2; and for peptides presentable by HLA class II 4 and 5. Medians for respectively surviving and non-surviving patients were: for peptides presentable by HLA class I and II combined 8 and 8; for peptides presentable by HLA class I 3 and 2; and for peptides presentable by HLA class II 4 and 5.

Figure 2:
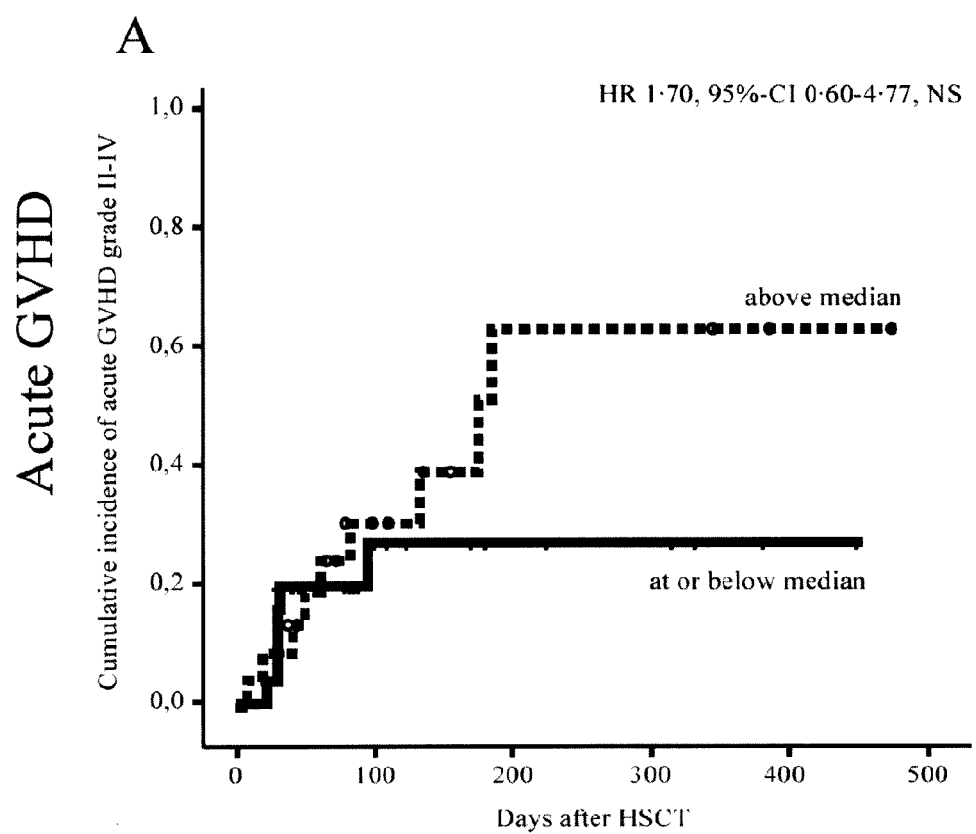
Figure 2:
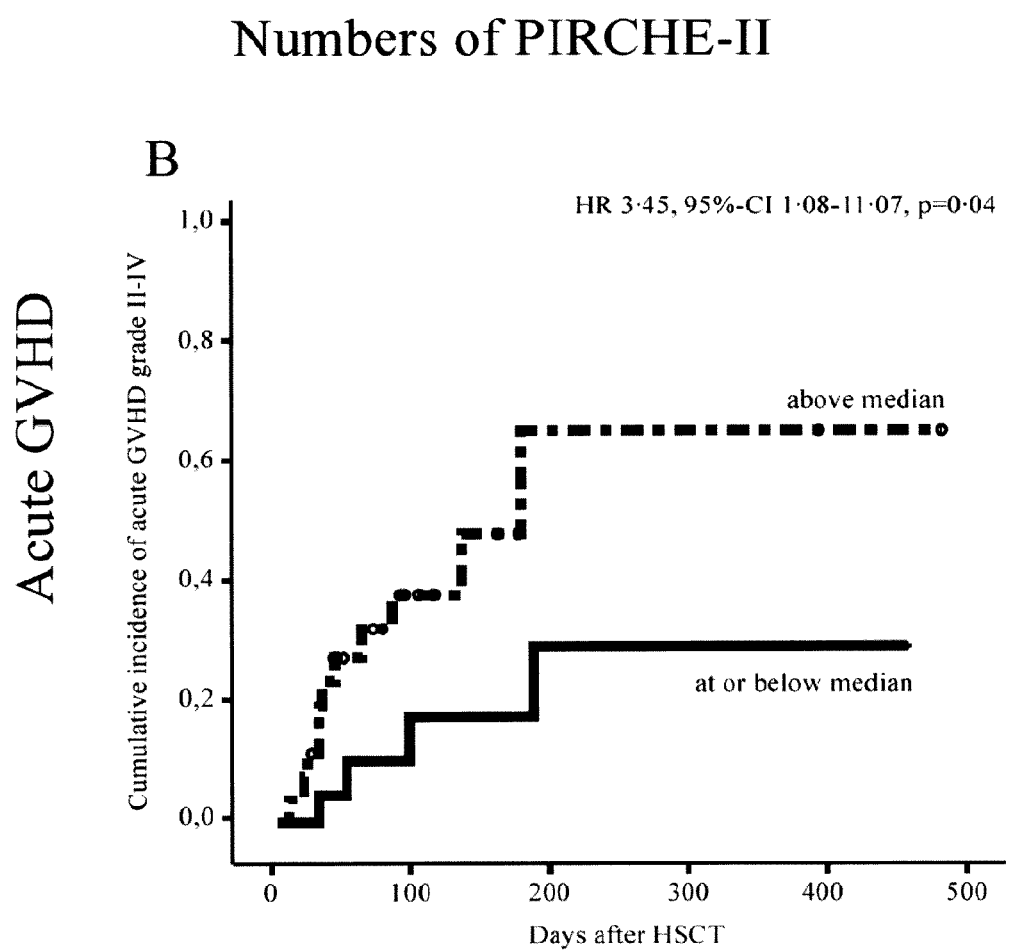
Figure 2:
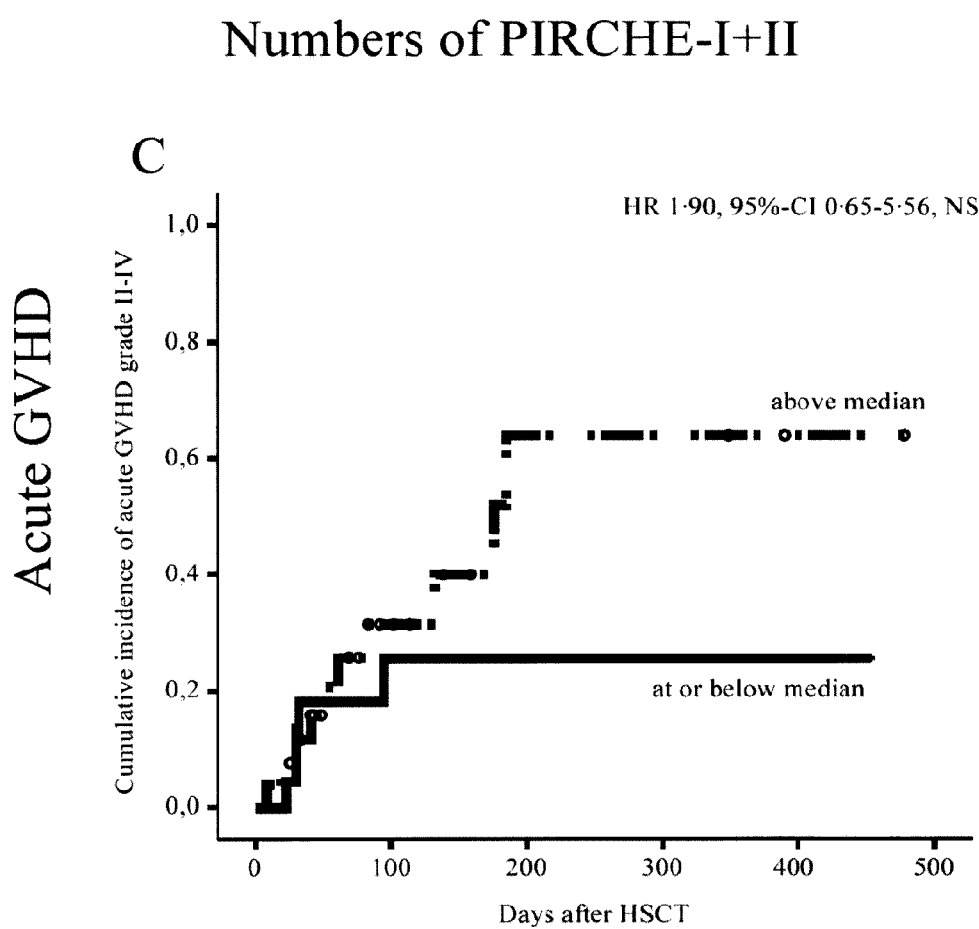
Figure 2:
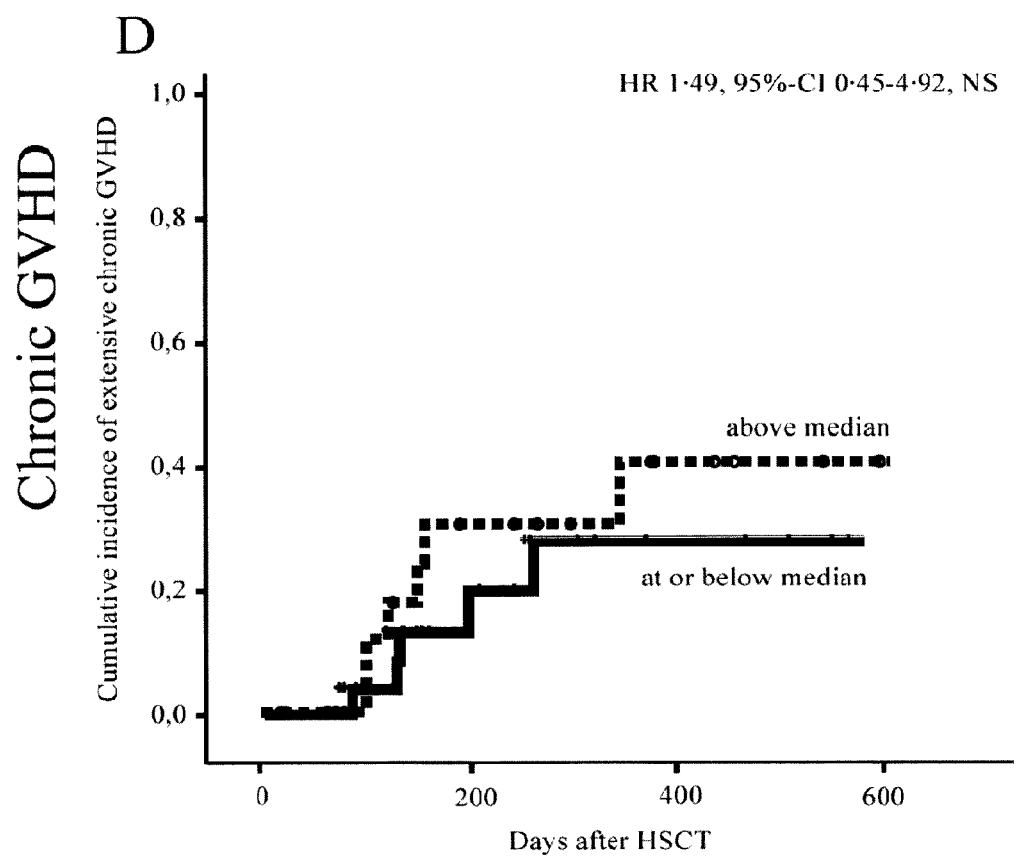
Figure 2:
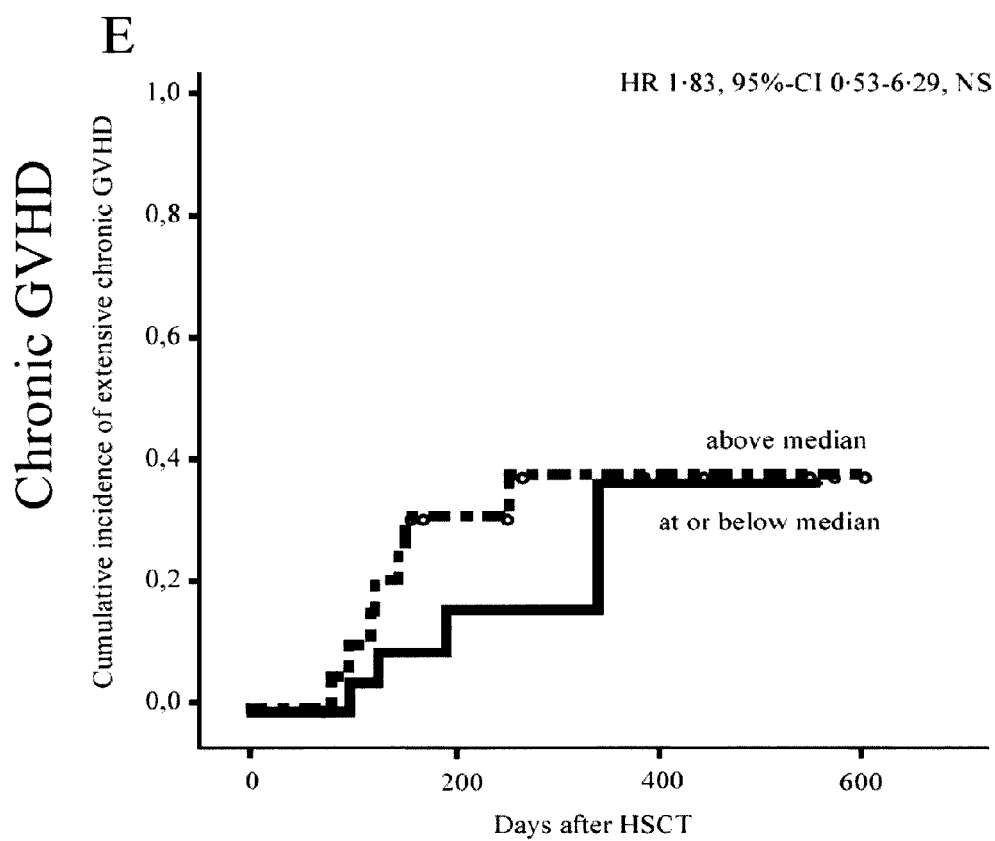
Figure 2:
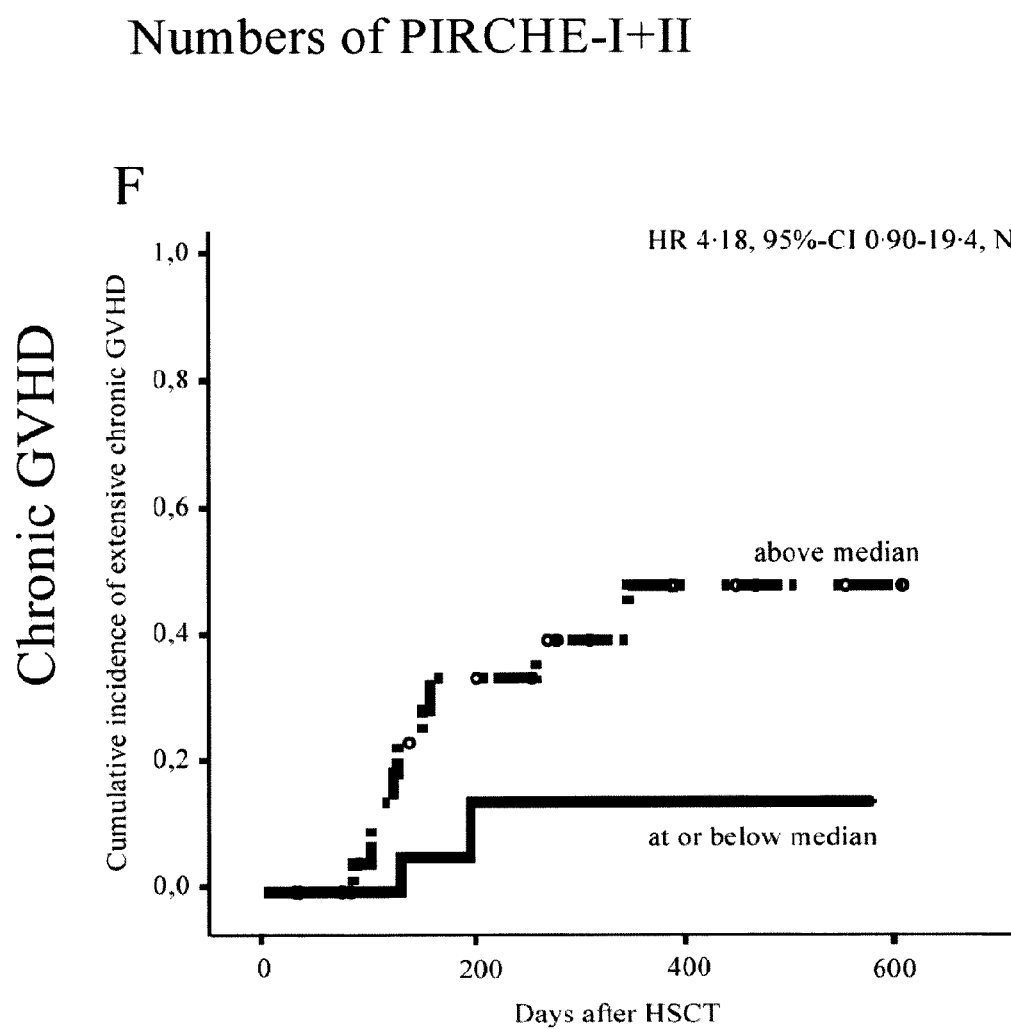
Figure 2:
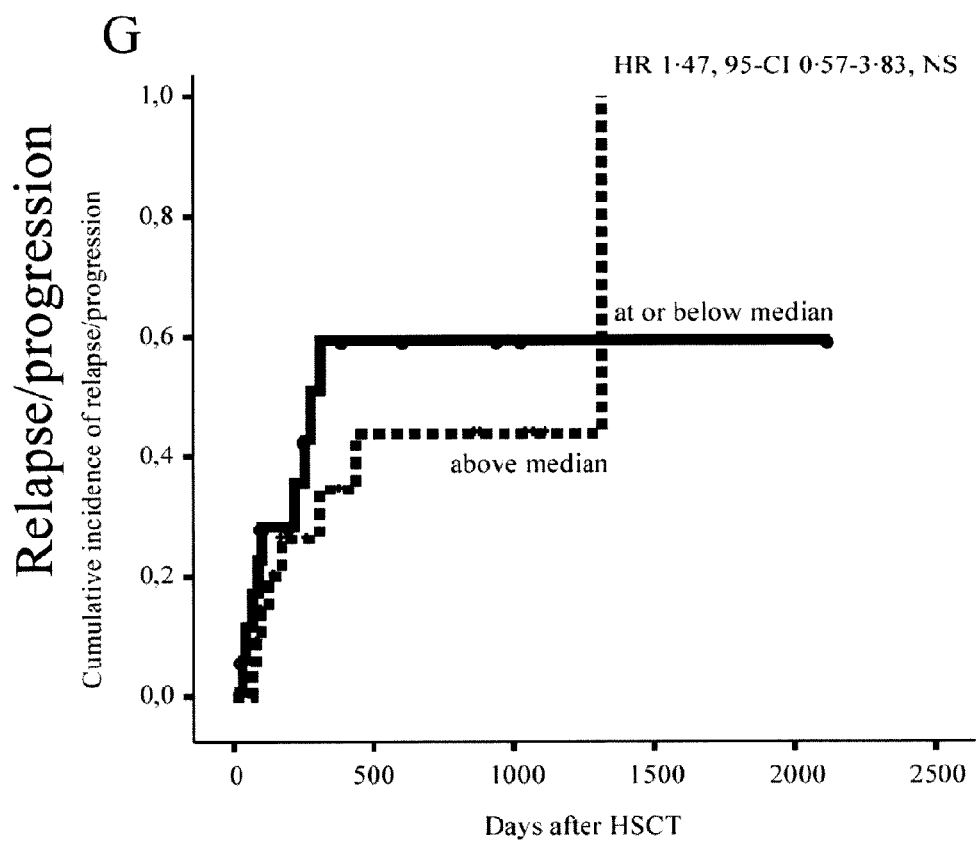
Figure 2:
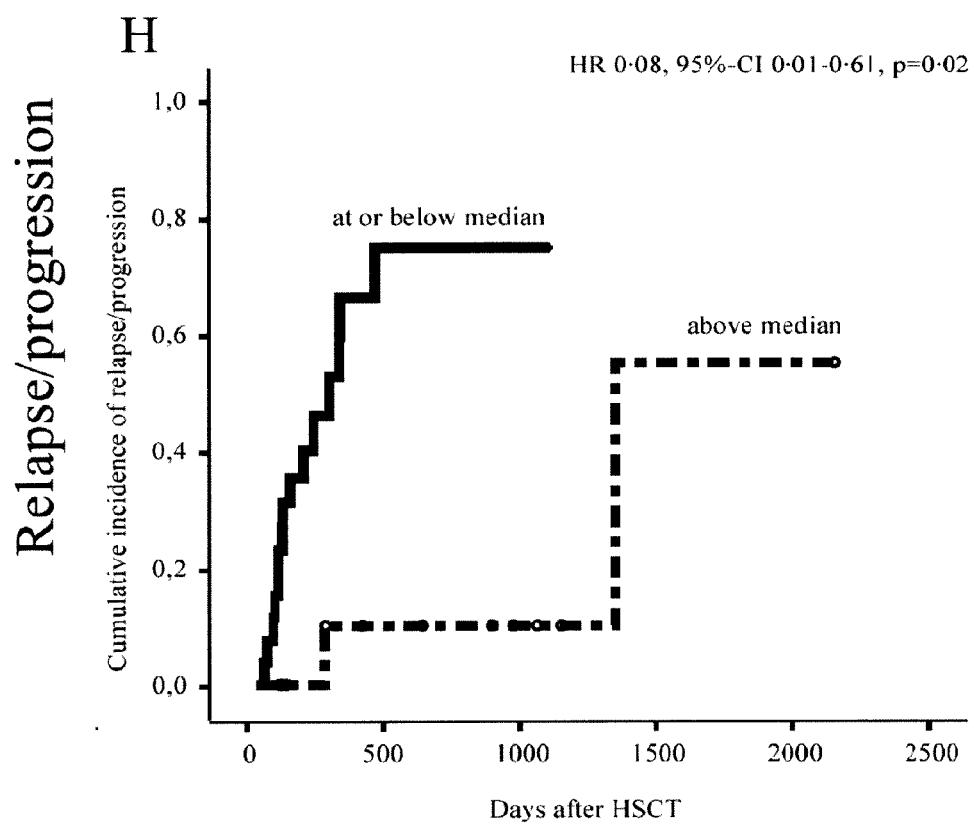
Figure 2:
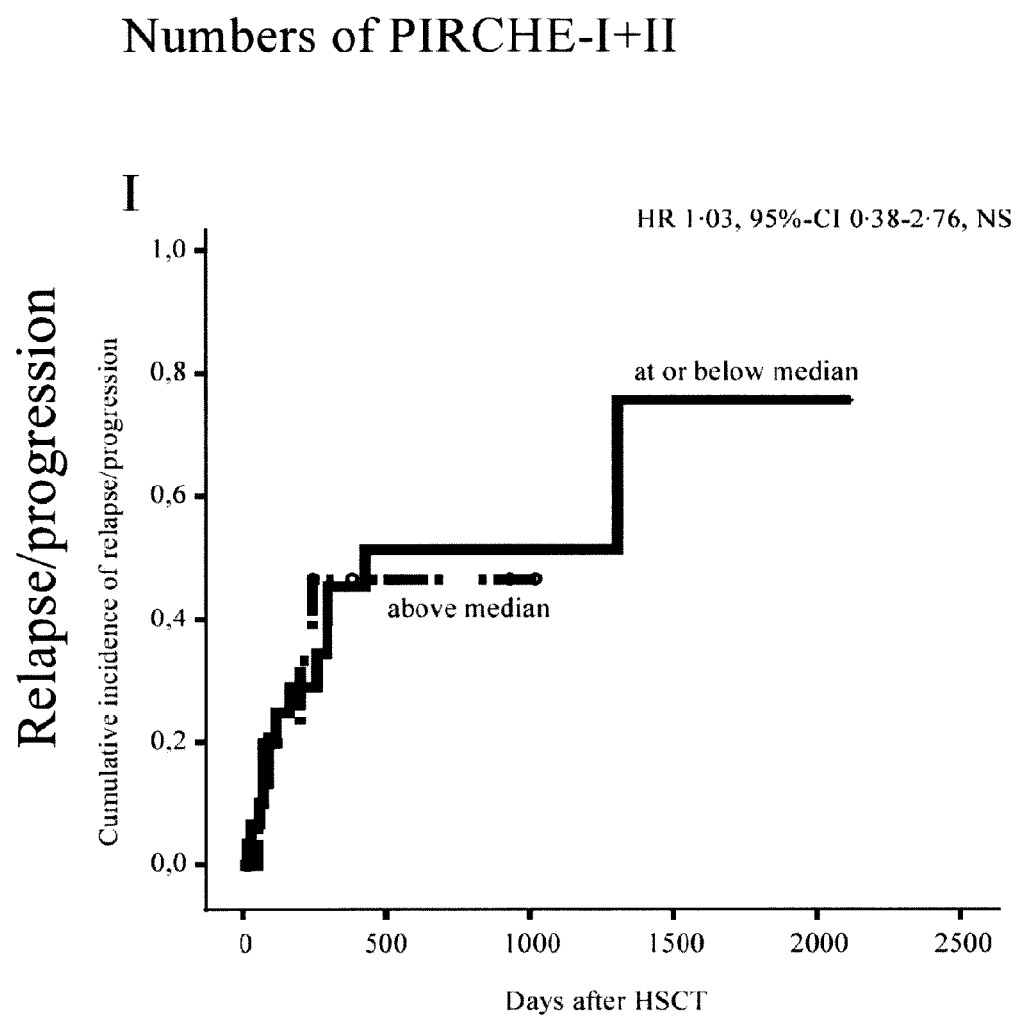

FIG. 2 shows Kaplan-Meier curves of patients with either high or low numbers of presentable peptides per clinical outcome. A-C: Numbers of presentable peptides by cumulative incidence of acute GVHD grade II-IV. D-F: Numbers of peptides by cumulative incidence of extensive chronic GVHD. G-I: Numbers of peptides by cumulative incidence of relapse/progression of malignant diseases. For each clinical outcome the median of the control group was chosen as a cut-off value, as displayed in FIG. 1. The dotted lines represent the patients predicted to present numbers of peptides above this cut-off value, the solid lines represent the patients predicted to present numbers of peptides at or below the cut-off value. Hazard Ratios were determined comparing the first group with the latter group. NS=not significant.

FIG. 3 gives a description of the kidney transplant study group matching our inclusion criteria, extracted from a cohort of 869 kidney transplant pairs.

Figure 4:
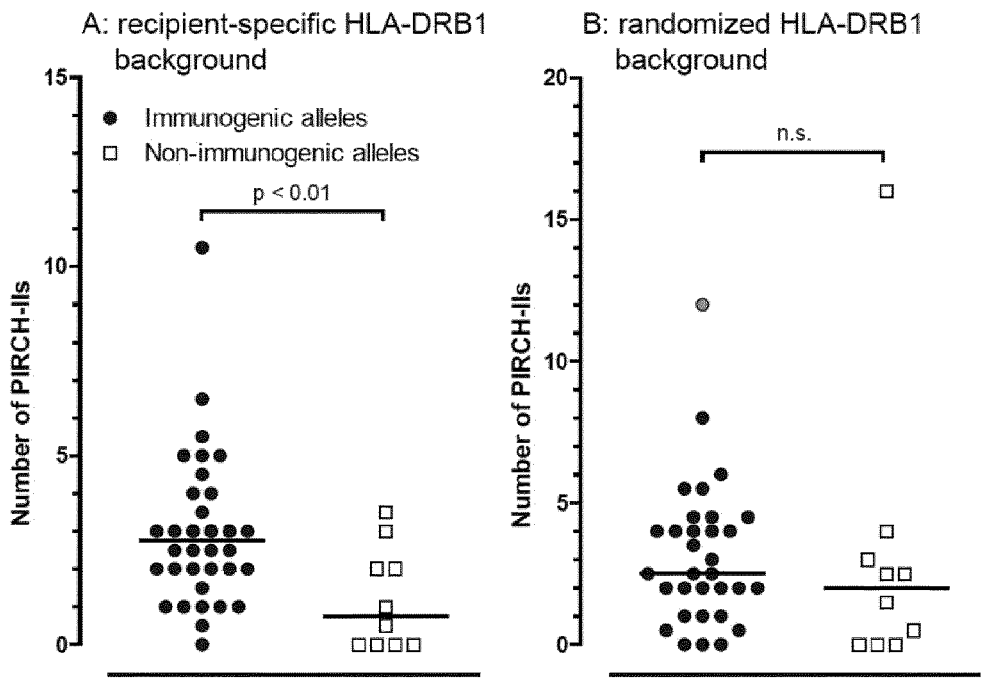

FIG. 4 shows a comparison of the number of PIRCHE-IIs in immunogenic (solid dots) and nonimmunogenic (open boxes) HLA class I alleles. A) Higher numbers of PIRCHE-IIs were observed in the immunogenic alleles as compared to the non-immunogenic alleles. B) No differences were observed when the mismatched donor-derived HLA alleles were analyzed against a scrambled recipient DRB1 background. The reported p-values are derived from the Mann-Whitney U tests.

Figure 5:
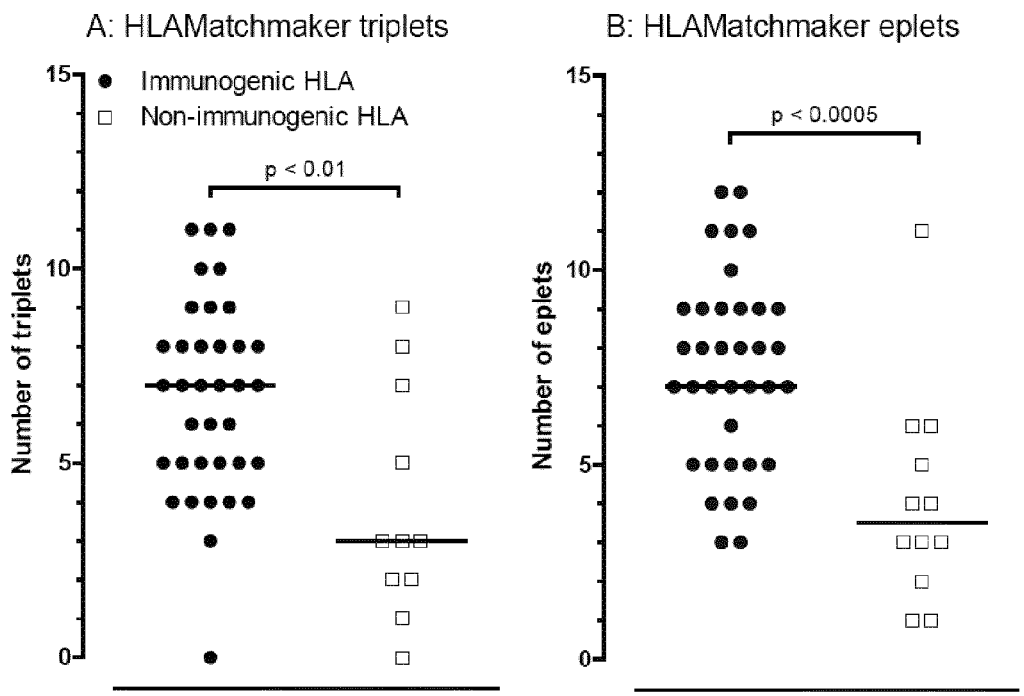

FIG. 5 shows a comparison of the number of HLAMatchmaker triplets (A) and eplets (B) in immunogenic (solid dots) and non-immunogenic (open boxes) HLA class I alleles. The reported p-values are derived from the Mann-Whitney U tests.

FIG. 6 describes the identification of eplets and PIRCHE-IIs as two separate entities. A) Correlation between the number of eplets and the number of PIRCHE-IIs. Immunogenic alleles have been depicted as solid dots; non-immunogenic alleles as open boxes. The resulting regression curves have been depicted by solid lines and dotted lines respectively. The regression coefficient is based upon combined analysis of the two groups. Overlapping data have been shifted 0.1 units for visualization purposes only. B) Location of PIRCHE-IIs on the HLA class-I molecule, as observed in the studied kidney transplant cohort. Colors indicate the relative presence of an amino acid in immunogenic HLA class I antigen; (Green=0, yellow=1 to 4, orange=5 to 9, and red=>10). The non-polymorphic beta-2m molecule has been depicted in blue. C) Location of the PIRCHE-IIs (solid line) versus eplet-related residues (black bars) in the HLA class-I molecule, as observed in a virtual transplantation cohort of 10000 simulated transplants. The eplet-related residues were defined as polymorphic residues present within 3.0 Angstrom eplet patches (4). Overlap (grey bars) was calculated as the percentage of situations where an amino acid residue was present in both an eplet and a PIRCHE-II.

Figure 7:
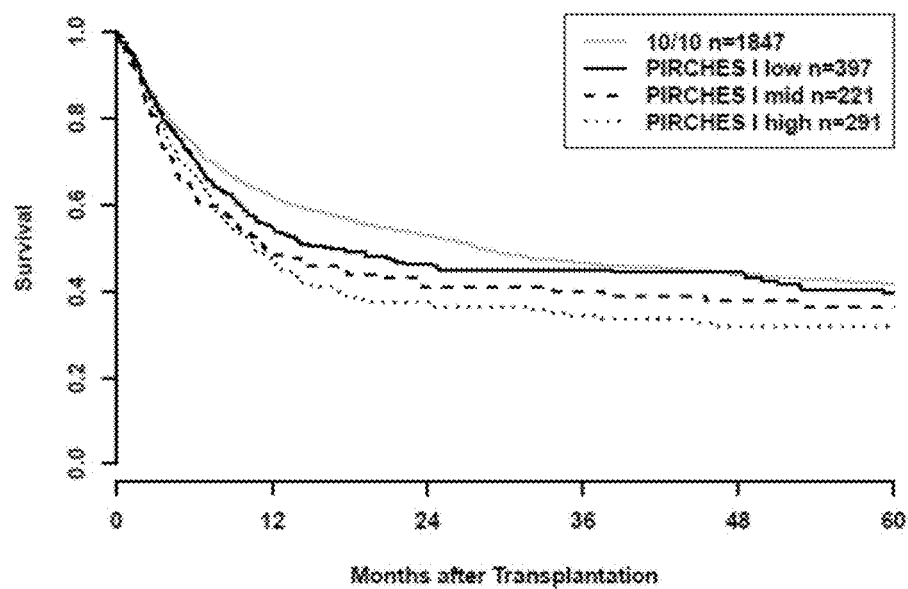
Figure 7:
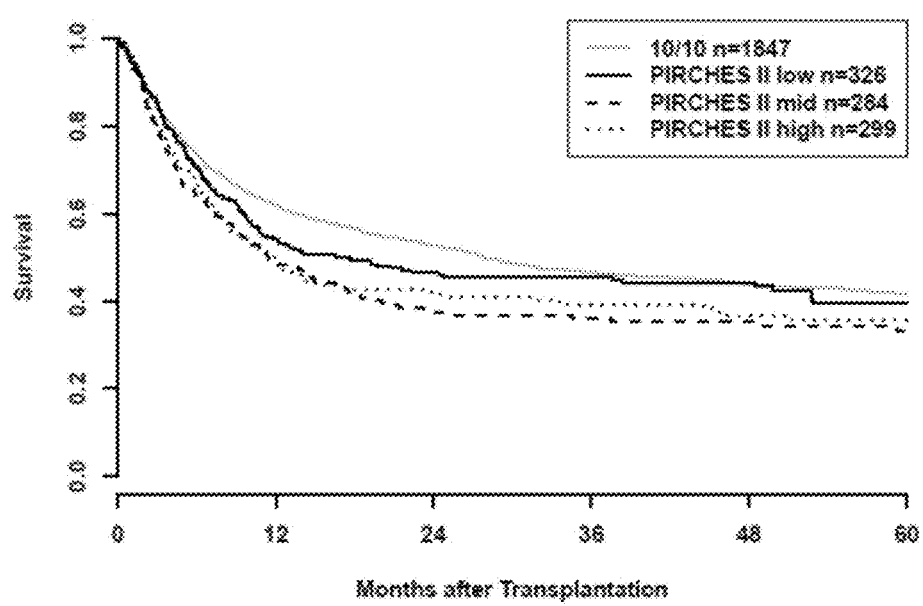

FIG. 7: A: correlation of PIRCHE-I with overall survival; B: correlation of PIRCHE-II with overall survival. Patients in both the low PIRCHE-I and -II group have similar OS rates as 10/10s. Patients with mid or high PIRCHE-I and -II have significantly reduced OS compared to 10/10s (Table 3). When comparing the three PIRCHE groups with each other, patients in the mid or high PIRCHE group (PIRCHES mid and high groups combined) had statistically significant reduced OS compared to the low PIRCHE group (PIRCHE-I: p=0.029 and PIRCHE-II: p=0.048).

FIG. 8: A: effect of PIRCHES on overall survival; B: effect of PIRCHES on disease free survival; C: effect of PIRCHES on transplant-related mortality; D: effect of PIRCHES on acute GvHD; E: effect of PIRCHES on chronic GvHD. Multivariate analysis of the effect of different PIRCHE groups compared to the reference 10/10 situation; HRs, or ORs in case of acute GvHD, are shown with 95% confidence intervals.

FIG. 9: A: correlation of PIRCHE-I with TRM, B: correlation of PIRCHE-II with TRM. Patients in both the low PIRCHE-I and -II group have similar TRM rates as 10/10s. Patients with mid or high PIRCHE-I and -II have significantly increased risks of TRM compared to 10/10s (Table 3). Low PIRCHE-I and -II were associated with significantly lower TRM compared to higher PIRCHES (p=0.038 and p=0.039 respectively).

Figure 10:
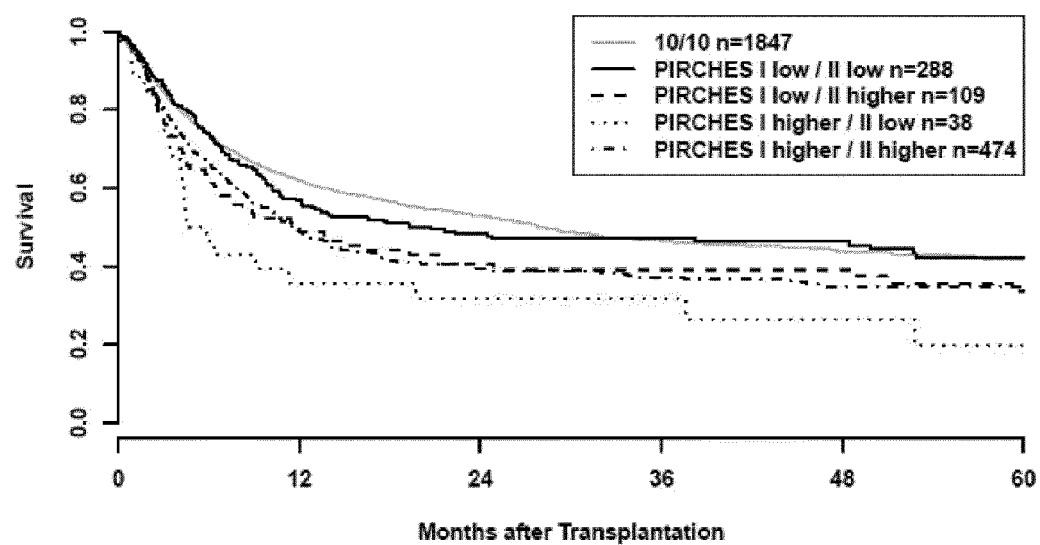

FIG. 10: interaction analyses of PIRCHE-I and -II, effect on OS. Patients presenting both PIRCHE-I and -II low numbers have OS rates comparable to 10/10s.

FIG. 11: provides two graphs showing relapse incidences for low, mid and high PIRCHE-I and for a full match for five loci (a 10/10 match) between 0 to more than 60 months after transplantation.

EXAMPLES

The invention is described by the following examples. The examples provided herein represent practical support for particular embodiments of the invention. These are not intended to limit the scope of the invention. The examples are to be considered as providing a description of possible and potentially preferred embodiments that demonstrate the relevant technical working of one or more non-limiting embodiments.

Example 1

Risk of Alloreactivity after Mismatched-HSCT Increases with Increasing Numbers of Recipient-Specific HLA-Peptides Presented by Shared-HLA Molecules Summary of Example 1:

Background: Graft-versus-host disease (GVHD) is one of the major limiting factors of hematopoietic stem-cell transplantation (HSCT). An established risk factor for GHVD is HSCT with an HLA-mismatched unrelated donor. Some mismatches appear to be more permissible, while others lead to an increased risk of developing GVHD. Currently, the biological basis for alloreactivity due to these non-permissible mismatches is unknown. The present example demonstrates use of a method to predict non-permissible mismatches and their association with the presentation of peptides derived from the recipient-specific mismatched-HLA molecules, by shared HLA to donor-T cells.

Methods: Retrospectively, 48 non-myeloablative conditioned patients, transplanted with a 9/10-matched unrelated donor, were analysed. HLA-typing was determined at high-resolution level with sequence based typing. The numbers of recipient-specific HLA peptides presentable by shared HLA was predicted using an in silico approach and the median number of predicted peptides of the control groups was chosen as cut off value.

Results: Patients predicted to present higher than median number of peptides on HLA class I developed acute GVHD (aGVHD) earlier and more frequently, whereas patients predicted to present higher than median peptides on HLA class I and II combined developed extensive chronic GVHD (cGVHD) earlier than patients predicted to present peptides at or below median. Furthermore, patients predicted to present higher than median numbers of peptides on HLA class I, had a reduced hazard of relapse/progression of malignant diseases and moreover, this developed much later. The occurrence of alloreactivity after mismatched HSCT can be predicted based on donor and recipient's HLA-typing prior to HSCT.

Methods:

Study population: Patients transplanted with a 9/10-matched unrelated donor in the University Medical Centre Utrecht, Utrecht, the Netherlands, between 2001 and 2011, were retrospectively analysed. Patients included in this analysis had received a non-myeloablative (NMA) conditioning regimen and were transplanted with mismatches in the GVH direction. Nonengrafted patients were excluded. In accordance with the Declaration of Helsinki and the local IRB guidelines, patients had given written consent allowing the use of their medical records for research.

Therapy: Patients were treated with NMA conditioning consisting of total body irradiation of 2 Gy on one day, ATG (genzyme) 2 mg/kg/day for four days, and fludarabine 30 mg/m²/day for three days. Patients received an unmanipulated graft. Immunosuppressive therapy consisted of cyclosporine A 4.5 mg/kg twice daily until day 120, which was then tapered by a 10% dose reduction per week in the absence of GVHD. Cyclosporine A was combined with mycophenolate mofetil 15 mg/kg, three times a day until day 84, and if there was no GVHD, tapered and stopped in two weeks. All patients received antibiotic prophylaxis, including cotrimoxazole 480 mg twice a day and valacyclovir 500 mg twice a day, as reported (Ref 16a).

HLA-typing: High-resolution HLA-typing was performed for all included patients and donors using sequence-based typing for five loci (HLA-A, -B, -C, -DRB1, and -DQB1). Allele and genotype ambiguities were resolved. For retrospective high-resolution HLA-C typing of one HSCT pair, no remaining DNA was available, however low resolution level HLA-C typing was performed previously. For this donor-recipient pair, the high-resolution HLA-typing was deduced based upon frequencies of HLA-B-C associations (Ref 17a).

HLA-derived peptide determination: Preferably, for each donor-recipient pair, presentable recipient-specific HLA-derived peptides can be identified. Of all HLA alleles of the donor and recipient, the processing of their amino-acid sequences by the proteasome and transportation via the TAP channel is predicted using NetChop 3.0 (Ref 18a, 19a). Subsequently, peptides with a high probability of being processed are tested, using NetMHCpan 2.0, for their capacity to be presented by HLA class-I alleles (HLA-A and -B) that are shared between the donor and recipient (Ref 20a, 21a). Only nonameric peptides are included in the analyses. Peptides with IC50 binding values ≤500 nM are chosen as relevant binders (Ref 22a). For HLA class-II presentation (HLA-DRB1), potential binders are predicted with NetMHCII 1.0 (Ref 23a, 24a), and IC50 binding values ≤1000 nM are considered relevant (Ref 25a). Per presenting shared-HLA allele, predicted binders derived from donor-HLA alleles are regarded as donor-self peptides and thus excluded from the analyses. For each donor-recipient pair, the number of presentable recipient-specific peptides (derived from the mismatched recipient-HLA allele and predicted to be presented by shared HLA) is counted. These recipient-specific peptides are reported as numbers of presentable peptides. The presentable peptides as identified herein are commonly referred to as predicted indirectly recognizable HLA epitopes (PIRCHES), either from class I alleles (PIRCHE-I) or class II alleles (PIRCHE-II).

Statistical methods: Evaluated clinical outcomes were: aGVHD, cGVHD, relapse/progression of malignant disease, and overall mortality (death from any cause). Factors analysed for association with these clinical endpoints were: number of presentable peptides (in total, by HLA class I and II separate), donor lymphocyte infusions (DLI), sex mismatch between recipient and donor, and patient age. Development of aGVHD was also analysed in relation to cGVHD. Relapse/progression was only analysed for recipients with malignant diseases. Death was regarded as a competing risk for GVHD and relapse. DLI and lenalidomide were regarded a competing risk for aGVHD. Median values and ranges for continuous variables and percentages for categorical variables were reported.

Differences in numbers of presentable peptides per possible clinical outcome were statistically analysed using the Mann-Whitney U test. For each clinical outcome, the median number of presentable peptides of the control group (e.g. the group without aGVHD grade II-IV, extensive cGVHD, relapse, or mortality) was chosen as a cut-off value. Patients were divided into two groups: those with high numbers of presentable peptides (above median) and those with low numbers of presentable peptides (below or at median). Kaplan-Meier curves were constructed for these groups to analyse the differences in time to onset of aGVHD and cGVHD, relapse/progression, and mortality. Log-rank tests were performed to compare the groups. Cox-regression analyses were used to determine HRs between the two groups and for testing of the other variables. P-values <0.05 were considered statistically significant. Statistical procedures were performed using SPSS 17.0 (SPSS Inc, Chicago, Ill., USA) software.

Results

Study Population:

Between August 2001 and March 2011, 48 NMA-conditioned patients were transplanted with a 9/10-matched unrelated donor. The majority were transplanted with an HLA class-I mismatch (76%). Detailed study group characteristics are listed in Table 1. For these patients the number of presentable peptides derived from the mismatched HLA is predicted. A median of eight presentable peptides (range 0-24) was observed. For HLA class I-presentable peptides, the median was three (0-12); for HLA class II-presentable peptides the median was four (0-24).

Table 1 shows study group characteristics. All recipients of a HSCT donor with a single mismatch in the GVH direction, in the University Medical Centre Utrecht, between 2001 and 2011, are listed here. Total number of recipients was 48, unless otherwise specified.

| Characteristic | N (%) |
| --- | --- |
| Recipient age in years, median (range) | 53 (18-66) |
| Recipient sex | |
| Female | 17 (35) |
| Male | 31 (65) |
| Donor sex | |
| Female | 28 (58) |
| Male | 20 (42) |

-continued

| Characteristic | N (%) |
|---|---|
| Disease | |
| Acute Leukaemia[1] | 19 (40) |
| Chronic leukaemia[2] | 1 (2) |
| Lymphoma[3] | 13 (27) |
| Multiple Myeloma | 11 (23) |
| Myelofibrosis | 1 (2) |
| Non-malignant diseases[4] | 3 (6) |
| Mismatch locus | |
| HLA-A | 10 (21) |
| HLA-B | 6 (13) |
| HLA-C | 20 (42) |
| HLA-DRB1 | 2 (4) |
| HLA-DQB1 | 10 (21) |
| DLI | |
| None | 42 (88) |
| 1-2 | 3 (6) |
| 3-5 | 3 (6) |
| AGVHD | |
| No | 19 (40) |
| Grade I | 14 (29) |
| Grade II | 10 (21) |
| Grade III | 4 (8) |
| Grade IV | 1 (2) |
| CGVHD | |
| No | 31 (65) |
| Limited | 6 (13) |
| Extensive | 11 (23) |
| Survival | |
| Yes | 33 (69) |
| No | 15 (31) |
| Relapse/progression, N = 44 | |
| Yes | 17 (39) |
| No | 27 (61) |

[1]Acute Myeloid Leukaemia, Acute Lymphoid Leukaemia, Myelodysplatic Syndrome, Fanconi Anaemia,
[2]Chronic Myeloid leukaemia,
[3]Non-Hodgkin's Lymphoma, Hodgkin's Lymphoma, Chronic Lymphoid leukaemia
[4]Non-malignant diseases: Severe Aplastic Anaemia aGVHD:

AGVHD grade II-IV was observed in 15 (31%) of all recipients (Table 1). Patients suffering from aGVHD grade II-IV displayed a non-significant increase in numbers of presentable peptides compared to those who did not develop or developed grade I aGVHD (FIG. 1A-C).

To determine the role of the number of presentable peptides in the time to onset of aGVHD, Kaplan-Meier curves were constructed to compare patients predicted to have high numbers of presentable peptides with those predicted to have low numbers. Patients with high numbers (>2) of peptides presentable by HLA class I compared to patients with low numbers (≤2), developed aGVHD significantly earlier (estimated mean 223 days and 353 days, p=0.03, FIG. 2A) and with an increased hazard (HR 3.45, 95%-CI 1.08-11.07, p=0.04). Time to onset of aGVHD did not differ significantly for patients predicted to have high numbers of peptides presentable by HLA class I and II combined or by HLA class II separately (FIG. 2B,C). DLI, sex mismatch, and age were not associated with aGVHD grade II-IV.

cGVHD:

Median follow-up time for cGVHD was 186 days. Eleven patients (23%) developed extensive cGVHD (Table 1). Patients suffering from extensive cGVHD displayed a trend for higher numbers of peptides presentable by HLA class I and II combined and by HLA class I and II separately, as compared to those with no or limited cGVHD (FIG. 1D-F).

Extensive cGVHD developed earlier in the patients that were predicted to present high numbers of peptides on HLA class I and II combined (>6) compared to low numbers (≤6) (402 versus 523 days, p=0.05, FIG. 2D), and the first group displayed a trend for an increased hazard of extensive cGVHD (HR 4.18, 95%-CI 0.90-1940, p=0.07). These trends were not observed for peptides presentable by HLA class I or II separately (FIG. 2E,F). None of the other tested variables were associated with an increased hazard for extensive cGVHD.

Relapse/Progression:

Due to limited patient numbers, relapse and progression of malignant disease were analysed as a combined clinical outcome. Relapse/progression was monitored for 44 (98%) patients suffering from a malignancy, and developed in 17 (39%) of these patients (Table 1). The relapsing/progressed group displayed a trend for lower numbers of HLA class-I presentable peptides (median for non-relapsing/progressing patients 4.5 and for relapsing/progressing patients 2, p=0.13, FIG. 1H). No differences were observed in numbers of peptides presented by HLA class I and II combined or by HLA class II separately (FIG. 1G,I).

For patients predicted to present high numbers of peptides by HLA class I (>4) in comparison to low numbers (≤4), relapse/progression developed later after HSCT (1573 versus 417 days, p<0.01, FIG. 2H) and with a reduced hazard (HR 0.08, 95%-CI 0.01-0.61, p=0.02). This effect was not present for patients that were predicted to present low or high numbers of peptides by HLA class I and II combined or HLA class II separate (FIG. 2G,I). All other tested variables were not significantly associated with the occurrence of relapse/progression.

Survival:

In this study cohort, 15 (31%) non-survivors were observed. When compared to those of survivors, numbers of presentable peptides were not statistically different for the non-survivors (FIG. 1J-L). Time to mortality did not differ when comparing patients that were predicted to present low or high numbers of peptides and none of the other tested variables were significantly associated with survival (FIG. 2J-L).

Discussion of Example 1:

Defining the best-permissible mismatch for HSCT with a 9/10-matched unrelated donor improves clinical outcome (Ref 1a). The best mismatch is frequently selected based on the outcome of the time-consuming CTLpf assay. Preferably, the method according to the present invention predicts alloreactivity in the 9/10 HSCT setting. This method is in particular based upon the concept of indirect recognition of HLA-disparities; peptides derived from HLA-disparities are potential T cell targets when presented by HLA alleles shared by the donor and recipient. Higher numbers of these recipient-specific presentable peptides are associated with clinical alloreactivity.

For patients who were predicted to present high numbers of peptides on HLA class I, a higher incidence and earlier development of aGVHD can be observed than for patients who are predicted to present low numbers (FIG. 2B). This observation is in line with the commonly accepted role for CTLs in the pathogenesis of aGVHD (Ref 26a). Moreover, it matches the predictive potential of CTLpf assays and the lack of predictive potential of mixed lymphocyte culture (MLC) assays; CTLpf assays focus on responses to HLA class-I mismatches, while MLC assays mainly test the response towards HLA class-II mismatches (Ref 27a).

Patients predicted to present high numbers of peptides on HLA class I and II combined, displayed a trend for an increased hazard of extensive cGVHD compared to patients predicted to present low numbers (FIG. 2D). It is preferred that the development of cGVHD involves presentation of HLA-derived peptides by professional antigen presenting cells (APCs), resulting in an interaction between HLA class II and CD4$^+$ T cells. In animal models, both host and donor APCs have been demonstrated to be important in priming donor CD4$^+$ T cells, but the exact clinical relevance has remained uncertain (Ref 28a). Testing of the role of APCs in the development of cGVHD remains difficult, because no model completely represents the complex phenotype and delayed onset of human cGVHD.

A clear effect of number of presentable peptides on GVT reactivity was observed; patients predicted to present >4 peptides by HLA class I relapsed/progressed much later and with a reduced incidence (FIG. 2H). This effect can be explained by increased possibility of the donor T cells to recognize patient tumour cells. The method according to the present invention is thus preferably not only able to predict the pathological effect of indirect recognition of HLA-disparities, but also the desired effect. However, the reduction in relapse was observed for patients with an increased risk of aGVHD (predicted to present >2 peptides on HLA class I).

HLA-C mismatches lead to a disproportional increased risk of alloreactivity (Ref 2a, 29a). As HLA-C appears to be less stable on the cell surface (Ref 30a), direct recognition of recipient-specific HLA-C alleles is less likely. Thus, after HLA-C-mismatched HSCT, indirect recognition of recipient-specific HLA-C alleles might be the most important route of evoking alloreactivity. HLA-C presentation might be a possible explanation due to the large number of peptides derived from HLA-C mismatches. When predicting the numbers of presentable peptides derived from HLA mismatches, significantly higher numbers of peptides derived from mismatched HLA-C alleles were predicted to be presented by HLA class I than derived from HLA-A or HLA-B (Table 2). A similar trend was observed when comparing HLA-C with HLA-DQB1 mismatches. Taken together, these results demonstrate that the increased risk of alloreactivity by HLA-C mismatches is due to the higher numbers of presentable peptides derived from HLA-C mismatches.

Table 2 shows numbers of predicted presentable peptides per mismatched HLA-locus. Numbers of HLA-C derived presentable peptides were significantly higher than HLA-A or HLA-B derived presentable peptides. For HLA-DRB1, differences could not be determined since only two HLA-DRB1 mismatches were included in the cohort.

| Mismatched Locus | N (%) | Number of presentable peptides on HLA class I, median (range) | P-value |
| --- | --- | --- | --- |
| HLA-A | 10 (21) | 2 (0-7) | NS,$^{\$,*}$ p = 0.03$^{\char94}$ |
| HLA-B | 6 (13) | 0 (0-5) | NS,$^{\#,*}$ p = 0.03$^{\char94}$ |
| HLA-C | 20 (42) | 6.5 (0-12) | p = 0.03,$^{\#,\$}$ NS* |
| HLA-DRB1 | 2 (4) | 0 (0) | NA |
| HLA-DQB1 | 10 (21) | 2.5 (0-9) | NS$^{\#,\$,*}$ |

$^{\#}$compared to numbers of presentable peptides derived from HLA-A mismatches
$^{\$}$compared to numbers of presentable peptides derived from HLA-B mismatches
$^{\char94}$compared to numbers of presentable peptides derived from HLA-C mismatches
*compared to numbers of presentable peptides derived from HLA-DQB1 mismatches
NS = not significant
NA = not available Previous attempts with computational methods to assess the differences in HLA mismatches as epitopes for antibodies (HLAMatchmaker) or as the likelihood of direct recognition by T cells (HistoCheck) were unsuccessful in predicting alloreactivity prior to mismatched-HSCT. Indeed, in the cohort, the number of eplets predicted by HLAMatchmaker and the dissimilarity scores of HistoCheck did not correlate to alloreactivity as well. The numbers of eplets and the dissimilarity scores did correlate to the numbers of peptides we predicted, corresponding with the fact that all methods assess differences in HLA polymorphisms. The difference in predictive potential of alloreactivity amongst HLAMatchmaker, HistoCheck in the present invention offers the possibility of indirect recognition of HLA-disparities predicts alloreactivity, whereas predicting the possibility of direct recognition or antibody formation does not.

It is preferred that the present invention focuses on a homogenous cohort of NMA-conditioned patients for evaluating the effect of numbers of presentable peptides. MA-conditioned patients were not evaluated for three reasons. First, as has extensively been shown, MA regimens increase the risk of alloreactivity (Ref 1a). Second, NMA conditioning is the most frequently used regimen. Finally, consequently, the number of MA-conditioned patients was too low (N=12) to properly analyse the effect of presentable peptides additive to the effect of conditioning.

As shown in example 1, according to the present invention the prediction of numbers of recipient-specific peptides that are presentable on shared-HLA alleles correlates with alloreactivity (i.e. aGVHD and relapse/progression). The prediction of these numbers of presentable peptides assists in defining the best permissible mismatch for patients receiving a 9/10-matched unrelated donor. It is further preferred that the method is of benefit for alternative forms of mismatched HSCT, e.g. in single or double cord-blood transplantation. Preferably the usage of the method improves donor selection in mismatched HSCT.

Example 2

Predicted Indirectly ReCognizable HLA Epitopes Correlate with Chronic Graft-Versus-Host-Disease and Relapse-Related Mortality in Pediatric Patients after Cord Blood Transplantation Background and Objectives:

Haematopoietic Stem-Cell Transplantation (HSCT) with an HLA-mismatched donor is a risk factor for Graft-Versus-Host Disease (GVHD). According to the present invention, graft-versus-host reactivity after HSCT with single HLA mismatched adult-unrelated donors can be predicted in advance. It is preferred that the number of peptides derived from the mismatched-HLA allele presented in matched HLA (Predicted Indirectly Recognized HLA Epitopes; PIRCHES) correlates to the development of alloreactivity. Since HLA mismatches are better tolerated in case of transplantation with Cord Blood (CB), CB donors are often selected with more than a single HLA mismatch. According to the present invention preferably the number of PIRCHES correlates to alloreactivity after CB transplantation.

Material and Methods:

The clinical outcome of 79 pediatric patients, transplanted with a single CB donor was analyzed retrospectively. Preferably HLA-typing was performed at high-resolution level. Numbers of PIRCHES were determined using NetChop and NetMHC-Pan for HLA class I presented PIRCHES (PIRCHE-I), and NetMHC-II for HLA class II presented PIRCHES (PIRCHE-II), as described in Example 1.

Results:

According to Example 2 higher numbers of PIRCHE-II correlate with an increased risk of developing extensive chronic GVHD. Higher numbers of PIRCHE-I is preferably associated with a decreased risk of mortality due to relapse. Patients with non-engraftment or graft rejection present significantly higher numbers of PIRCHE-I in the host-versus-graft direction. The number of PIRCHE-II predicts the development of chronic GVHD, while the number of PIRCHE-I predicts the development of relapse-related mortality. According to the present invention preferably CB transplantation outcome is improved by selecting CB units that lead to a reduction in extensive chronic GVHD without compromising the Graft-versus-Leukemia effect.

Example 3

Predicted Indirectly Recognizable HLA Epitopes Presented by HLA-DRB1 Correlate with the De Novo Development of Donor-Specific HLA IgG Antibodies after Kidney Transplantation The present invention provides methods for prediction of the role of T-helper cell epitopes derived from HLA class-I molecules presented by HLA class-II molecules from the recipient in the formation of donor-specific HLA antibodies of the IgG isotype. A role for the HLA-DRB1 molecule of the recipient in the formation of these antibodies has been suggested earlier. In Example 3 a large cohort of more than 800 kidney recipients is used. From this cohort, all non-immunized patients receiving their first kidney transplant are selected, followed by rejection and nefrectomy. The de novo production of donor-specific HLA class-I antibodies (DSA) is analyzed and correlated data the predicted indirectly recognizable HLA epitopes presented by HLA class II of the recipient (designated as PIRCHE-IIs). Despite the relatively small numbers of recipients that matched the inclusion criteria, in particular it is possible to show that immunogenic HLA alleles, i.e. alleles that resulted in DSA, contain more PIRCHE-IIs than non-immunogenic alleles. Moreover, by using a random HLA-DRB1 background, it could be shown that this effect is indeed restricted to the presenting HLA allele. Data on the localization of PIRCHE-IIs and eplets, suggest that these epitopes indeed function as an entity independent from eplets in the generation of donor-specific HLA antibodies. Through this analysis the underlying technical effects are demonstrated, which enable provision of a method for alloimmunity determination and/or prediction after transplantation, which leads to an additional tool to define acceptable mismatches.

Summary of Example 3:

Background: HLA class-I mismatches selectively induce antibody formation after kidney transplantation. The de novo development of donor-specific IgG HLA class-I antibodies may be dependent on the HLA class-II background of the patient by presenting T-helper epitopes within the recognized HLA class-I antigens.

Methods: The correlation between antibody production against mismatched donor human leukocyte antigens (HLA) class I and the number of HLA class II-restricted predicted indirectly recognizable HLA epitopes (PIRCHE-II) in the respective HLA class-I mismatches is described by Example 3 of the present invention. To this end, sera taken after nefrectomy from a cohort of 21 non-immunized individuals that received and rejected a renal transplant are analyzed.

Results: Fourty-nine HLA class-I mismatches were found which all contained immunogenic eplets according to HLA-Matchmaker. Donor specific HLA antibody responses were detected against 38 HLA class-I mismatches after nefrectomy. These mismatches were found to contain a larger number of PIRCHE-II when compared to mismatches which did not induce donor specific HLA antibodies. Most PIRCHE-II (more than 60%) were not part of an eplet as defined by HLA-Matchmaker. The present invention therefore provides a method that that utilises the finding that the presentation of donor-derived HLA class-I peptides by recipient HLA class-II molecules plays a significant role in de novo development of donor-specific IgG HLA antibodies.

Recipients, Materials, and Methods:

Transplant Recipients:

The entire cohort of 869 kidney transplants that were performed between 1990 and 2008 in the University Medical Center Utrecht, Utrecht, The Netherlands was analyzed. From this cohort, recipients were selected whose kidney graft was removed and had no pre-transplant alloimmunizing event, i.e. no pregnancy, blood transfusions, or previous organ or stem-cell transplantation. Recipient pairs that were fully matched for the HLA-A and HLA-B antigens were excluded, as they were not informative for this study purpose. One pair was excluded because no binding algorithm was available for the recipient's HLA class-II alleles. These selection criteria resulted in 21 analyzable recipient-donor pairs. For all donor-recipients combinations T-cell crossmatch assays were performed using the basic NIH technique on unseparated peripheral blood mononuclear cells in the presence of dithiothreitol before transplantation. All crossmatch results in were negative.

Samples:

Serum samples were obtained at two time points. First, pre-transplant sera used for crossmatching was analyzed. Second, post-transplant sera were used which were obtained three months after transplantectomy. The reason for the latter time point is that at that time immune suppression was absent and antibody analysis was no longer influenced by any antibody filtering effect of the donor kidney. All sera of the recipients were obtained for purposes of regular panel-reactive HLA antibody (PRA) screening.

HLA Typing:

For each recipient, two independently collected samples were typed with different methods; one sample was typed serologically, using the conventional complement-dependent cytotoxicity (CDC) procedure using commercial typing trays (Biotest, Dreieich, Germany) and one sample was typed molecularly at intermediate resolution for the HLA class-I and -II alleles based upon the PCR-SSO technique in combination with Luminex using commercial reagents and following the instructions of the manufacturer (OneLambda Inc., Canoga Park, CA, USA). For donor typing, only one sample was available locally to perform both serological and molecular typing, following the identical procedure as for recipient typing. In all cases, donor typing in our center confirmed the HLA typing provided by the donor center. An additional high-resolution typing was performed from all recipients and donors of whom DNA was still available. From the remaining 5 individuals, all typing results were converted to the most likely high resolution typing based upon the reported HLA frequencies within the observed NMDP multiple allele codes (Ref 15b). In one case, this approach led to multiple options with a frequency of more than 10%; a B44 could be converted into either a B*44:02 or a B*44:03 (FIG. 3). Even though these HLA molecules differ for only one amino acid, one for this pair, data were analyzed for both possibilities and the results were averaged for this pair.

HLA Antibody Screening and Characterization:

Tests were performed to determine the presence or absence of HLA antibodies to HLA-A and -B using the Labscreen Single Antigen kits (OneLambda Inc.) following the standard manufacturer's guidelines. Beads were analyzed on a Luminex 200 flow cytometer (Luminex Inc., Austin, Tex., USA). Results with an MFI of >1000 were scored as positive.

Identification of HLA Class I-Derived PIRCHE-II:

According to the present invention, preferably for all mismatched HLA class-I molecules, the number of PIRCHE-IIs is examined to explain a potential antibody response to the epitope-containing HLA class-I allele. PIRCHE-IIs are defined in this example as recipient HLA class-II binding epitopes within the mismatched donor-derived HLA class-I molecule, that are not covered by any of the other HLA class-I alleles of the recipient. HLA class I-derived PIRCHE-IIs are predicted using the HLA class-II binding predictor NetMHCII (Ref 23a). This predictor is based upon the SMM-align predictor (Ref 24a) to predict how a potential ligand aligns to the binding groove of an HLA class-II molecule, and it subsequently predicts how well the aligned ligand is expected to bind. If the predicted binding affinity is high (IC50<1000 nM) (Ref 16b), the nine amino acids that aligned to the binding groove are defined as an HLA class-II epitope.

Matchmaker Analyses:

HLAMatchmaker eplets is assigned to the HLA alleles based on HLAMatchmaker version 2.1 (http://www.HLA-Matchmaker.net) (Ref 17b). Only the HLA-A, and -B loci is included in these analyses. The number of mismatched eplets is determined as the number of donor eplets that were absent in the recipient's HLA-A and -B locus.

Location of T-Helper Ligands and Eplets:

Different polymorphic residues within the HLA molecule contribute to the different types of mismatches, i.e. as determined by either the eplet- or the PIRCHE-II method. To identify the polymorphic residues that were involved in eplets and/or PIRCHE-II, preferably an analysis is conduct out of data obtained from the study cohort and a cohort of randomly generated virtual recipient-donor pairs. For the latter cohort, a virtual population reflecting the HLA-A/B/C/DR-haplotype frequencies in Caucasians was generated. These haplotype frequencies were obtained from previous studies (Ref 15b). To simulate a recipient-donor combination matching the local match profile, a maximum of three mismatches on the combined HLA-A and -B loci, and one on the HLA-DR locus is accepted. The generation of virtual individuals was stopped when a total number of 10000 virtual recipient-donor combinations that fitted these requirements, was reached. Subsequently, the mismatched HLA class-I alleles were assessed using the eplet method and the PIRCHE-II method as described above. Relative frequency plots were constructed based upon the location of eplets and PIRCHE-II within the HLA molecule. To measure the overlap in position usage between the PIRCHE method and the eplet method, the usage of each amino acid by either methods was determined at those positions that are variable among MHC-I molecules. For both methods, the usage counts were normalized such that they sum up to 100%. The overlap between the counts was determined as the overlap between these normalized usage counts.

Statistical Analyses:

All mismatched alleles from the donor were separated into a group for which DSA were detected (immunogenic group) and a group for which no DSA could be demonstrated (non-immunogenic group). Between these two groups, the number of non-self HLA class I-derived PIRCHE-IIs and/or the number of HLAMatchmaker triplets and eplet were compared using the Mann-Whitney U test (GraphPad Prism 5.03, GraphPad Software, Inc., La Jolla, Calif.).

Results:

Overview of Specificities:

A total of 22 recipients matched the inclusion criteria (FIG. 3). In sera of 21 of them, donor-specific antibodies could be detected. A total of 38 immunogenic (18 HLA-A and 20 HLA-B) and 11 non-immunogenic alleles HLA alleles (3 HLA-A and 8 HLA-B) could be identified. These numbers were equally distributed (Chi-square test, data not shown).

Immunogenic Alleles Contain More PIRCHE-II:

For all mismatched alleles according to the present invention in particular the number of non-self HLA class I-derived PIRCHE that can bind to the HLA-DRB1 allele of the recipient is predicted. As shown in FIG. 4A, the immunogenic group contains a higher number of PIRCHE-IIs as compared to the non-immunogenic group (p<0.01 in the Mann-Whitney U test). The mean values were 3.0 and 1.2, respectively. These differences were not observed when the mismatched donor-derived HLA alleles were analyzed against a scrambled recipient DRB1 background (FIG. 4B), indicating that the DRB1 background of the specific recipient plays a role in the PIRCHE-II analyses.

Immunogenic Alleles have Increased Numbers of Triplets and Eplets:

The immunogenic group and the non-immunogenic group were compared for their number of triplets and eplets as determined by HLAMatchmaker. Both the number of triplets (FIG. 5A) and the number of eplets (FIG. 5B) are significantly higher in the immunogenic group than in the non-immunogenic group (triplets: p<0.005; eplets: p<0.0005 in Mann-Whitney U tests).

Eplets do not Co-Localize with PIRCHE-II:

Based upon the shared biological origin of eplets and PIRCHE-II, a correlation between the number of eplets and the PIRCHE-IIs is to be expected. To address this issue, the number of eplets against the number PIRCHE-IIs and performed correlation analyses was plotted. Correlations were observed both for the non-immunogenic alleles (R2=0.83; significance of the slope: p<0.0005) and the immunogenic alleles (R2=0.14; significance of the slope: p<0.05; FIG. 6A). The slopes of the two groups were overlapping each other. Subsequently the topographic location of the PIRCHE-II in the study cohort, indicated by the position of the involved amino acids was analyzed. The location of these PIRCHE-IIs was compared to the location of the eplets. The polymorphic amino acids of PIRCHE-IIs are highly over-represented in the β-plated sheet and in the alpha-3 domain of the HLA protein (FIG. 6B), whereas the eplets are located on surface residues of the HLA protein, accessible to antibodies. These data were confirmed by simulation experiments on 10000 virtual transplant pairs (FIG. 6C), showing that a significant number of HLA class I-derived polymorphic amino acids (62%) can be identified as PIRCHE-II, while not being part of an eplet recognized by DSA.

Discussion of Example 3:

The HLA-DR phenotype of the responder may play a determinative role in the immunogenicity of HLA antigens (Ref 7b, 8b, 18b). The production of Bw4-specific antibodies strongly correlates with the presence of either the HLA-DR1 or HLA-DR3 phenotype in the responder. In vitro, a Bw4-derived peptide binds strongly to DRB1*01- and DRB1*03-expressing cells, while the corresponding Bw6 peptide does not. Similarly, HLA-DRB1*15:01 shows an enrichment in the production of HLA-A2 antibodies in HLA-A2-mismatched transplant pairs (Ref 24a). Based upon this concept, it has been proposed to consider HLA class-I mismatches of the donor in the context of the HLA-DR phenotype of the responder in order to improve the outcome of kidney transplantation. So far, this concept has only been evaluated without taking the HLA class-I background of the recipient into account. Moreover, given the large number of HLA alleles, enormous transplantation cohorts would be required to define all combinations that are at risk with this approach.

According to the present invention preferably a computational approach for HLA binding with subtraction of the self-HLA to explain donor-specific HLA antibodies on a strictly selected cohort is applied; only those recipients were included that had no pre-transplant immunizing event and whose kidney graft was removed before analyzing the HLA antibodies. Although this selection led to a smaller study population, the analyses could be confined to a single immunizing event, i.e. the kidney transplantation. Moreover, this selection excluded influence of absorption effects of a residual donor organ, which can hamper correct detection of donor-specific HLA antibodies in serum (Ref 19b). With the present invention it is demonstrated that immunogenic donor-derived HLA class-I alleles, defined as alleles towards which DSA are detectable, contain a higher number of epitopes that can be presented by HLA class-II molecules, PIRCHE-IIs, from the recipient. Evidently, the level of similarity between donor's and recipient's HLA class-I alleles affects the number PIRCHE-IIs; the lower the similarity, the higher the chance to find non-self epitopes. The recipient's HLA-DR rather than the level of similarity is explaining the observations. The confirmation therefore is for example given with counting the number of PIRCHE-II using a random HLA-DR background. In these analyses, immunogenic and non-immunogenic alleles showed a similar number of peptides in the context of the random HLA-DR background (FIG. 4B). Thus, the actual HLA-DR background of the recipient has to be taken into account to explain why certain mismatches are immunogenic or not. The recipient-specific HLA-DR background is essential in predicting the chance of developing DSA after transplantation and the observed differences are due to differences in antigen presentation and not in similarity between the mismatches. The HLAMatchmaker effect and the PIRCHE-II effect are two independent parameters, both supporting the development of DSA.

Two factors improve the outcome of our analyses; the quality of the HLA class II-binding prediction and the resolution of HLA typing of recipient and donor. In NetMHCII, the HLA binding motives are well-defined for 9 HLA-DR antigens including 11 different HLA-DRB1 alleles. Thus, for a number of HLA-DRB1 alleles the peptide binding characteristics have not been determined. Given the high level of diversity in HLA-DRB1 alleles, characterization of each individual HLA class-II binding motif via peptide-screening binding assays is not feasible. Therefore, an alternative algorithm, NetMHCIIpan, has been developed via a computational approach (Ref 20b).

NetMHCIIpan can define binding motifs on the basis of the primary amino-acid sequence, providing information for alleles for which limited experimental binding data have been reported (Ref 20b). For the data set, NetMHCIIpan would only provide a better prediction for the HLA-DRB1*13:01 allele. As such, analyses with NetMHCIIpan did not enhance the performance of the models (data not shown). In the present retrospective study, low resolution typing data could not be extrapolated to high resolution HLA typing for 3 donors and 2 recipients. In these cases, the results from all likely options were averaged (in case of donor typing) or both subtracted (in case of recipient typing). This approach for example leads to an incorrect assignment and subsequently to an underestimation of the effect the number of T-helper ligands on the induction of specific antibodies. Thus, the effect of PIRCHE-II on the production of anti-HLA IgG antibodies is for example stronger than reported.

Both the PIRCHE-IIs described in the present invention and the eplets as determined by HLAMatchmaker are based upon the same phenomenon; mismatched amino acids in the HLA alleles of recipient and donor. As such, these two parameters cannot be fully dissected. However, although immunogenic alleles show higher numbers of eplets/triplets than the non-immunogenic alleles, various aspects of the analyses indicate that PIRCHE-II act, at least partly, independently from the number of eplets/triplets.

First, it is shown that the actual HLA-DRB1 background is essential; when using a scrambled HLA-DRB1 background, no correlation with immunogenicity was found (FIG. 4B). Second, while there is a strong correlation between the number of PIRCHE-II and the number of eplets when analyzing the non-immunogenic group, this correlation is much weaker in the immunogenic group (FIG. 6A). Third, the physical locations of amino acids that are included in potential T-helper ligands are differently distributed than the locations of eplet involved amino acids (FIG. 6B-C); the alpha-3 domain and the N-terminal part of the alpha-1 domain seem to be enriched for PIRCHE-IIs, while they rarely result in eplets. Taken together, these two parameters are complementary to each other while predicting the chance of DSA development. Indirect recognition of donor HLA class I presented by recipient HLA class II in the production of post-transplant DSA leds to a better predictive value in the retrospective study. The fact that both parameters complement each other for better predictability of developing post-transplant DSA, is in agreement with immunobiological concepts on IgG antibody formation. The finding of separate physical locations for antibody epitopes (eplets) and polymorphic class I-derived T-helper epitopes may have relevance for our understanding of 'linked recognition'.

The present invention therefore provides a novel predictive method for predicting clinically relevant alloantigens in the context of kidney transplantation.

The method according to the present invention provides a technical utilisation of the finding that the de novo development of donor-specific HLA IgG antibodies correlates with the number of HLA class 1-derived PIRCHE-II and with the number of HLAMatchmaker eplets in the mismatched HLA class-1 allele of the donor. Topographic analyses and scrambling of the HLA-DRB1 background for example show that these two phenomena result from two in part independent entities. Therefore, presentation of donor-derived HLA class-1 peptides by recipient HLA class-II molecules is an important mechanism in IgM-to-IgG isotype switching of donor-specific HLA antibodies. The present invention preferably leads to a better definition of acceptable HLA mismatches in organ transplantation and the effect of this mechanism on graft survival.

Example 4

Confirmation of and Explanation for the Effect of HLA-DPB1 Non-Permissive Mismatches on 10/10 HLA Matched Unrelated Donor Stem Cell Transplantation: a Single Center Study Hematopoietic stem-cell transplantation with HLA-DPB1 mismatched donors leads to an increased risk of acute graft-versus-host disease (aGVHD). Studies have indicated a potential prognostic value for classifying HLA-DPB1 mismatches based on T-cell-epitope (TCE) groups.

To determine whether non-permissiveness of HLA-DPB1 mismatches can be explained by indirect recognition of HLA-derived epitopes, the number of Predicted Indirectly ReCognizable HLA-epitopes (PIRCHES) was determined for every transplant pair as described herein. Mismatches classified as GVH non-permissive by the TCE algorithm, correlated to higher numbers of HLA class-II presented PIRCHES (PIRCHE-II) compared to permissive mismatches (p=0.026), and there was a similar trend for PIRCHE-I with both GVH and HVG non-permissive mismatches (p=0.087 and p=0.061, respectively). Furthermore, patients with aGVHD grade II-IV had a trend for higher numbers of PIRCHE-I (p=0.050) compared to patients with grade I or no aGVHD.

The invention therefore provides an alternative explanation for non-permissiveness of certain HLA-DPB1 combinations, since higher numbers of PIRCHES are correlated to non-permissive mismatches. The data are summarized in Table 3.

been identified on an epidemiological basis, in relation to an increased risk of developing severe acute GvHD (Ref 4a). Previously described methods have however shown limited success. The present example demonstrates the relationships between the numbers of peptides derived from the recipients' mismatched-HLA molecules that can be presented by donor-recipient shared HLA, designated as Predicted Indirectly ReCognizable HLA-Epitopes (PIRCHES) and HSCT outcome.

Methods: We analyzed whether in silico prediction of the numbers of peptides derived from the recipients' mismatched-HLA molecules that can be presented by donor-recipient shared HLA, designated as Predicted Indirectly ReCognizable HLA-Epitopes (PIRCHES), correlate with HSCT outcome. We predicted PIRCHES presented on HLA class-I (PIRCHE-I) and -II (PIRCHE-II) for 909 recipients of a single HLA-mismatched unrelated donor (9/10) using HLA-A, -B, -C, -DRB1 and -DQB1 typings. To test whether PIRCHES could suffice as a donor selection tool, patients were divided into equal sized tertiles according to their PIRCHE score (low, mid and high). The clinical outcome of these groups was evaluated and compared to a reference group of patients transplanted with HLA-A, -B, -C, -DRB1 and -DQB1 matched donors (10/10, n=1847).

Results: Patients presenting low PIRCHE-I and -II had comparable overall survival rates as HLA-matched transplantations (HR 0.98, CI 0.81-1.19, p=0.812), whereas patients presenting mid or high PIRCHE-I and -II showed higher risk estimates when compared to HLA-matched transplantations (HR 1.23, CI 1.06-1.42, p=0.007). Similar observations were made for disease free survival (HR 1.15,

TABLE 3

| Outcome | PIRCHE-I p-value | PIRCHE-II p-value | PIRCHE-I > 3 | | | PIRCHE-II > 4 | | |
|---|---|---|---|---|---|---|---|---|
| | | | N events | OR | p-value | N events | OR | p-value |
| aGVHD | 0.05 | 0.29 | 19/44 | 2.45 (0.94-6.37) | 0.063 | 14/32 | 2.00 (0.79-5.08) | 0.142 |
| cGVHD | 0.69 | 0.21 | 3/43 | 0.88 (0.17-4.62) | 0.875 | 4/32 | 3.36 (0.58-19.53) | 0.157 |
| Rel/progr | 0.96 | 0.35 | 19/42 | 1.65 (0.66-4.15) | 0.201 | 10/32 | 0.54 (0.21-1.39) | 0.201 |
| Overall survival | 0.37 | 0.008 | 23/44 | 0.89 (0.37-2.12) | 0.787 | 22/32 | 2.80 (1.10-7.12) | 0.028 |

Example 5

Identifying Permissible HLA-Mismatches: Predicted Indirectly Recognizable HLA Epitopes Summary of Example 5:

Background: Alloreactivity after HLA-mismatched hematopoietic stem-cell transplantation (HSCT) has a major negative impact on clinical outcome. This impact is reflected by a significantly inferior overall survival (OS) in partially matched-unrelated donors (MUDs) compared to HLA-matched transplantations (matched for HLA-A, -B, -C, -DRB1, -DQB1) (Ref 1a). HLA-matched donors are not available for all patients; in 20-40% of the cases a single HLA-mismatched donor (a 9/10 match) is a potential alternative (Ref 3a). In such situations, definition of the best permissible mismatch could benefit clinical outcome. Previously, certain specific non-permissible mismatches have CI 1.00-1.32, p=0.044), transplant-related mortality (HR 1.36, CI 1.10-1.69, p=0.005), acute (HR 1.64, CI 1.35-2.00, p<0.001) and chronic graft-versus-host disease (HR 1.43, CI 1.10-1.86, p=0.008). In adults transplanted with an HLA-mismatched unrelated donor, PIRCHES correlate to overall survival. Donor selection based on PIRCHES, may provide survival prognoses for HLA-mismatched HSCT similar to that of HLA-matched HSCT.

Methods:

Study Population:

A total of 2756 patients transplanted for malignant diseases with MUDs at 29 German transplant centers were included in this analysis (Table 4). Of these, n=909 (33.0%) were transplanted with single HLA-mismatched donors (9/10). These patients formed the study group. The remainder of n=1847 (67.0%) were transplanted with HLA-identical unrelated donors (10/10) and were used as a control group. Patients with more than one HLA-mismatch were excluded. Data were collected according to EBMT guidelines.22 Patient age was median 52 years (range 18-76). Myeloablative conditioning (MAC) was used for n=1696 (61.5%), and reduced intensity conditioning (RIC) was used for n=1060 (38.5%) of the patients.23 Graft sources were bone marrow (n=269, 9.8%) and peripheral blood stem cells (PBSC, n=2487, 90.2%). All grafts were T-cell replete.

HLA Typing:

High resolution (4 digit) HLA-A, -B, -C, -DRB1 and -DQB1 typing was performed in all recipients and donors. Exons 2 and 3 were determined for HLA class-I alleles and exon 2 for HLA class-II alleles. Clinically relevant null-allele ambiguities (not-expressed alleles) were excluded in accordance with NMDP (National Marrow Donor Program) requirements (Ref 24c). Both allele and antigen mismatches were classified as HLA mismatch, without considering the vector of mismatches (Ref 25c, 26c). For the determination of PIRCHES, complete sequences of exon 1-7 for HLA class I and exon 1-6 for HLA class II are preferred. For most HLA alleles in our cohort, these complete sequences are available (Ref 15c). Sequences that were not completely available were estimated based on a nearest neighbor principle.

Identification of PIRCHES:

PIRCHES were identified for each donor-recipient pair.

PIRCHE-I were identified in two steps. First, proteasome-mediated cleavage and transportation via the TAP channel were predicted for all donor and recipient HLA molecules using NetChop C-term 3.0.16 (Ref 19a). Subsequently, peptides with a processing probability >0.5 were tested for their binding capacity to the HLA-A, -B and -C molecules that were shared between the donor and recipient, using NetMHCpan 2.4 (Ref 21a, 20a). Only nonameric peptides with IC50-binding values ≤500 nM were accepted as relevant binders. This IC50 value is a commonly accepted cut-off value for HLA class I-binding peptides (Ref 22a).

For PIRCHE-II, the nonameric binding cores of potential 15-meric HLA-DRB1 binders were predicted with NetMHCIIPan 2.0 (Ref 23a, 24a) considering IC50-binding values ≤1000 nM as being relevant (Ref 25a). Based on thymic education, per presenting shared-HLA molecule, predicted binders derived from donor-HLA molecules were regarded as donor-self peptides and thus excluded from the recipient-specific PIRCHE repertoire. For each donor-recipient pair, the total number of PIRCHE-I and -II was counted separately.

Terminology for Example 5:

OS was defined as the probability of survival, independent of disease state at any point in time. Patients alive at last follow-up were censored. Disease free survival (DFS) is defined as the probability of being alive and free of disease at any time-point of follow-up. Patients alive at their last follow-up were censored. Transplant-related mortality (TRM) is defined as mortality incidence without previous relapse of disease. Relapse is treated as a competing event. Grading of acute GvHD was defined according to international consensus and chronic GvHD was defined according to the Seattle criteria (Ref 31c, 32c) Relapse incidence (RI) is defined as the probability of relapse at any given time-point with death from any other cause treated as competing event.

Statistical Analysis:

Univariate analysis of the effect of PIRCHES on OS and DFS was performed using Kaplan-Meier analysis and logrank testing. Multivariate analysis was carried out using extended Cox regression models, which allowed modeling of time-dependent effects. RI, TRM and chronic GvHD were analyzed using competing risk analysis. Analysis of GvHD has been performed on a subset of patients with complete data and follow-up of at least 100 days. Logistic regression was used for analysis of acute GvHD. Stratification was used to account for heterogeneity of diagnosis. A center effect was adjusted using a gamma-frailty term (Ref 33c). Statistical models evaluated the following clinical predictors: patient age, disease stage, time to transplantation, donor-recipient gender combination, donor-recipient KIR ligand status, patient and donor CMV status, year of transplantation, conditioning regimen intensity, donor origin (national vs. international), stem-cell source (bone marrow versus PBSC) and treatment with antithymocyte globulin (ATG) (Ref 23c). CMV status and treatment with ATG values were missing in n=727 (26.4%) and n=537 (19.5%) of the cases, respectively. Models were cross-validated by inclusion of missing cases as separate group as well as by omission of cases with missing values (Ref 34c). During crossvalidation, no bias was found. PIRCHE values of single mismatched transplantations were divided in equal sized tertiles and outcome was correlated to the respective groups as well as to the control group of 10/10-matched transplantations. All models were checked for proportional hazards assumption and no violations were found. Statistical significance was set to p=0.05. All statistical procedures were performed with R, version 3.0.1.

Results:

Patient and Donor Characteristics:

Characteristics of the 909 patients transplanted with a 9/10 unrelated donor and the 1847 controls transplanted with an HLA-identical donor are listed in Table 4. Patients that received a single HLA-mismatched donor were generally transplanted with more favorable factors compared to 10/10 transplantations; patients in the 9/10 group were younger, had received more frequent RIC regimens, less PBSC, and less gender-mismatched transplants (female donor to male recipient). However, 10/10 matched HSCTs were performed more recently than 9/10s (Table 4).

TABLE 4

Patient characteristics of 9/10 and 10/10 groups. Patients in the 9/10 groups were generally transplanted with more favorable characteristics: they were younger, had received more frequent RIC regimens, less PBSC, and less gender-mismatched transplants (female donor to male recipient).

|  | 10/10 Match n (%) | 9/10 Match n (%) | p-value |
|---|---|---|---|
| Number of Patients | 1847 | 909 |  |
| Age median (range) | 53 (18-76) | 51 (18-75) | 0.013 |
| Diagnosis |  |  |  |
| AML | 560 (30.3) | 275 (30.3) | 0.268 |
| ALL | 215 (11.6) | 123 (13.5) |  |
| AL | 113 (6.1) | 46 (5.1) |  |
| CML | 102 (5.5) | 64 (7.0) |  |
| CLL | 91 (4.9) | 43 (4.7) |  |
| MDS | 358 (19.4) | 181 (19.9) |  |
| NHL | 250 (13.5) | 99 (10.9) |  |
| MM | 158 (8.6) | 78 (8.6) |  |
| Disease stage |  |  |  |
| Early | 737 (39.9) | 371 (40.8) | 0.602 |
| Intermediate | 649 (35.1) | 302 (33.2) |  |
| Advanced | 461 (25.0) | 236 (26.0) |  |
| Conditioning regimen |  |  |  |
| Myeloablative | 1109 (60.0) | 587 (35.4) | 0.024 |
| Reduced intensity | 738 (40.0) | 322 (64.6) |  |

TABLE 4-continued

Patient characteristics of 9/10 and 10/10 groups. Patients in the 9/10 groups were generally transplanted with more favorable characteristics: they were younger, had received more frequent RIC regimens, less PBSC, and less gender-mismatched transplants (female donor to male recipient).

|  | 10/10 Match n (%) | 9/10 Match n (%) | p-value |
|---|---|---|---|
| Stem cell source | | | |
| BM | 148 (8.0) | 121 (13.3) | <0.001 |
| PBSC | 1699 (92.0) | 788 (86.7) | |
| Donor-recipient sex match | | | |
| male-male | 906 (49.1) | 398 (43.8) | <0.001 |
| male-female | 203 (11.0) | 147 (16.2) | |
| female-male | 498 (27.0) | 216 (23.8) | |
| female-female | 240 (13.0) | 148 (16.3) | |
| Year of transplanation | | | |
| 1997-2003 | 173 (9.4) | 154 (16.9) | <0.001 |
| 2004-2007 | 543 (29.4) | 289 (31.8) | |
| 2008-2011 | 1131 (61.2) | 466 (51.3) | |

AML = acute myeloid leukemia,
ALL = acute lymphoblastic leukemia,
AL = unclassified acute leukemia,
CML = chronic myeloid leukemia,
CLL = chronic lymphocytic leukemia,
MDS = myelodysplastic syndrome,
NHL = Non-Hodgkin-Lymphoma,
MM = multiple Myeloma,
BM = bone marrow,
PBSC = periperal blood stem cells.

Patients transplanted with an HLA-mismatched donor presented 0-31 PIRCHE-I and 0-79 PIRCHE-II. To analyze the effect of PIRCHES, patients were divided amongst three equal groups: presenting low, intermediate (mid) or high PIRCHES, according to the observed tertiles, as listed in Table 5. Classification into these three PIRCHE groups was correlated to clinical outcome in the entire study.

TABLE 5

Distribution of PIRCHES scores To analyze the effect of PIRCHES, patients were divided amongst three equal groups: presenting low, intermediate (mid) or high PIRCHES, according to the observed tertiles

| PIRCHES I or II scores | | n | % |
|---|---|---|---|
| PIRCHE-I low | 0-1 | 397 | 43.7 |
| PIRCHE-I mid | 2-4 | 221 | 23.3 |
| PIRCHE-I high | 5-31 | 291 | 32.0 |
| PIRCHE-II low | 0-3 | 326 | 35.9 |
| PIRCHE-II mid | 4-13 | 284 | 31.2 |
| PIRCHE-II high | 14-79 | 299 | 32.9 | low, mid, high: equal sized tertile grouping according to PIRCHES score,
n = number of patients,
% = percentage within HLA mismatched group The Effects of PIRCHES on Survival:

To analyze the effect of PIRCHES on clinical outcome, we first tested differences in OS and DFS rates of the PIRCHE tertiles. Low PIRCHES were significantly correlated to improved OS and DFS when compared to higher (mid and high combined) PIRCHES (FIG. 7; see table 7 below). To analyze the effect of PIRCHES with respect to an HLA-matched situation, we next compared the PIRCHES tertiles with the 10/10 group. Patients presenting low PIRCHE-I or -II had similar OS and DFS rates as patients transplanted with a 10/10 MUD. However, both mid and high PIRCHE-I and -II had significantly reduced OS and DFS rates when compared to 10/10 matches (FIG. 7AB, Table 6).

TABLE 6A and 6B

Univariate analyses of OS, DFS and TRM for the PIRCHES groups compared to 10/10 HSCT. Patients in the low PIRCHE-I and -II groups had similar OS, DFS and TRM rates compared to 10/10 s. Patients in the mid and high PIRCHE-I and -II groups had significantly reduced OS and DFS and significantly increased TRM compared to 10/10 s.

Table 6A: Survival Rates according to PIRCHE scores

| | OS | | | |
|---|---|---|---|---|
| | 1 year | 3 year | 5 year | p-value |
| 10/10 | 0.62 (0.59-0.65) | 0.46 (0.43-0.50) | 0.42 (0.39-0.46) | |
| PIRCHE-I low | 0.54 (0.48-0.60) | 0.45 (0.39-0.52) | 0.40 (0.33-0.48) | 0.213 |
| PIRCHE-I mid | 0.52 (0.47-0.58) | 0.42 (0.37-0.48) | 0.37 (0.31-0.44) | 0.027 |
| PIRCHE-I high | 0.47 (0.41-0.54) | 0.34 (0.28-0.41) | 0.32 (0.26-0.39) | <0.001 |
| PIRCHE-II low | 0.54 (0.48-0.60) | 0.46 (0.40-0.53) | 0.40 (0.33-0.48) | 0.355 |
| PIRCHE-II mid | 0.50 (0.44-0.56) | 0.37 (0.31-0.43) | 0.33 (0.27-0.40) | 0.077 |
| PIRCHE-II high | 0.50 (0.44-0.56) | 0.39 (0.34-0.46) | 0.36 (0.30-0.43) | 0.003 |

Table 6B: Survival Rates according to PIRCHE scores

| | DFS | | | | TRM | |
|---|---|---|---|---|---|---|
| | 1 year | 3 year | 5 year | p-value | 1 year | p-value |
| 10/10 | 0.52 (0.49-0.55) | 0.37 (0.34-0.41) | 0.31 (0.29-0.35) | | 0.20 (0.18-0.23) | |
| PIRCHES I low | 0.45 (0.39-0.52) | 0.38 (0.32-0.44) | 0.32 (0.26-0.40) | 0.498 | 0.25 (0.20-0.31) | 0.112 |
| PIRCHES I mid | 0.43 (0.38-0.49) | 0.33 (0.28-0.40) | 0.26 (0.21-0.33) | 0.084 | 0.29 (0.24-0.34) | 0.002 |
| PIRCHES I high | 0.41 (0.36-0.48) | 0.27 (0.22-0.33) | 0.22 (0.16-0.28) | 0.003 | 0.30 (0.24-0.36) | 0.003 |
| PIRCHES II low | 0.47 (0.41-0.53) | 0.39 (0.33-0.46) | 0.32 (0.26-0.39) | 0.833 | 0.24 (0.19-0.29) | 0.281 |
| PIRCHES II mid | 0.40 (0.35-0.47) | 0.30 (0.24-0.36) | 0.25 (0.20-0.32) | 0.012 | 0.31 (0.25-0.36) | <0.001 |
| PIRCHES II high | 0.43 (0.37-0.49) | 0.30 (0.24-0.36) | 0.23 (0.18-0.30) | 0.010 | 0.29 (0.24-0.34) | 0.002 |

OS = Overall Survival, confidence interval in parentheses, log rank p-value compares the PIRCHES groups against the 10/10 matched reference group, significant results in bold.
DFS = Disease Free Survival, TRM = transplant-related mortality, confidence interval in parentheses, log rank p-value compares the PIRCHES groups against the 10/10 matched reference group, significant results in bold.

In multivariate analysis, patients with mid or high PIRCHE-I have a significantly increased hazard of OS and DFS when compared to low PIRCHE-I (OS: HR 1.21, CI 1.00-1.46, p=0.049, DFS: HR 1.22, CI 1.03-1.45, p=0.024). This was not observed when comparing the PIRCHE-II groups. When compared to 10/10 matched transplantations, patients presenting low PIRCHE-I and -II had similar OS and DFS rates. However, significantly higher overall mortality was observed for patients in the PIRCHE-I mid, high as well as PIRCHE-II mid groups (FIG. 8AB). Mid and high PIRCHES also correlated to a higher risk of DFS when compared to 10/10s, but only in the PIRCHE-I mid group statistical significance was reached.

In univariate analysis of TRM, PIRCHE-I and -II higher had significantly higher incidences of TRM compared to PIRCHE-I and -II low (see table 6B). When compared to completely matched transplantations, the PIRCHE-I and -II low groups had similar TRM incidences, while the PIRCHE-I and PIRCHE-II mid and high groups had statistically significant higher incidences of TRM compared to completely matched transplantations (FIG. 9, Table 6). Multivariate comparison between low and higher PIRCHE-I showed a trend towards an increased risk of TRM for the higher PIRCHE-I values (HR 1.26, CI 0.96-1.65, p=0.090). A similar finding was obtained when comparing PIRCHE-II low with higher values (HR 1.28, CI 0.97-1.70, p=0.082). When PIRCHE groups were compared to the 10/10 situation, PIRCHE-I and -II mid and high values associated with higher risk of TRM (FIG. 8C).

TABLE 7

PIRCHES I and II interaction models

| | Match Category | n events/n at risk | HR | CI | p-value |
|---|---|---|---|---|---|
| OS | 10/10 | 571/1307 | 1.00 | | |
| | PI low, PII low | 100/215 | 1.00 | 0.80-1.25 | 0.988 |
| | PI/II higher | 376/694 | 1.20 | 1.05-1.38 | 0.009 |
| DFS | 10/10 | 571/1307 | 1.00 | | |
| | PI low, PII low | 120/215 | 0.94 | 0.77-1.15 | 0.537 |
| | PI/II higher | 438/694 | 1.12 | 0.99-1.27 | 0.074 |
| TRM | 10/10 | 236/1307 | 1.00 | | |
| | PI low, PII low | 42/215 | 0.97 | 0.68-1.37 | 0.857 |
| | PI/II higher | 187/694 | 1.35 | 1.10-1.66 | 0.004 |
| aGvHD | 10/10 | 269/926 | 1.00 | | |
| | PI low, PII low | 48/149 | 1.14 | 0.83-1.55 | 0.420 |
| | PI/II higher | 187/488 | 1.38 | 1.15-1.67 | <0.001 |
| cGvHD | 10/10 | 185/535 | 1.00 | | |
| | PI low, PII low | 28/84 | 0.94 | 0.62-1.42 | 0.752 |
| | PI/II higher | 120/269 | 1.36 | 1.05-1.76 | 0.021 |

The Effects of PIRCHES on Graft-Versus-Host Disease:

The analysis of acute and chronic GvHD was performed on a subset of patients with follow-up of at least 100 days (n=2054, 74.5%). Within the HLA-mismatched group, higher PIRCHE-I and -II values compared to low PIRCHE-I or -II values associated with statistically significant increased odds of acute GvHD (OR 1.68, CI 1.27-2.21, p=0.001, OR 1.33, CI 1.01-1.75, p=0.045 for PIRCHE-I and -II respectively). Furthermore, higher PIRCHE-I showed an increased risk for development of chronic GvHD compared to low PIRCHE-I (HR 1.47, 1.06-2.06, p=0.022, whereas this effect was not found for PIRCHE-II values (HR 1.18, 0.84-1.66, p=0.344).

Patients in the low PIRCHE-I and -II groups had similar rates of both acute and chronic GvHD as 10/10-matched transplantations, while the PIRCHE-I and -II high groups showed a significantly increased risk of acute and chronic GvHD (FIG. 8DE).

PIRCHE-I and -II Values for Optimal Donor Selection:

Donor selection based upon PIRCHES may lead to options with either low PIRCHE-I and high PIRCHE-II or vice versa. To analyze the effects of the different combinations of PIRCHE groups, interaction models were formed and correlated with OS. To reduce the number of subgroups, PIRCHES mid and high tertiles were combined in a higher group. Patients with both low PIRCHE-I and PIRCHE-II values showed the lowest risk estimates, similar to 10/10 matched transplantations (n=288, HR 0.98, CI 0.81-1.19, p=0.817). Most combinations involving mid and high PIRCHES values showed somewhat higher risk estimates, especially the combinations with higher PIRCHE-I, as higher PIRCHE-I with low PIRCHE-II was also clearly associated with an increased risk of overall mortality (HR 1.73, CI 1.14-2.62, p=0.010, FIG. 8A, FIG. 10).

Discussion of Example 5:

In a large cohort, we demonstrate that higher numbers of indirectly recognizable HLA epitopes, PIRCHES, are associated with detrimental HSCT outcome. More importantly, we demonstrate that HSCT with low numbers of PIRCHES leads to clinical outcomes similar to that observed after completely HLA-matched HSCT (FIG. 8).

Low PIRCHE-I and -II are associated with similar risks of overall mortality, DFS, TRM, acute and chronic GvHD as 10/10 matched HSCT. PIRCHE-I and -II were not associated with relapse (FIG. 11). Therefore, PIRCHES may facilitate selection procedures involving HLA-mismatched donors by selecting a priori donors with similar prognoses as when the patient would be transplanted with an HLA-identical unrelated donor. Especially donor-recipient combinations in the low PIRCHE-I group are favourable: these combinations have a significantly increased probability of OS an DFS, and show a decreased risk of acute and chronic GvHD compared to patients in the higher PIRCHE-I groups. This relative importance of PIRCHE-I is also reflected by the results of interaction analyses: patients in the higher PIRCHE-I groups seem to have reduced OS rates when combined with either low or higher PIRCHE-II.

To evaluate the effect of PIRCHES relative to 10/10-matched HSCT, the PIRCHE groups were compared to a control group of HLA-matched transplantations. This control group was not matched on baseline characteristics, but rather a complete selection from the overall cohort of unrelated-donor transplantations. Therefore, baseline characteristics differed between 9/10 and 10/10 HSCT (Table 4). All these baseline factors were analyzed for their correlation to clinical outcome, and added to the multivariate models when associated with outcome. A similar strategy was also performed comparing the baseline characteristics amongst the PIRCHE groups (Tables 8A, 8B).

TABLE 8

Patient characteristics in PIRCHE-I and PIRCHE-II groups.

Table 8A:
Patient characteristics PIRCHE-I groups

| | PIRCHE-I | | | |
| --- | --- | --- | --- | --- |
| | low | mid | high | p-value |
| Number of Patients | 397 | 221 | 291 | |
| Age median (range) | 51 (18-75) | 51 (18-72) | 52 (18-74) | 0.07 |
| Diagnosis (%) | | | | |
| AML | 118 (29.7) | 67 (30.3) | 90 (30.9) | 0.366 |
| ALL | 48 (12.1) | 32 (14.5) | 43 (14.8) | |
| AL | 16 (4.0) | 12 (5.4) | 18 (6.2) | |
| CML | 34 (8.6) | 14 (6.3) | 16 (5.5) | |
| CLL | 16 (4.0) | 15 (6.8) | 12 (4.1) | |
| MDS | 77 (19.4) | 46 (20.8) | 58 (19.9) | |
| NHL | 46 (11.6) | 24 (10.9) | 29 (10.0) | |
| MM | 42 (10.6) | 11 (5.0) | 25 (8.6) | |
| Disease stage | | | | |
| Early | 160 (40.3) | 93 (42.1) | 118 (40.5) | 0.750 |
| Intermediate | 141 (35.5) | 66 (29.9) | 95 (32.6) | |
| Advanced | 96 (24.2) | 62 (28.1) | 78 (26.8) | |
| Conditioning regimen | | | | |
| Myeloablative | 236 (59.4) | 159 (71.9) | 192 (66.0) | 0.002 |
| Reduced intensity | 161 (40.6) | 62 (28.1) | 99 (34.0) | |
| Stem cell source | | | | |
| BM | 48 (12.3) | 28 (12.7) | 44 (15.1) | <0.001 |
| PBSC | 348 (87.7) | 193 (87.3) | 247 (84.9) | |
| Donor-recipient sex match | | | | |
| male-male | 174 (49.1) | 98 (44.3) | 126 (43.3) | <0.001 |
| male-female | 62 (15.6) | 32 (14.5) | 53 (18.2) | |
| female-male | 102 (25.7) | 53 (24.0) | 61 (21.0) | |
| female-female | 59 (14.9) | 38 (17.2) | 51 (17.5) | |
| Year of transplantation | | | | |
| 1997-2003 | 74 (18.6) | 36 (16.3) | 44 (15.1) | <0.001 |
| 2004-2007 | 142 (35.8) | 69 (31.2) | 78 (26.8) | |
| 2008-2011 | 181 (45.6) | 116 (52.5) | 169 (58.1) | |

Table 8B:
Patient characteristics PIRCHE-II groups

| | PIRCHE-II | | | |
| --- | --- | --- | --- | --- |
| | low | mid | high | p-value |
| Number of Patients | 326 | 284 | 299 | |
| Age median (range) | 50 (18-72) | 53 (19-72) | 52 (18-75) | 0.005 |
| Diagnosis (%) | | | | |
| AML | 99 (30.4) | 75 (26.4) | 101 (33.8) | 0.268 |
| ALL | 45 (13.8) | 33 (11.6) | 45 (15.1) | |
| AL | 18 (5.5) | 17 (6.0) | 11 (3.7) | |
| CML | 27 (8.3) | 22 (7.7) | 15 (5.0) | |
| CLL | 14 (4.3) | 16 (5.6) | 13 (4.3) | |
| MDS | 59 (18.1) | 60 (21.1) | 62 (20.7) | |
| NHL | 33 (10.1) | 31 (10.9) | 35 (11.7) | |
| MM | 31 (9.5) | 30 (10.6) | 17 (5.7) | |
| Disease stage | | | | |
| Early | 133 (40.8) | 113 (39.8) | 125 (41.8) | 0.872 |
| Intermediate | 113 (34.7) | 97 (34.2) | 92 (30.8) | |
| Advanced | 80 (24.5) | 74 (26.1) | 82 (27.4) | |
| Conditioning regimen | | | | |
| Myeloablative | 211 (64.7) | 177 (62.3) | 199 (66.6) | 0.094 |
| Reduced intensity | 115 (35.3) | 107 (37.7) | 100 (33.4) | |
| Stem cell source | | | | |
| BM | 46 (14.1) | 35 (12.3) | 40 (13.4) | <0.001 |
| PBSC | 280 (85.9) | 249 (87.7) | 259 (86.6) | |

TABLE 8-continued

Patient characteristics in PIRCHE-I and PIRCHE-II groups.

| Donor-recipient sex match | | | | |
|---|---|---|---|---|
| male-male | 144 (44.2) | 108 (38.0) | 146 (48.8) | 0.001 |
| male-female | 52 (16.0) | 47 (16.5) | 48 (16.1) | |
| female-male | 83 (25.5) | 73 (25.7) | 60 (20.1) | |
| female-female | 47 (14.4) | 56 (19.7) | 45 (15.1) | |
| Year of transplantation | | | | |
| 1997-2003 | 65 (19.9) | 48 (16.9) | 41 (13.7) | <0.001 |
| 2004-2007 | 115 (35.3) | 87 (30.6) | 87 (29.1) | |
| 2008-2011 | 146 (44.8) | 149 (52.5) | 171 (57.2) | |

AML = acute myeloid leukemia,
ALL = acute lymphoblastic leukemia,
AL = unclassified acute leukemia,
CML = chronic myeloid leukemia,
CLL = chronic lymphocytic leukemia,
MDS = myelodysplastic syndrome,
NHL = Non-Hodgkin-Lymphoma,
MM = multiple Myeloma,
BM = bone marrow,
PBSC = periperal blood stem cells.

The relevance of HLA-DQB1 matching for outcome of HSCT has previously been considered controversial (Ref 25c). HLADQB1 mismatches were included in this example as they were associated with increased mortality in a previous analysis of this cohort (Ref 23c). Interestingly, HLA-DQB1 antigenic mismatches, lead to the highest numbers of both PIRCHE-I and -II in this cohort, when compared to other loci (data not shown). This shows why HLA-DQB1 mismatches in this cohort are associated with adverse events.

The availability of the entire sequence is preferred to most accurately estimate the risk of alloreactivity due to indirect recognition. As mentioned in the methods section, in this example, incomplete sequences were complemented based on similarities between alleles. The predictive potential of PIRCHES may be improved when these sequences are elucidated in full. Thus, our study underlines the preference for complete sequencing of exon 1-7 of all HLA class-I alleles and exon 1-6 for all HLA class-II alleles, when describing new HLA alleles.

Since HLA mismatched HSCT is highly correlated to an increased risk of adverse events, HSCT is frequently not performed for patients for whom only an HLA-mismatched donor is available, especially for patients with non-malignant diseases. For these patients, an alternative stem cell source can be a single or double cord blood (CB) unit, since for CB transplantation HLA match criteria are less stringent (Ref 36c). However, for patients with non-malignant diseases, sustained engraftment of the CB can be problematic, with graft-failure rates reported up to 90% (Ref 37c). The results of this example therefore suggest that selecting HLA-mismatched unrelated adult donors with a low number of PIRCHES lead to a reduction in complications. Therefore, patients with non-malignant bone marrow diseases can potentially be transplanted with HLA-mismatched donors, with similar prognoses as for HLA-matched donors.

In summary, example 5 demonstrates that PIRCHES correlate with clinical alloreactivity. In particular, patients presenting low PIRCHE-I have similar clinical outcomes as patients transplanted with an HLA-matched donor. Our data thus suggest that indirect recognition of mismatched-HLA by T cells is an important mechanism in clinical alloreactivity after HLAmismatched HSCT. Determining the number of PIRCHES for potential donors prior to HSCT may allow reducing complications after HLA-mismatched HSCT by avoiding donors that can recognize higher numbers of PIRCHES. The present results indicate that selection of HLA mismatched donors with low numbers of PIRCHES may lead to 5-year survival probabilities similar to completely HLA-matched donors.

Example 6

Method for Screening Suitable Donor Material with Permissible Mismatches; HSCT Transplantation The following steps are conducted in order to screen and select suitable donor material for HSCT:
1. Perform high resolution typing for the recipient for at least HLA-A, -B, -C, DRB1, and -DQB1.
2. Perform high resolution typing for preferably multiple donors for at least HLA-A, -B, -C, DRB1, and -DQB1, or theoretically determine the expected high resolution typing of potential 9/10 matched unrelated donors.
3. Enter the obtained HLA-typing data into the computer program, which has been designed to execute the method of the present invention.
4. The program will subsequently, preferably automatically, calculate the total number of PIRCHE, the number of PIRCHE-I and the number of PIRCHE-II (see below for an example of the output data from the DNA typing and subsequent determination of PIRCHE).
5. With the given output, risk estimates can be obtained for the various outcomes on the basis of the data demonstrated in FIG. 8 and selection can be based upon the lowest risk, as assessed by the method, and corresponding software, disclosed herein.

| >> DNA TYPING | | | | | |
|---|---|---|---|---|---|
| Name | HLA-A | -B | -C | -DRB1 | -DQB1 |
| Recipient | *01:01 | *07:02 | *07:01 | *03:01 | *02:01 |
|  | *11:01 | *08:01 | *07:04 | *11:01 | *03:01 |
| Expected donor 1 (BMDW) | *01:01 | *07:02 | *07:01 | *03:01 | *02:01 |
|  | *11:01 | *08:01 | *07:02 | *11:01 | *03:01 |
| Expected donor 2 (BMDW) | *01:01 | *44:02 | *07:01 | *03:01 | *02:01 |
|  | *11:01 | *08:01 | *07:04 | *11:01 | *03:01 |

| >> DNA TYPING | | | |
|---|---|---|---|
| PIRCHE Scores | PIRCHE-I | PIRCHE-II | PIRCHE (total) |
| Expected donor 1 | 0 | 7 | 7 |
| Expected donor 2 | 2 | 2 | 4 |

| >> DNA TYPING | | | | | |
|---|---|---|---|---|---|
| Name | HLA-A | -B | -C | -DRB1 | -DQB1 |
| Recipient | 02:01 | 08:01 | 07:02 | 03:01 | 02:01 |
|  | 24:02 | 15:18 | 07:04 | 11:03 | 03:01 |
| Expected donor 1 | 02:01 | 08:01 | 07:01 | 03:01 | 02:01 |
|  | 24:02 | 15:18 | 07:04 | 11:03 | 03:01 |
| PIRCHE Scores | PIRCHE-I | PIRCHE-II | PIRCHE (total) | | |
| Observed donor | 0 | 1 | 1 | | |

As can be seen from the examples disclosed herein, the method as described enables an effective, preferably automated and/or computer-implemented, method for assessing the likelihood of an immune reaction, preferably in advance of the transplantation. The method thereby enables a method for selecting mismatched donor material that will effectively show the same risk of alloreactivity as a fully matched donor.

REFERENCES

1a. Gupta V, et al. Comparable survival after HLA-well-matched unrelated or matched sibling donor transplantation for acute myeloid leukemia in first remission with unfavorable cytogenetics at diagnosis. *Blood* 2010; 116: 1839-48.

2a. Kawase T, Matsuo K, Kashiwase K, Inoko H, Saji H, Ogawa S, Kato S, Sasazuki T, Kodera Y, Morishima Y. HLA mismatch combinations associated with decreased risk of relapse: implications for the molecular mechanism. *Blood* 2009; 113: 2851-58.

3a. Hurley C K, Fernandez-Vina M, Hildebrand W H, Noreen H J, Trachtenberg E, Williams T M, Baxter-Lowe L A, Begovich A B, Petersdorf E, Selvakumar A, Stastny P, Hegland J, Hartzman R J, Carston M, Gandham S, Kollman C, Nelson G, Spellman S, Setterholm M. A high degree of HLA disparity arises from limited allelic diversity: analysis of 1775 unrelated bone marrow transplant donor-recipient pairs. *Hum. Immunol.* 2007; 68: 30-40.

4a. Kawase T, Morishima Y, Matsuo K, Kashiwase K, Inoko H, Saji H, Kato S, Juji T, Kodera Y, Sasazuki T. High-risk HLA allele mismatch combinations responsible for severe acute graft-versus-host disease and implication for its molecular mechanism. *Blood* 2007; 110: 2235-41.

5a. Spencer A, Brookes P A, Kaminski E, Hows J M, Szydlo R M, van RF, Goldman J M, Batchelor J R. Cytotoxic T lymphocyte precursor frequency analyses in bone marrow transplantation with volunteer unrelated donors. Value in donor selection. *Transplantation* 1995; 59: 1302-8.

6a. Duquesnoy R J, Marrari M. HLAMatchmaker: a molecularly based algorithm for histocompatibility determination. II. Verification of the algorithm and determination of the relative immunogenicity of amino acid triplet-defined epitopes. *Hum. Immunol.* 2002; 63: 353-63.

7a. Duquesnoy R J, Takemoto S, de LP, Doxiadis I I, Schreuder G M, Persijn G G, Claas F H. HLAmatchmaker: a molecularly based algorithm for histocompatibility determination. III. Effect of matching at the HLA-A,B amino acid triplet level on kidney transplant survival. *Transplantation* 2003; 75: 884-89.

8a. Duquesnoy R, Spellman S, Haagenson M, Wang T, Horowitz M M, Oudshoorn M. HLAMatchmaker-defined triplet matching is not associated with better survival rates of patients with class I HLA allele mismatched hematopoietic cell transplants from unrelated donors. *Biol. Blood Marrow Transplant.* 2008; 14: 1064-71.

9a. Amir A L, van der Steen D M, Hagedoorn R S, Kester M G, van Bergen C A, Drijfhout J W, de Ru A H, Falkenburg J H, van Veelen P A, Heemskerk M H. Allo-HLA-reactive T cells inducing graft-versus-host disease are single peptide specific. *Blood* 2011; 118: 6733-42.

10a. Elsner H A, DeLuca D, Strub J, Blasczyk R. Histo-Check: rating of HLA class I and II mismatches by an internet-based software tool. *Bone Marrow Transplant.* 2004; 33: 165-69

11a. Spellman S, Klein J, Haagenson M, Askar M, Baxter-Lowe L A, He J, Hsu S, Blasczyk R, Hurley C. Scoring HLA Class I Mismatches by HistoCheck Does Not Predict Clinical Outcome in Unrelated Hematopoietic Stem Cell Transplantation. *Biol. Blood Marrow Transplant.* 2011.

12a. Askar M, Sobecks R, Morishima Y, Kawase T, Nowacki A, Makishima H, Maciejewski J. Predictions in the face of clinical reality: HistoCheck versus high-risk HLA allele mismatch combinations responsible for severe acute graft-versus-host disease. *Biol. Blood Marrow Transplant.* 2011; 17: 1409-15.

13a. Akatsuka Y, et al. Disparity for a newly identified minor histocompatibility antigen, HA-8, correlates with acute graft-versus-host disease after haematopoietic stem cell transplantation from an HLA-identical sibling. *Br. J. Haematol.* 2003; 123: 671-75.

14a. Randolph S S, Gooley T A, Warren E H, Appelbaum F R, Riddell S R. Female donors contribute to a selective graft-versus-leukemia effect in male recipients of HLA-matched, related hematopoietic stem cell transplants. *Blood* 2004; 103: 347-52.

15a. Mutis T, Brand R, Gallardo D, van B A, Niederwieser D, Goulmy E. Graft-versus-host driven graft-versus-leukemia effect of minor histocompatibility antigen HA-1 in chronic myeloid leukemia patients. *Leukemia* 2010; 24: 1388-92.

16a. van D S, Pietersma F, Wolfl M, Verdonck L F, Petersen E J, Lokhorst H M, Martens E, Theobald M, van B D, Meijer E, Kuball J. Rituximab treatment before reduced-intensity conditioning transplantation associates with a decreased incidence of extensive chronic GVHD. *Biol. Blood Marrow Transplant.* 2009; 15: 671-78.

17a. Maiers M, Gragert L, Klitz W. High-resolution HLA alleles and haplotypes in the United States population. *Hum. Immunol.* 2007; 68: 779-88.

18a. Kesmir C, Nussbaum A K, Schild H, Detours V, Brunak S. Prediction of proteasome cleavage motifs by neural networks. *Protein Eng* 2002; 15: 287-96.

19a. Nielsen M, Lundegaard C, Lund O, Kesmir C. The role of the proteasome in generating cytotoxic T-cell epitopes: insights obtained from improved predictions of proteasomal cleavage. Immunogenetics 2005; 57: 33-41.

20a. Nielsen M, Lundegaard C, Blicher T, Lamberth K, Harndahl M, Justesen S, Roder G, Peters B, Sette A, Lund O, Buus S. NetMHCpan, a method for quantitative predictions of peptide binding to any HLA-A and -B locus protein of known sequence. *PLoS. One.* 2007; 2: e796.

21a. Hoof I, Peters B, Sidney J, Pedersen L E, Sette A, Lund O, Buus S, Nielsen M. NetMHCpan, a method for MHC class I binding prediction beyond humans. *Immunogenetics* 2009; 61: 1-13.

22a. Buus S, Lauemoller S L, Worning P, Kesmir C, Frimurer T, Corbet S, Fomsgaard A, Hilden J, Holm A, Brunak S. Sensitive quantitative predictions of peptide-MHC binding by a 'Query by Committee' artificial neural network approach. *Tissue Antigens* 2003; 62: 378-84.

23a. Nielsen M, Lundegaard C, Lund O. Prediction of MHC class II binding affinity using SMM-align, a novel stabilization matrix alignment method. *BMC. Bioinformatics.* 2007; 8: 238.

24a. Nielsen M, Lund O. N N-align. An artificial neural network-based alignment algorithm for MHC class II peptide binding prediction. *BMC. Bioinformatics.* 2009; 10: 296.

25a. Southwood S, Sidney J, Kondo A, del Guercio M F, Appella E, Hoffman S, Kubo R T, Chesnut R W, Grey H M, Sette A. Several common HLA-D R types share largely overlapping peptide binding repertoires. *J. Immunol.* 1998; 160: 3363-73.

26a. Ferrara J L, Levine J E, Reddy P, Holler E. Graft-versus-host disease. *Lancet* 2009; 373: 1550-1561.

27a. Jeras M. The role of in vitro alloreactive T-cell functional tests in the selection of HLA matched and mismatched haematopoietic stem cell donors. *Transpl. Immunol.* 2002; 10: 205-14.

28a. Chakraverty R, Sykes M. The role of antigen-presenting cells in triggering graft-versus-host disease and graft-versus-leukemia. *Blood* 2007; 110: 9-17.

29a. Flomenberg N, Baxter-Lowe L A, Confer D, Fernandez-Vina M, Filipovich A, Horowitz M, Hurley C, Kollman C, Anasetti C, Noreen H, Begovich A, Hildebrand W, Petersdorf E, Schmeckpeper B, Setterholm M, Trachtenberg E, Williams T, Yunis E, Weisdorf D. Impact of HLA class I and class II high-resolution matching on outcomes of unrelated donor bone marrow transplantation: HLA-C mismatching is associated with a strong adverse effect on transplantation outcome. *Blood* 2004; 104: 1923-30.

30a. Snary D, Barnstable C J, Bodmer W F, Crumpton M J. Molecular structure of human histocompatibility antigens: the HLA-C series. *Eur. J. Immunol.* 1977; 7: 580-585.

1b. Opelz G, Wujciak T, Dohler B, Scherer S, Mytilineos J. HLA compatibility and organ transplant survival. Collaborative Transplant Study. *Rev Immunogenet* 1999; 1: 334-342.

2b. Terasaki P I, Cai J. Human leukocyte antigen antibodies and chronic rejection: from association to causation. *Transplantation* 2008; 86: 377-383.

3b. Duquesnoy R J. HLAMatchmaker: a molecularly based algorithm for histocompatibility determination. I. Description of the algorithm. *Hum Immunol* 2002; 63: 339-352.

4b. Duquesnoy R J. A structurally based approach to determine HLA compatibility at the humoral immune level. *Hum Immunol* 2006; 67: 847-862.

5b. Duquesnoy R J. Antibody-reactive epitope determination with HLAMatchmaker and its clinical applications. *Tissue Antigens* 2011; 77: 525-534.

6b. Claas F H. Predictive parameters for in vivo alloreactivity. *Transpl Immunol* 2002; 10: 137-142.

7b. Fuller T C, Fuller A. The humoral immune response against an HLA class I allodeterminant correlates with the HLA-D R phenotype of the responder. *Transplantation* 1999; 68: 173-182.

8b. Papassavas A C, Barnardo M C, Bunce M, Welsh K I. Is there MHC Class II restriction of the response to MHC Class I in transplant patients? *Transplantation* 2002; 73: 642-651.

9b. Suciu-Foca N, Liu Z, Harris P E et al. Indirect recognition of native HLA alloantigens and Bcell help. *Transplant Proc* 1995; 27: 455-456.

10b. Peters B, Bui H H, Frankild S et al. A community resource benchmarking predictions of peptide binding to MHC-I molecules. *PLoS Comput Biol* 2006; 2: e65.

11b. Falk K, Rotzschke O, Stevanovic S, Jung G, Rammensee H G. Allele-specific motifs revealed by sequencing of self-peptides eluted from MHC molecules. *Nature* 1991; 351: 290-296

12b. Nielsen M, Lund O, Buus S, Lundegaard C. MHC class II epitope predictive algorithms. *Immunology* 2010; 130: 319-328.

6c. Heemskerk M B, Doxiadis I I, Roelen D L, Claas F H, Oudshoorn M. The HistoCheck algorithm does not predict T-cell alloreactivity in vitro. *Bone Marrow Transplant* 2005; 36(10):927-928.

7c. Shaw B E, Barber L D, Madrigal J A, Cleaver S, Marsh S G. Scoring for HLA matching? A clinical test of HistoCheck. *Bone Marrow Transplant* 2004; 34(4):367-368.

10c. Sypeithi. 2013. Ref Type: Internet Communication

11c. Suciu-Foca N, Ciubotariu R, Itescu S, Rose E A, Cortesini R. Indirect allorecognition of donor HLA-D R peptides in chronic rejection of heart allografts. *Transplant Proc* 1998; 30(8):3999-4000.

12c. Liu Z, Colovai A I, Tugulea S et al. Indirect recognition of donor HLA-D R peptides in organ allograft rejection. *J Clin Invest* 1996; 98(5):1150-1157.

13c. Ciubotariu R, Liu Z, Colovai A I et al. Persistent allopeptide reactivity and epitope spreading in chronic rejection of organ allografts. *J Clin Invest* 1998; 101(2): 398-405.

14c. Hornick P I, Mason P D, Baker R J et al. Significant frequencies of T cells with indirect antidonor specificity in heart graft recipients with chronic rejection. *Circulation* 2000; 101(20):2405-2410.

15c. IMGT. 2013. Ref Type: Internet Communication

20c. Nielsen M, Justesen S, Lund O, Lundegaard C, Buus S. NetMHCIIpan-2.0—Improved panspecific HLA-D R predictions using a novel concurrent alignment and weight optimization training procedure. *Immunome Res* 2010; 6:9.

21c. Otten H G, Calis J J, Kesmir C, van Zuilen A D, Spierings E. Predicted indirectly recognizable HLA epitopes presented by HLA-D R correlate with the de novo development of donor-specific HLA IgG antibodies after kidney transplantation. *Hum Immunol* 2013; 74(3): 290-296.

22c. EBMT data collection. 2013. Ref Type: Data File

23c. Furst D, Muller C, Vucinic V et al. High resolution HLA-matching in hematopoietic stem cell transplantation: a retrospective collaborative analysis. *Blood* 2013.

24c. NMDP. 2013. Ref Type: Internet Communication

25c. Lee S J, Klein J, Haagenson M et al. High-resolution donor-recipient HLA matching contributes to the success of unrelated donor marrow transplantation. *Blood* 2007; 110(13):4576-4583.

26c. Hurley C K, Woolfrey A, Wang T et al. The impact of HLA unidirectional mismatches on the outcome of myeloablative hematopoietic stem cell transplantation with unrelated donors. Blood 2013; 121(23):4800-4806.

31c. Przepiorka D, Weisdorf D, Martin P et al. 1994 Consensus Conference on Acute GVHD Grading. Bone Marrow Transplant 1995; 15(6):825-828.

32c. Shulman H M, Sullivan K M, Weiden P L et al. Chronic graft-versus-host syndrome in man. A long-term clinicopathologic study of 20 Seattle patients. Am J Med 1980; 69(2):204-217.

33c. Glidden D V, Vittinghoff E. Modelling clustered survival data from multicentre clinical trials. Stat Med 2004; 23(3):369-388.

34c. Iacobelli S. Suggestions on the use of statistical methodologies in studies of the European Group for Blood and Marrow Transplantation. Bone Marrow Transplant 2013; 48 Suppl 1:S1-37.

35c. Fleischhauer K, Shaw B E, Gooley T et al. Effect of T-cell-epitope matching at HLA-DPB1 in recipients of unrelated-donor haemopoietic-cell transplantation: a retrospective study. Lancet Oncol 2012; 13(4):366-374.

36c. Ballen K K, Koreth J, Chen Y B, Dey B R, Spitzer T R. Selection of optimal alternative graft source: mismatched unrelated donor, umbilical cord blood, or haploidentical transplant. Blood 2012; 119(9):1972-1980.

37c. Liu H L, Sun Z M, Geng L Q et al. Unrelated cord blood transplantation for newly diagnosed patients with severe acquired aplastic anemia using a reduced-intensity conditioning: high graft rejection, but good survival. Bone Marrow Transplant 2012; 47(9):1186-1190.

The invention claimed is:

1. Method for selecting and transplanting cells or a tissue preparation or organ for allogeneic transplantation comprising:
    obtaining and HLA (human leukocyte antigen)-typing a tissue sample:
    (a) from a transplant recipient or (b) from a transplant donor,
    accessing, via one or more computers, either
    a database with HLA-typing data of cells, tissue preparations or organs from multiple potential donors, or
    a database with HLA-typing data of cells, tissue preparations or organs from multiple potential recipients; and
    generating, via computer(s), a listing of mismatched HLA proteins-between the multiple potential donors and the transplant recipient of (a) or the one or more recipients and the transplant donor of (b), and
    determining, via the computer(s), for each of the multiple potential donors and the transplant recipient of (a) or the multiple potential recipients and the transplant donor of (b), a number of predicted indirectly recognized HLA epitopes (PIRCHES), wherein said PIRCHES are recipient- or donor- specific HLA-derived peptides from a mismatched recipient or donor -HLA protein respectively, and are predicted, by the computer(s), to be presented by an HLA molecule,
    wherein (i) the PIRCHES are identified by the computer(s) by identifying cleavage sites for the human proteasome within each mismatched HLA protein, wherein said PIRCHES are between 5 to 20 amino acids in length, and
    wherein (ii) the predicted presentation of PIRCHES identified in (i) by the HLA molecule is determined by the computer(s) by determining the IC50 binding value for binding between said PIRCHES identified in (i) and the HLA molecule, wherein PIRCHES are predicted to bind the HLA molecule when an IC50 score of $\leq 10$ μM is determined,
    wherein the likelihood of an immune response after transplantation, wherein the immune response includes at least T-cell-alloreactivity against (HLA), is increased with an increased number of PIRCHES,
    selecting the cell or tissue preparation or organ for the allogenic transplantation from a donor from the multiple potential donors or a recipient from the multiple potential recipients with the lowest PIRCHE score of said multiple potential donors or recipients,
    and transplanting the cells, tissue preparation or organ of the donor with the lowest PIRCHE score of said multiple potential donors into the transplant recipient of (a) or transplanting the cells, tissue preparation or organ of the transplant donor of (b) into the recipient with the lowest PIRCHE score of said multiple potential recipients.

2. The method according to claim 1, wherein said transplanting comprises transplanting stem cells.

3. The method according to claim 2, wherein said transplanting comprises transplanting haematopoietic stem-cells (HSCTs).

4. The method according to claim 1, wherein said transplanting comprises transplanting cord blood or cord blood cells.

5. The method according to claim 1, wherein said organ is a kidney.

6. The method according to claim 1, wherein the method further assesses therapeutic outcome selected from the group consisting of patient survival, disease free survival and transplant-related mortality.

7. The method according to claim 1, wherein said immune response comprises:
    (i) an antibody-mediated response;
    (ii) an unwanted alloreactivity;
    (iii) a wanted alloreactivity;
    (iv) an acute graft versus host disease (aGVHD) or chronic graft host disease (cGVHD); and/or
    (v) de novo development of donor specific HLA IgG antibodies after kidney transplantation.

8. The method according to claim 1, wherein said PIRCHES are nonameric peptides.

9. The method according to claim 1, wherein said PIRCHES are presented by shared HLA class I (PIRCHE I) or by shared HLA class II (PIRCHE II).

10. The method according to claim 9, wherein PIRCHE-I peptides have a predicted IC50 binding value of $\leq 10$ μm.

11. The method according to claim 9, wherein PIRCHE-II peptides have a predicted IC50 binding value of $\leq 20$ μm.

12. The method according to claim 1, wherein the HLA typing is carried out on HLA subtypes HLA-A, HLA-B, HLA-C, HLA-DRB1, HLA-DQB1, HLA-DPB1, DQA1, DPA1, -G, -E, -F, MICA, MICB and/or KIR.

13. The method according to claim 1, wherein the HLA typing:
    (i) comprises serological and/or molecular typing;
    (ii) is carried out at high resolution level with sequence-based typing;
    (iii) comprises sequencing of exon 1-7 for HLA class I alleles and exon 1-6 for HLA class II alleles; and/or
    (iv) comprises high resolution HLA-A, -B, -C, -DRB1 and -DQB1 typing of exons 2and 3 for HLA class-I alleles and exon 2 for HLA class-II alleles.

14. The method according to claim 1, wherein donor material for allogeneic transplantation originates from:

(i) a donor with at least one allelic match;
(ii) a donor with 10/10 matches an HLA-DP mismatch; or
(iii) a 9/10-matched unrelated donor.

15. The method according to claim 1, wherein the PIRCHES include PIRCHE-I and PIRCHE-II and wherein donor material is transplanted when:
(i) the number of PIRCHE-I ≤3
(ii) the number of PIRCHE-II ≤4; or
(iii) the number of combined PIRCHE-I and PIRCHE-II ≤6.

16. The method according to claim 1, wherein HLA-DQB1 antigenic mismatches are interrogated.

17. The method according to claim 1, comprising the analysis of multiple HLA mismatched donors, thereby determining the best donor of said multiple donors, and/or determining alloreactivity between multiple donors.

18. The method according to claim 7, wherein the wanted alloreactivity is an anti-leukemic alloreactivity.

19. The method according to claim 1, wherein the PIRCHES are 8 to 15 amino acids in length.

20. The method according to claim 10, wherein PIRCHE-I peptides have a predicted IC50 binding value of ≤1000nm.

21. The method according to claim 11, wherein PIRCHE-II peptides have a predicted IC50 binding value of 5 μm.

22. The method according to claim 15, wherein donor material for allogeneic transplantation is associated with low risk of an unwanted immune response where:
(i) the number of PIRCHE-I ≤2;
(ii) the number of PIRCHE-II ≤3; and/or
(iii) the number of combined PIRCHE-I and PIRCHE-II ≤4.

23. Method for selecting and transplanting cells or a tissue preparation or organ for allogeneic transplantation comprising:
carrying out a computer-implemented method for assessing a likelihood of an immune response after transplantation, wherein said immune response comprises T-cell-alloreactivity against human leukocyte antigens (HLA) that are mismatched between one or more donors and one or more recipients, said method comprising:
HLA-typing of samples obtained from multiple potential donors and one or more recipients and/or provision of HLA typing data from the multiple potential donors and the one or more recipients,
generating, via computer(s), a listing of mismatched HLA proteins between the multiple potential donors and the one or more recipients, and
determining, via the computer(s), for each of the multiple potential donors and the one or more transplant recipients a number of predicted indirectly recognized HLA epitopes (PIRCHES), wherein said PIRCHES are recipient- or donor-specific HLA-derived peptides from a mismatched recipient or donor -HLA protein respectively, and are predicted, by the computer(s), to be presented by an HLA molecule,
wherein (i) PIRCHES are identified by the computer(s) by-identifying cleavage sites for the human proteasome within each mismatched HLA protein, wherein said PIRCHES are between 5 to 20 amino acids in length, and
wherein (ii) the predicted presentation of-PIRCHES identified in (i) the HLA molecule is determined by the computer(s) by determining the IC50 binding value for binding between said PIRCHES identified in (i) and the HLA molecule, wherein PIRCHES are predicted to bind the HLA molecule when an IC50 score of ≤10μM is determined, wherein the likelihood of said immune response after transplantation is increased with an increased number of PIRCHES,
selecting the cell or tissue preparation or organ for the allogenic transplantation from a donor of the multiple potential donors with the lowest PIRCHE score of said multiple potential donors,
and transplanting the cells, tissue preparation or organ of the donor with the lowest PIRCHE score of said multiple potential donors into the one or more recipients.

* * * * *